(12) United States Patent
Malkowski

(10) Patent No.: US 11,013,524 B2
(45) Date of Patent: May 25, 2021

(54) SYSTEMS FOR PERFORMING ENDOSCOPIC PROCEDURES

(71) Applicant: Covidien LP, Mansfield, MA (US)

(72) Inventor: Jaroslaw T. Malkowski, Trumbull, CT (US)

(73) Assignee: Covidien LP, Mansfield, MA (US)

(*) Notice: Subject to any disclaimer, the term of this patent is extended or adjusted under 35 U.S.C. 154(b) by 287 days.

(21) Appl. No.: 16/052,679

(22) Filed: Aug. 2, 2018

(65) Prior Publication Data

US 2018/0338772 A1 Nov. 29, 2018

Related U.S. Application Data

(62) Division of application No. 14/164,292, filed on Jan. 27, 2014, now Pat. No. 10,058,343.

(60) Provisional application No. 61/782,700, filed on Mar. 14, 2013.

(51) Int. Cl.
*A61B 17/29* (2006.01)
*A61B 17/00* (2006.01)

(52) U.S. Cl.
CPC .... *A61B 17/29* (2013.01); *A61B 2017/00362* (2013.01); *A61B 2017/292* (2013.01); *A61B 2017/294* (2013.01); *A61B 2017/2931* (2013.01); *A61B 2017/2936* (2013.01)

(58) Field of Classification Search
CPC .................. A61B 17/072; A61B 17/29; A61B 2017/00362; A61B 2017/00473; A61B 2017/292; A61B 2017/2931; A61B 2017/2936; A61B 2017/294
See application file for complete search history.

(56) References Cited

U.S. PATENT DOCUMENTS

| | | | |
|---|---|---|---|
| 5,352,235 A | 10/1994 | Koros et al. | |
| 5,441,059 A | 8/1995 | Dannan | |
| 5,562,640 A | 10/1996 | McCabe et al. | |
| 5,792,165 A | 8/1998 | Klieman et al. | |
| 5,893,875 A | 4/1999 | O'Connor et al. | |
| 6,358,267 B1 | 3/2002 | Murakami et al. | |
| 7,604,642 B2 | 10/2009 | Brock | |
| 7,666,181 B2 | 2/2010 | Abou El Kheir | |
| 7,691,126 B2 | 4/2010 | Bacher | |
| 7,901,398 B2 | 3/2011 | Stanczak et al. | |
| 8,021,358 B2 | 9/2011 | Doyle et al. | |
| 8,088,062 B2 | 1/2012 | Zwolinski | |
| 8,133,254 B2 | 3/2012 | Dumbauld et al. | |
| 9,629,633 B2 | 4/2017 | Williams et al. | |

(Continued)

FOREIGN PATENT DOCUMENTS

WO 2012112622 A2 8/2012

OTHER PUBLICATIONS

European Search Report EP 14159416 dated Jun. 4, 2014.

(Continued)

*Primary Examiner* — George J Ulsh
(74) *Attorney, Agent, or Firm* — Carter, DeLuca & Farrell LLP

(57) ABSTRACT

A system for performing an endoscopic procedure is provided. The system includes an actuation assembly having a handle assembly and a shaft assembly. The system also includes an end effector configured for selective and operative connection to a distal end of the shaft assembly. The system further includes a holder for selectively engaging the end effector and facilitating attachment of the end effector to the shaft assembly.

21 Claims, 38 Drawing Sheets

(56) References Cited

U.S. PATENT DOCUMENTS

| | | |
|---|---|---|
| 9,681,866 B2 | 6/2017 | Halac |
| 9,801,648 B2 | 10/2017 | Houser |
| 10,058,343 B2 | 8/2018 | Malkowski |
| 2004/0267254 A1 | 12/2004 | Manzo et al. |
| 2005/0033354 A1 | 2/2005 | Montalvo et al. |
| 2005/0216033 A1 | 9/2005 | Lee et al. |
| 2006/0184161 A1 | 8/2006 | Maahs et al. |
| 2008/0004656 A1 | 1/2008 | Livneh |
| 2008/0147113 A1 | 6/2008 | Nobis |
| 2008/0242939 A1 | 10/2008 | Johnston |
| 2008/0243106 A1 | 10/2008 | Coe et al. |
| 2008/0287926 A1 | 11/2008 | Abou El Kheir |
| 2009/0209947 A1 | 8/2009 | Gordin et al. |
| 2011/0087265 A1 | 4/2011 | Nobis |
| 2011/0196494 A1 | 8/2011 | Yedlicka |
| 2012/0083826 A1 | 4/2012 | Chao et al. |
| 2012/0232658 A1 | 9/2012 | Morgenstern |
| 2012/0259325 A1 | 10/2012 | Houser et al. |
| 2012/0316575 A1 | 12/2012 | Farin et al. |
| 2013/0085341 A1 | 4/2013 | Nobis |
| 2014/0088637 A1 | 3/2014 | Parihar |
| 2014/0088638 A1 | 3/2014 | Parihar |

OTHER PUBLICATIONS

Chinese Office Action dated Jan. 17, 2018, issued in JP Application No. 201410097509.
Extended European Search Report EP14159416 dated Aug. 18, 2014.
Chinese Office Action dated Aug. 25, 2020, issued in CN Appln. No. 201811032523, 8 pages.

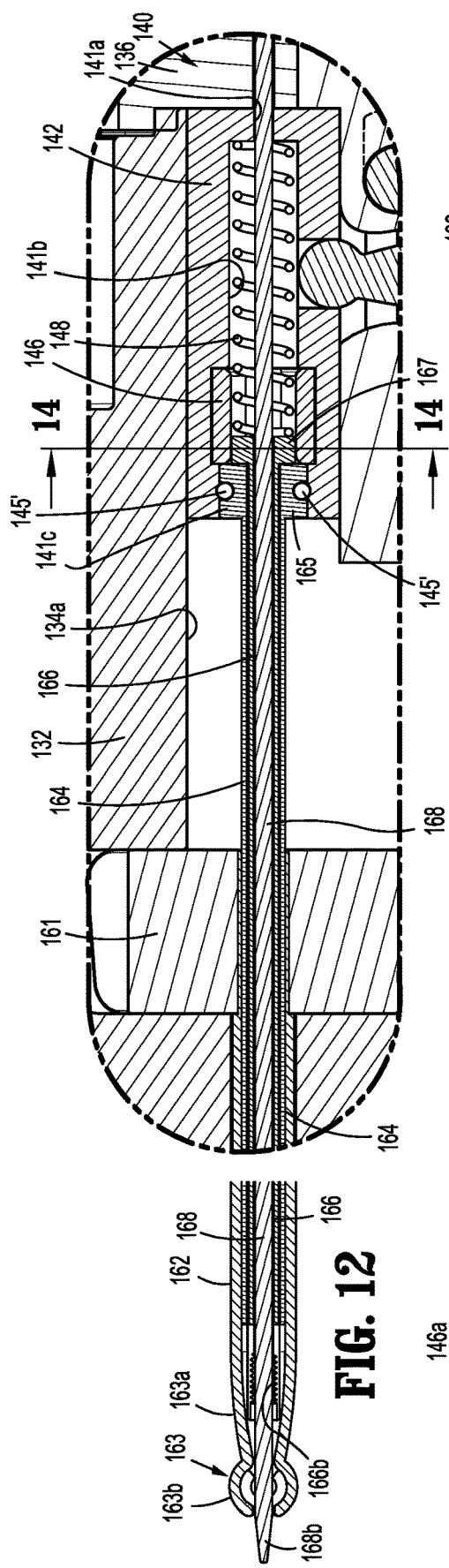
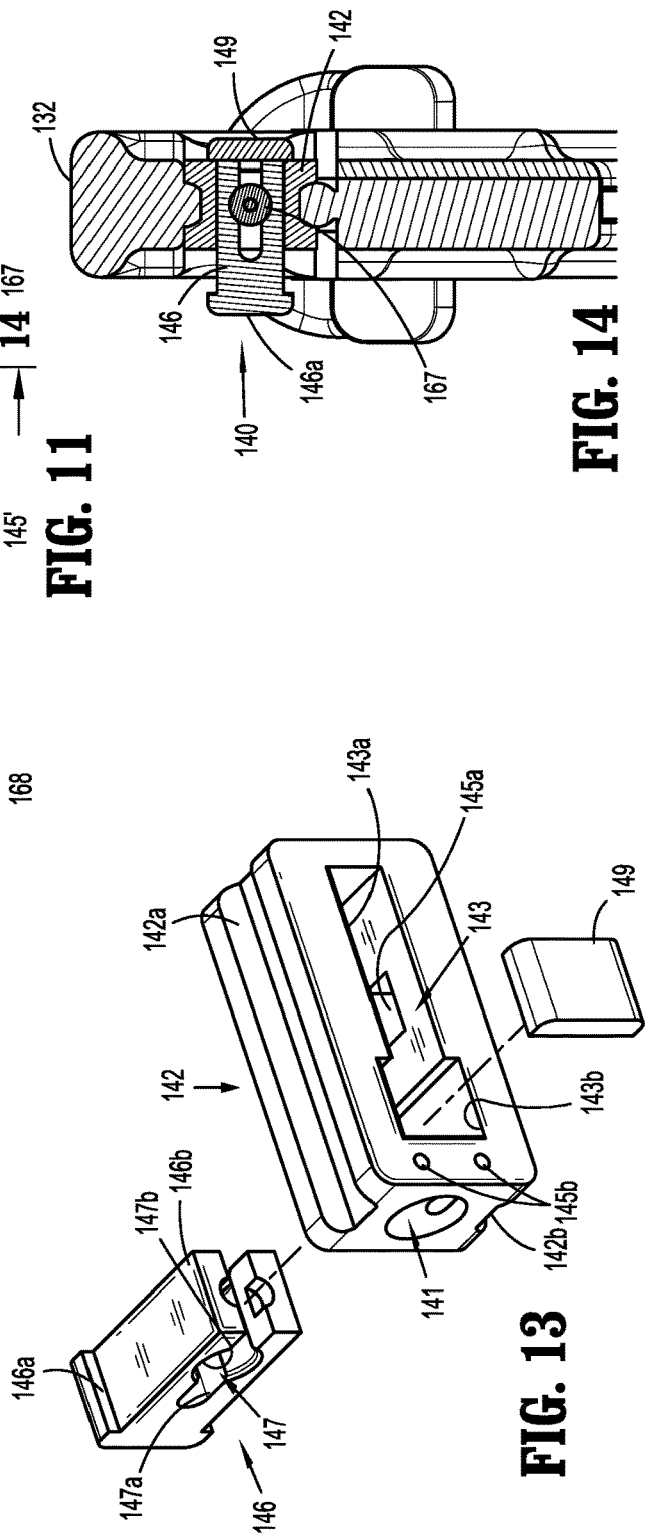
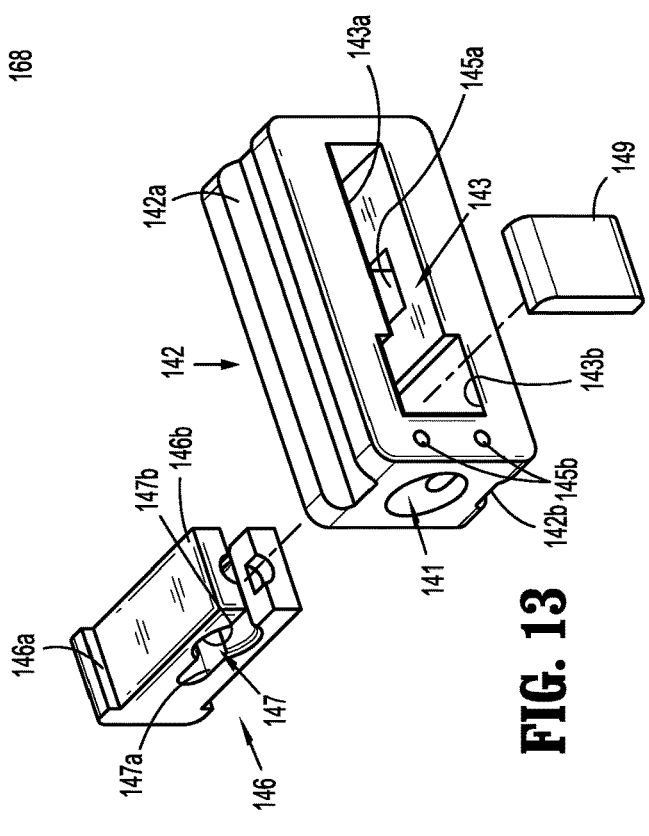
FIG. 11
FIG. 12
FIG. 13
FIG. 14

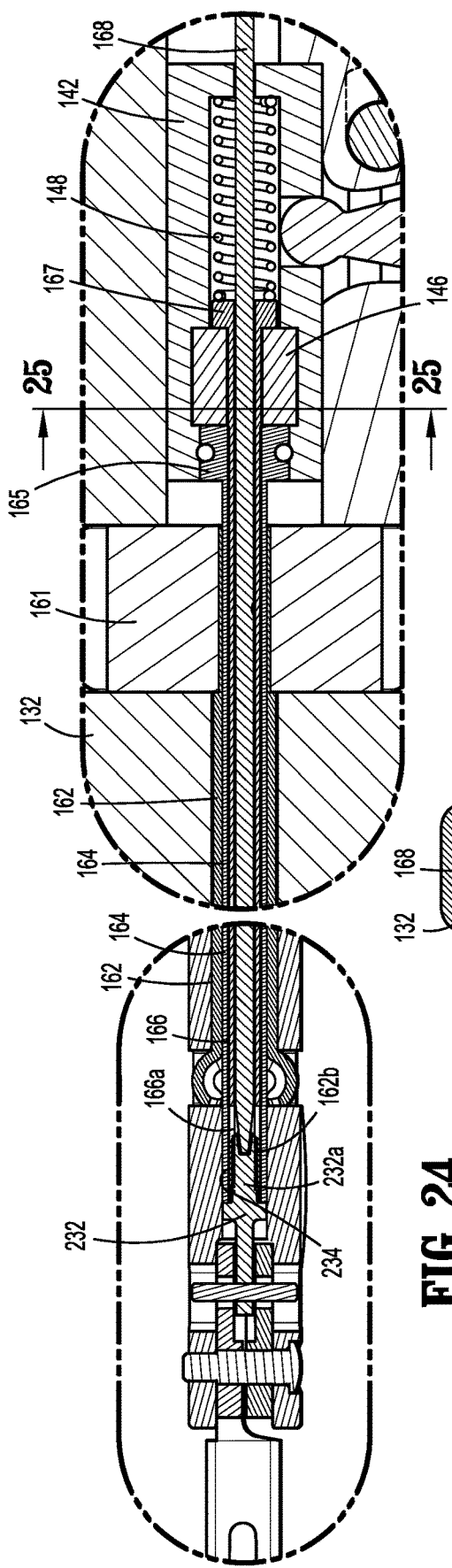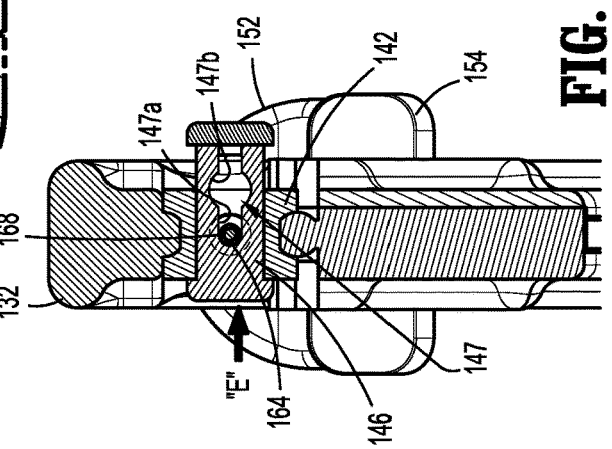
FIG. 23
FIG. 24
FIG. 25

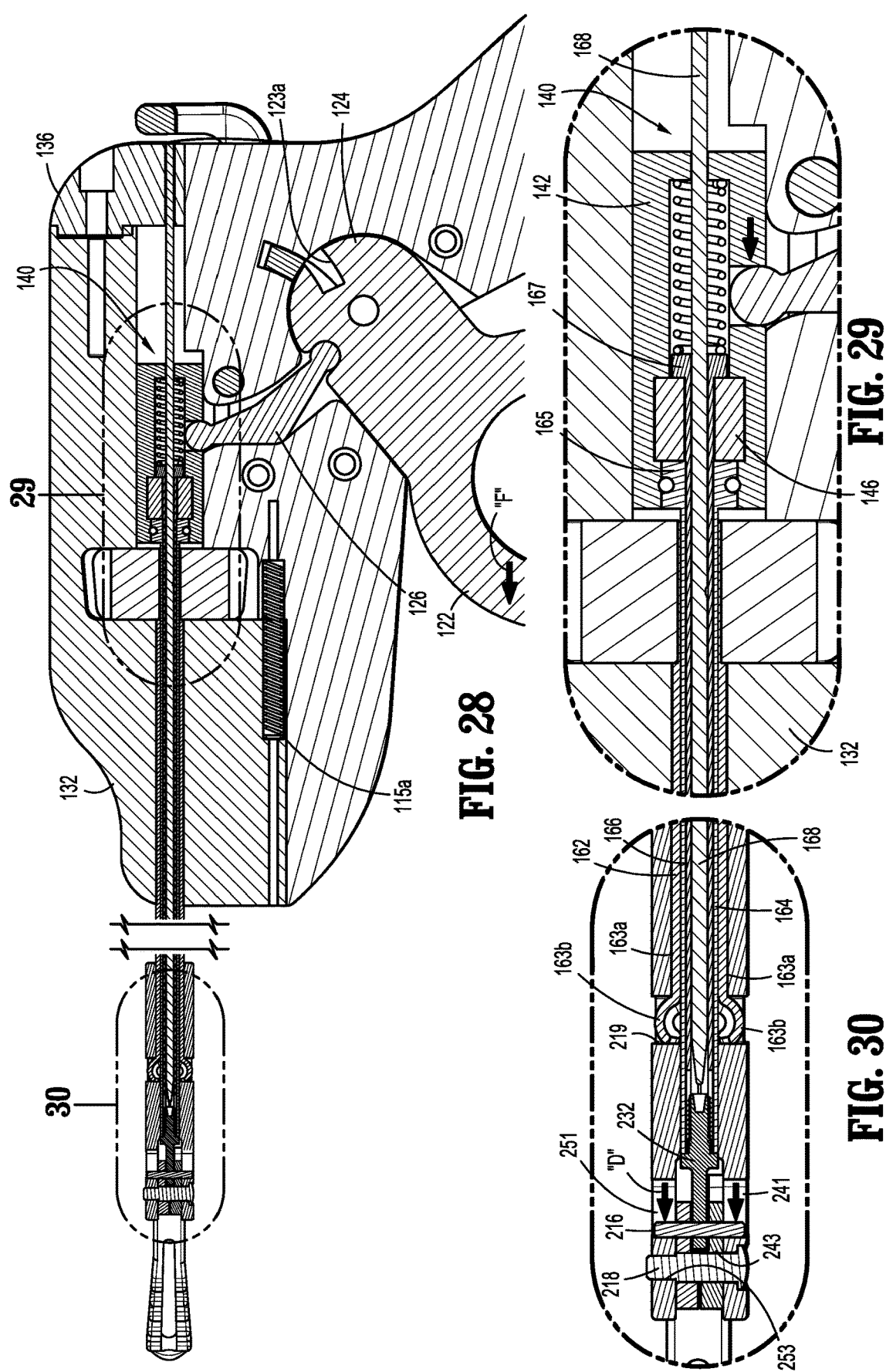

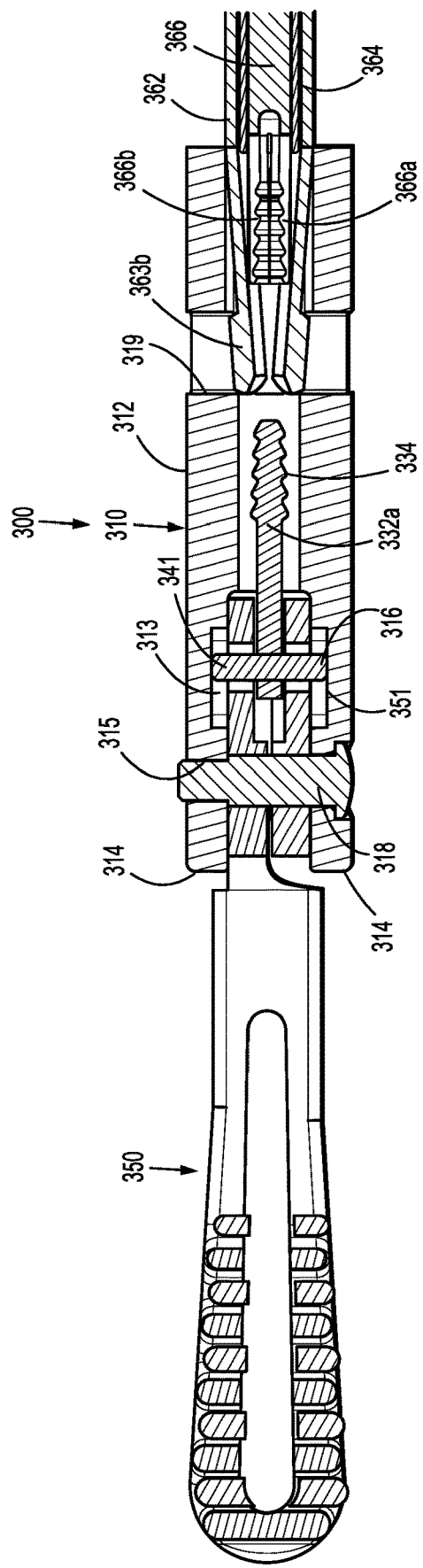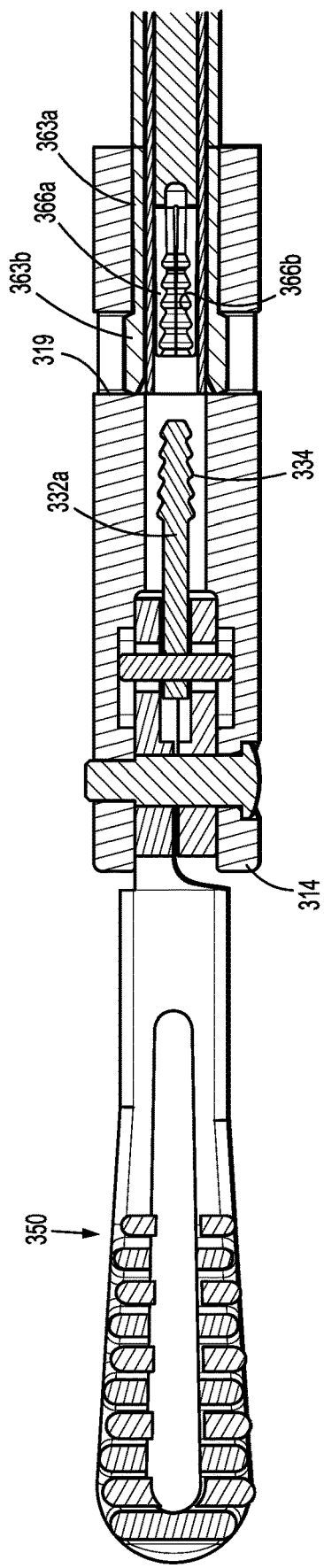
FIG. 35
FIG. 36

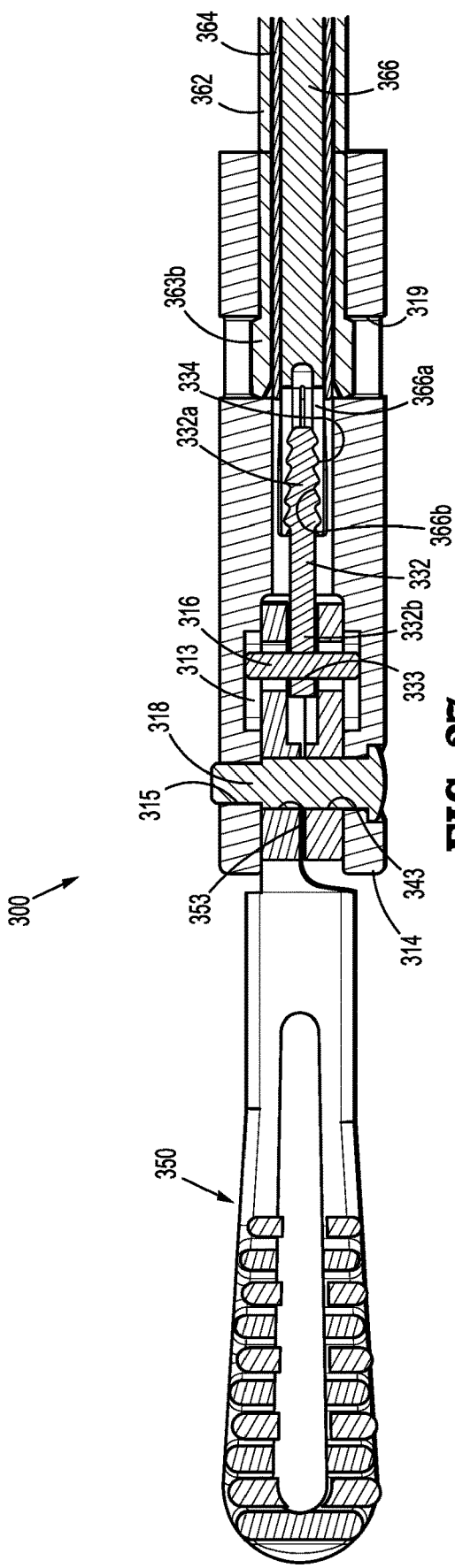
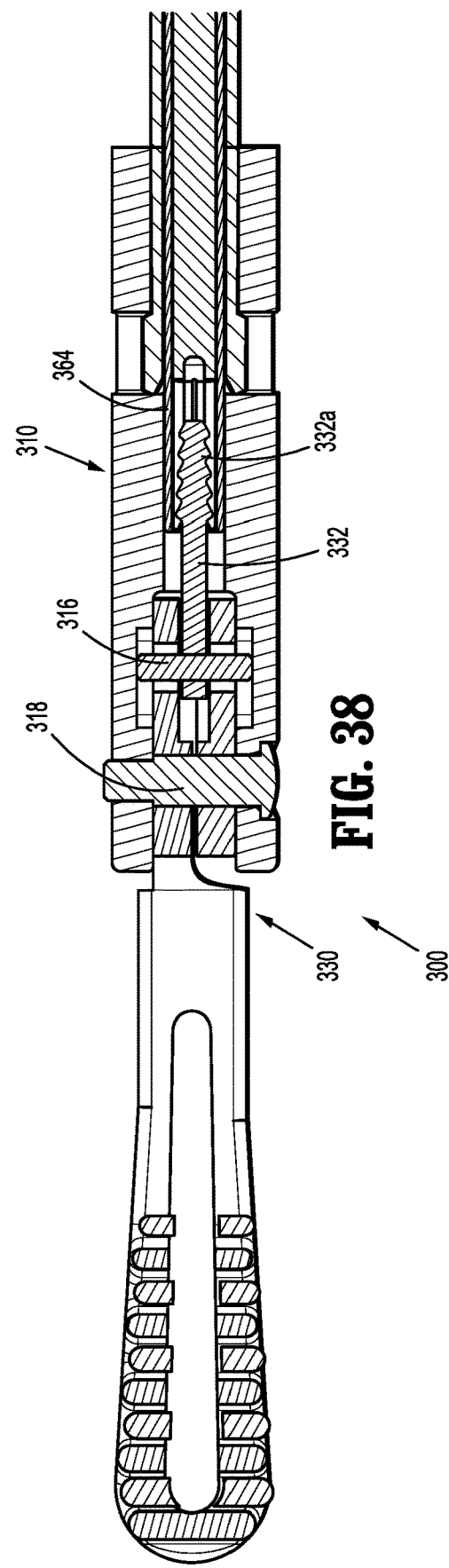
FIG. 37
FIG. 38

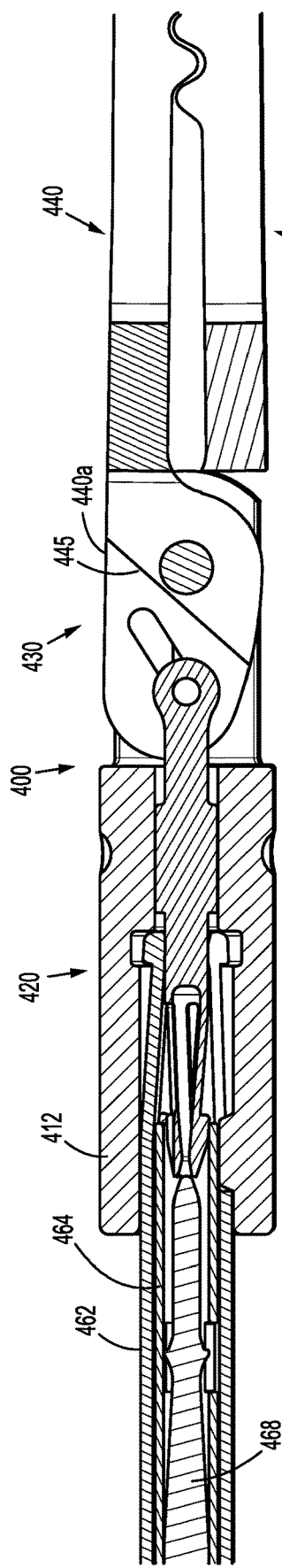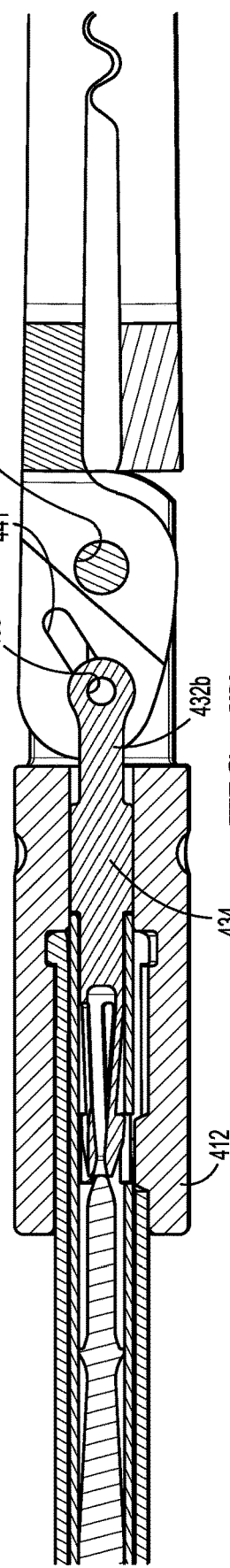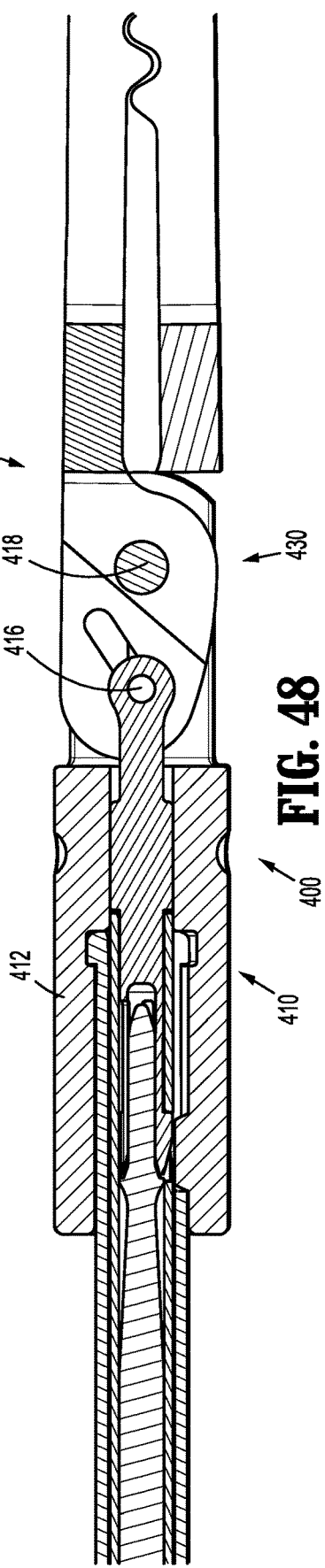

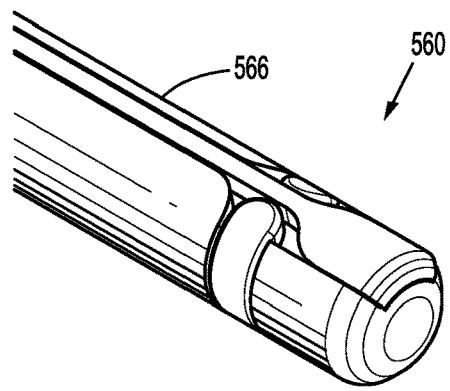
FIG. 51
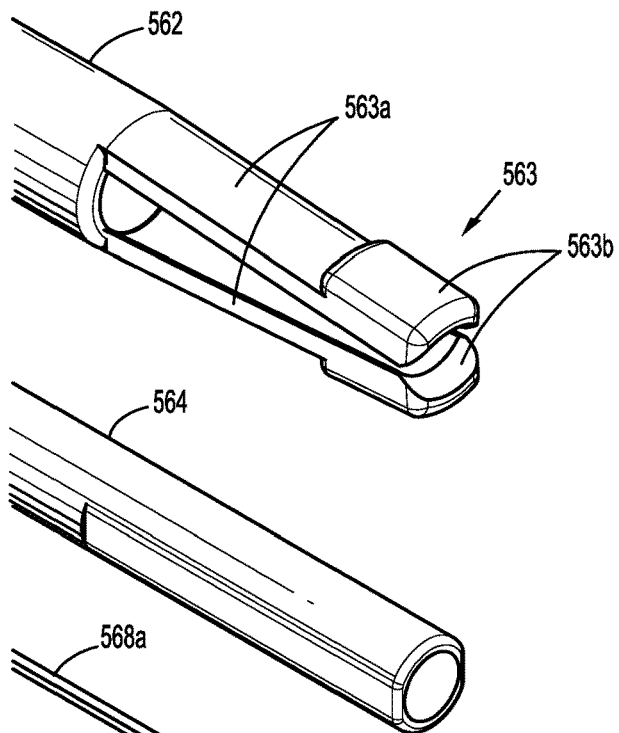
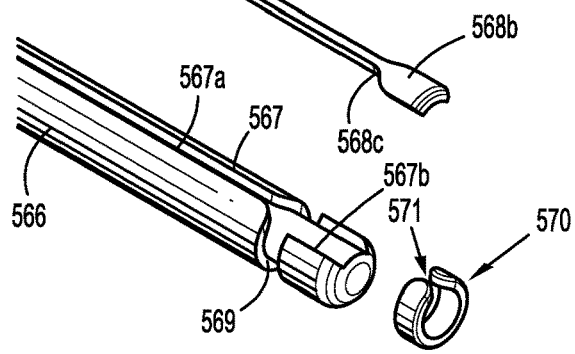
FIG. 52

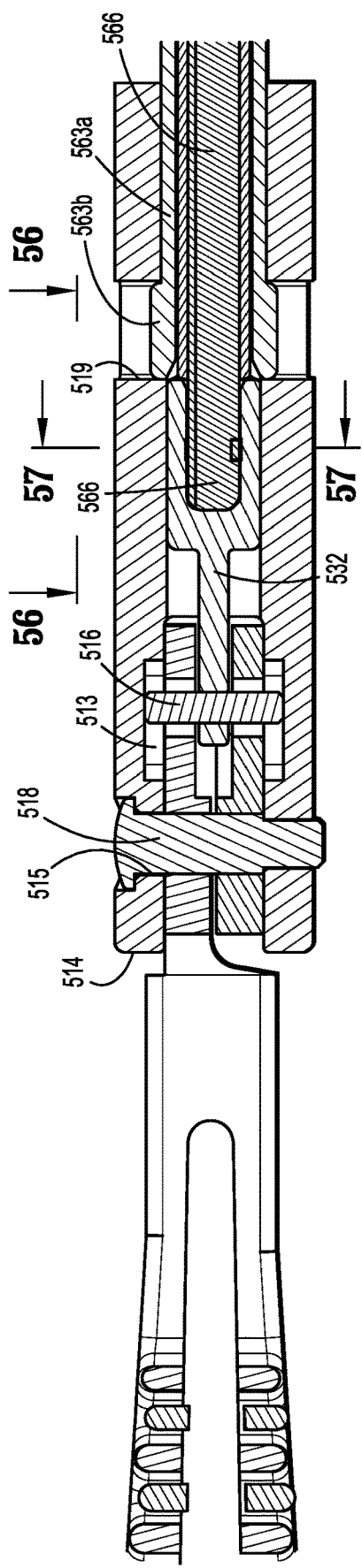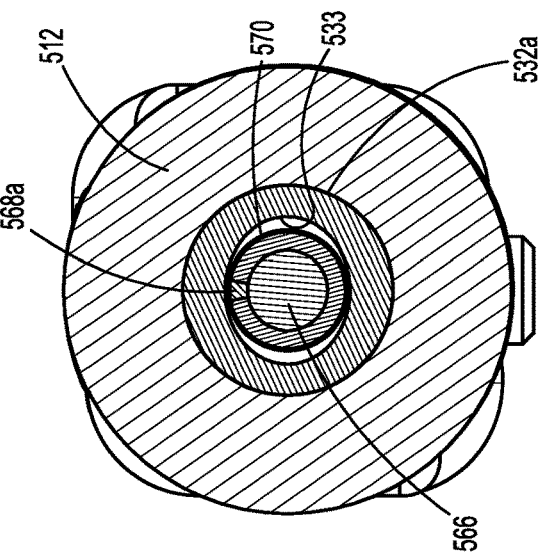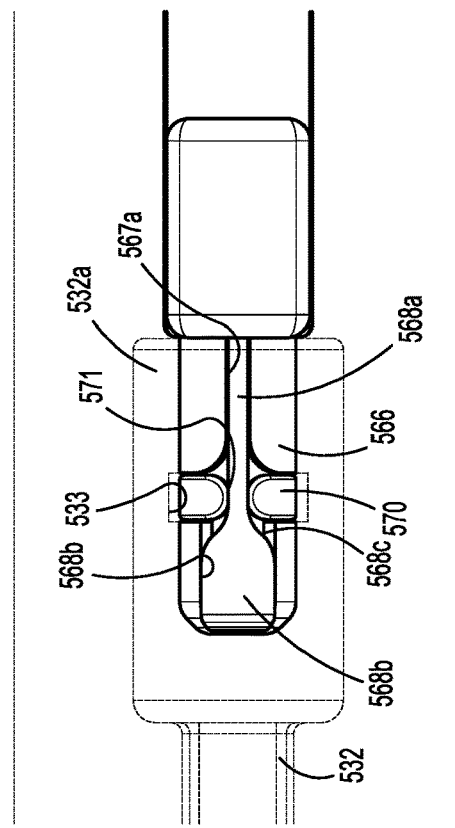
FIG. 55
FIG. 57
FIG. 56

SYSTEMS FOR PERFORMING ENDOSCOPIC PROCEDURES

CROSS-REFERENCE TO RELATED APPLICATIONS

This application is a divisional of U.S. patent application Ser. No. 14/164,292 filed Jan. 27, 2014, which claims the benefit of and priority to U.S. Provisional Patent Application No. 61/782,700, filed Mar. 14, 2013, the entire disclosure of which is incorporated by reference herein.

BACKGROUND

Technical Field

The present disclosure relates to endoscopic surgery, and more particularly, to a system for performing endoscopic procedures.

Background of Related Art

Surgery often requires access to internal tissue through open surgical procedures or endoscopic surgical procedures. As used herein, the term "endoscopic" refers to all types of minimally invasive surgical procedures including laparoscopic, arthroscopic, natural orifice intraluminal, and natural orifice transluminal procedures. Endoscopic surgery has numerous advantages compared to traditional open surgical procedures, including reduced scarring. Endoscopic surgery is often performed in an insufflatory fluid present within the body cavity, such as carbon dioxide or saline, to provide adequate space to perform the intended surgical procedures. The insufflated cavity is generally under pressure and is sometimes referred to as being in a state of pneumoperitoneum. Surgical access devices are often used to facilitate surgical manipulation of internal tissue while maintaining pneumoperitoneum. For example, trocars are often used to provide a port through which endoscopic surgical instruments are passed. Trocars generally have an instrument seal, which prevents the insufflatory fluid from escaping while an instrument is positioned in the trocar. Alternatively, an instrument may be inserted directly through an opening, i.e., incision, in tissue into the body cavity.

The size of the instrument used during a endoscopic procedure is limited by the size of port through which the endoscopic instruments are inserted. The larger a port, the larger the instrument that may be inserted therethrough, however, also the larger the resulting scar in the tissue. To overcome the limitation in the size of the instrument presented by the size of the port, it would be beneficial to provide an endoscopic instrument having a distal shaft with a first cross-sectional size that may be received either directly through tissue, or alternatively, through an instrument port, and one or more end effectors having an enlarged cross-sectional size that may be introduced into a cavity through an alternative means, i.e., a second larger instrument port, and may be selectively attached to and disconnected from the distal shaft within the body cavity.

SUMMARY

A system for performing an endoscopic procedure is provided. The system includes an actuation assembly having a handle assembly and a shaft assembly. The system also includes an end effector configured for selective and operative connection to a distal end of the shaft assembly. The system further includes a holder for selectively engaging the end effector and facilitating attachment of the end effector to the shaft assembly.

Also provided is an instrument for performing endoscopic procedures. The instrument includes an actuation assembly having a handle assembly and a shaft assembly. The handle assembly includes a trigger mechanism, a slider mechanism, a drive mechanism, and a latch mechanism. The shaft assembly includes a connection mechanism, the connection assembly including an outer tube, a center tube slideably disposed relative to the outer tube, an inner tube slidably disposed relative to the outer and center tubes and a center rod slideably disposed relative to outer, center, and inner tubes. The instrument may further include an end effector operably engaged with the connection mechanism. The end effector may include a connection assembly and a jaw assembly. The connection assembly may include a tubular body having a pair of distal supports extending distally therefrom for operable engagement with jaw assembly. The jaw assembly may include a link member, a first jaw member, and a second jaw member.

In addition, a holder for facilitating attachment of an end effector to an actuation assembly is provided. The holder includes an outer tube defining a longitudinal axis and an inner shaft slidably disposed within the outer tube. The inner shaft includes distally extending arms configured to be flexed inwardly upon engagement with the outer tube. The holder also includes a capsule pivotally mounted between the distally extending arms. The capsule includes a substantially cylindrical body configured for select reception of an end effector. Inward flexion of the arms of the inner shaft pivotally fixes the capsule relative to the inner shaft.

Further provided is a kit for performing an endoscopic procedure. The kit includes an actuation assembly for manipulating an end effector during an endoscopic procedure, a first end effector for performing a first function, a second end effector for performing a second function, and a holder configured to selectively support the first and second end effectors.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiment(s) given below, serve to explain the principles of the disclosure, wherein:

FIG. 11 is an enlarged view of portion 11 shown in FIG. 10;

FIG. 12 is an enlarged view of portion 12 shown in FIG. 10;

FIG. 13 is an enlarged view of portion 13 shown in FIG. 5;

FIG. 14 is a cross-sectional view taken along line 14-14 shown in FIG. 11;

FIG. 23 is an enlarged view of portion 23 shown in FIG. 22;

FIG. 24 is an enlarged view of portion 24 shown in FIG. 22;

FIG. 25 is a cross-sectional view taken along line 25-25 shown in FIG. 23;

FIG. 28 is a cross-sectional view of the of endoscopic instrument as shown in FIG. 27;

FIG. 29 is an enlarged view of portion 23 shown in FIG. 28;

FIG. 30 is an enlarged view of portion 24 shown in FIG. 28;

FIG. 35 is a cross-sectional side view of the end effector and the distal end of the connection mechanism shown in FIG. 31, during a first step of attaching the end effector to the connection mechanism;

FIG. 36 is a cross-sectional side view of the end effector and the distal end of the connection mechanism shown in FIG. 35, during a subsequent attachment step;

FIG. 37 is a cross-sectional side view of the end effector and the distal end of the connection mechanism shown in FIG. 35, during another attachment step;

FIG. 38 is a cross-sectional side view of the end effector and the distal end of the connection mechanism shown in FIG. 35, upon complete attachment of the end effector to the distal end of the connection mechanism;

FIG. 46 is a cross-sectional side view of the end effector and the distal end of the connection mechanism shown in FIG. 40, during a first step of attaching the end effector to the connection mechanism;

FIG. 47 is a cross-sectional side view of the end effector and the distal end of the connection mechanism shown in FIG. 40, during a subsequent attachment step;

FIG. 48 is a cross-sectional side view of the end effector and the distal end of the connection mechanism shown in FIG. 40, upon complete attachment of the end effector to the distal end of the connection mechanism;

FIG. 51 is a perspective view of the distal end of the connection mechanism shown in FIG. 50, in a position ready for connection with the end effector shown in FIG. 50;

FIG. 52 is an enlarged exploded view of the distal end of the connection mechanism shown in FIG. 51;

FIG. 55 is a cross-sectional side view of the end effector and the distal end of the connection mechanism shown in FIG. 50, during another attachment step;

FIG. 56 is a top view of the end effector and the distal end of the connection mechanism shown in FIG. 55, with the tubular body of the end effector shown in phantom;

FIG. 57 is a cross-sectional view taken along line 57-57 shown in FIG. 55;

DETAILED DESCRIPTION

Figure 1:
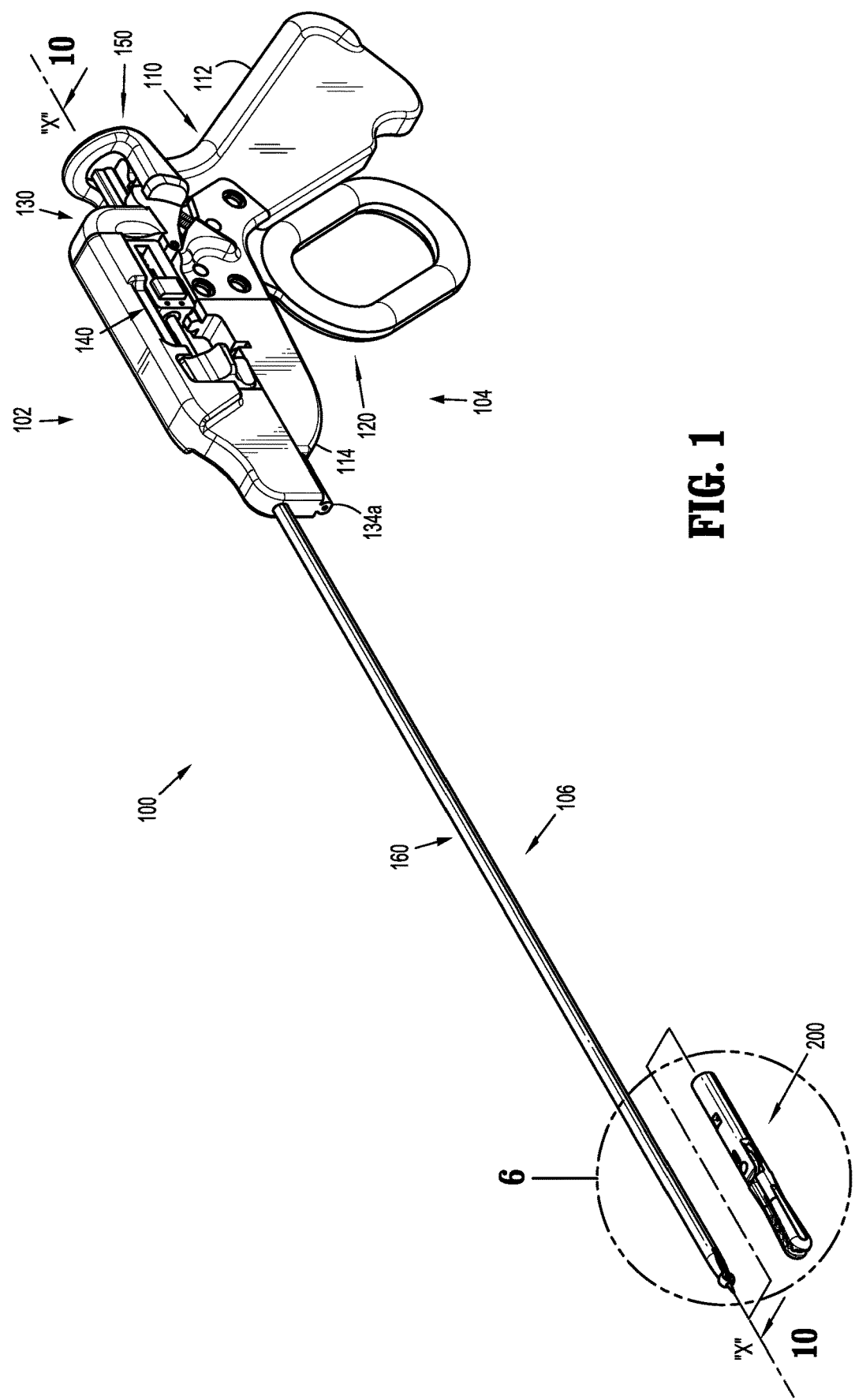
FIG. 1 is a perspective view of the a endoscopic instrument according to an embodiment of the present disclosure.

Embodiments of the presently disclosed system for performing endoscopic procedures will now be described in detail with reference to the drawings in which like reference numerals designate identical or corresponding elements in each of the several views. As is common in the art, the term "proximal" refers to that part or component closer to the user or operator, i.e., surgeon or physician, while the term "distal" refers to that part or component further away from the user.

With reference initially to FIG. 1, an endoscopic instrument according to an embodiment of the present disclosure is shown generally as endoscopic instrument 100. Instrument 100 includes an actuation assembly 102 and an end effector 200. As will be discussed in further detail below, instrument 100 is configured such that end effector 200 may be attached, operated, and separated from actuation assembly 102 during a laparoscopic procedure, and more particularly, while end effector 200 is disposed within a body cavity. Although shown and described for use with a grasping end effector, it is envisioned that actuation assembly 102 may be used with other types of end effectors, including those for stapling, vessel sealing and cutting. As will be discussed in further detail below, actuation assembly 102 may be modified for use with any of the presently disclosed end effectors. It is further envisioned that end effector 200 may be modified for use with other actuation assemblies.

Figure 5:
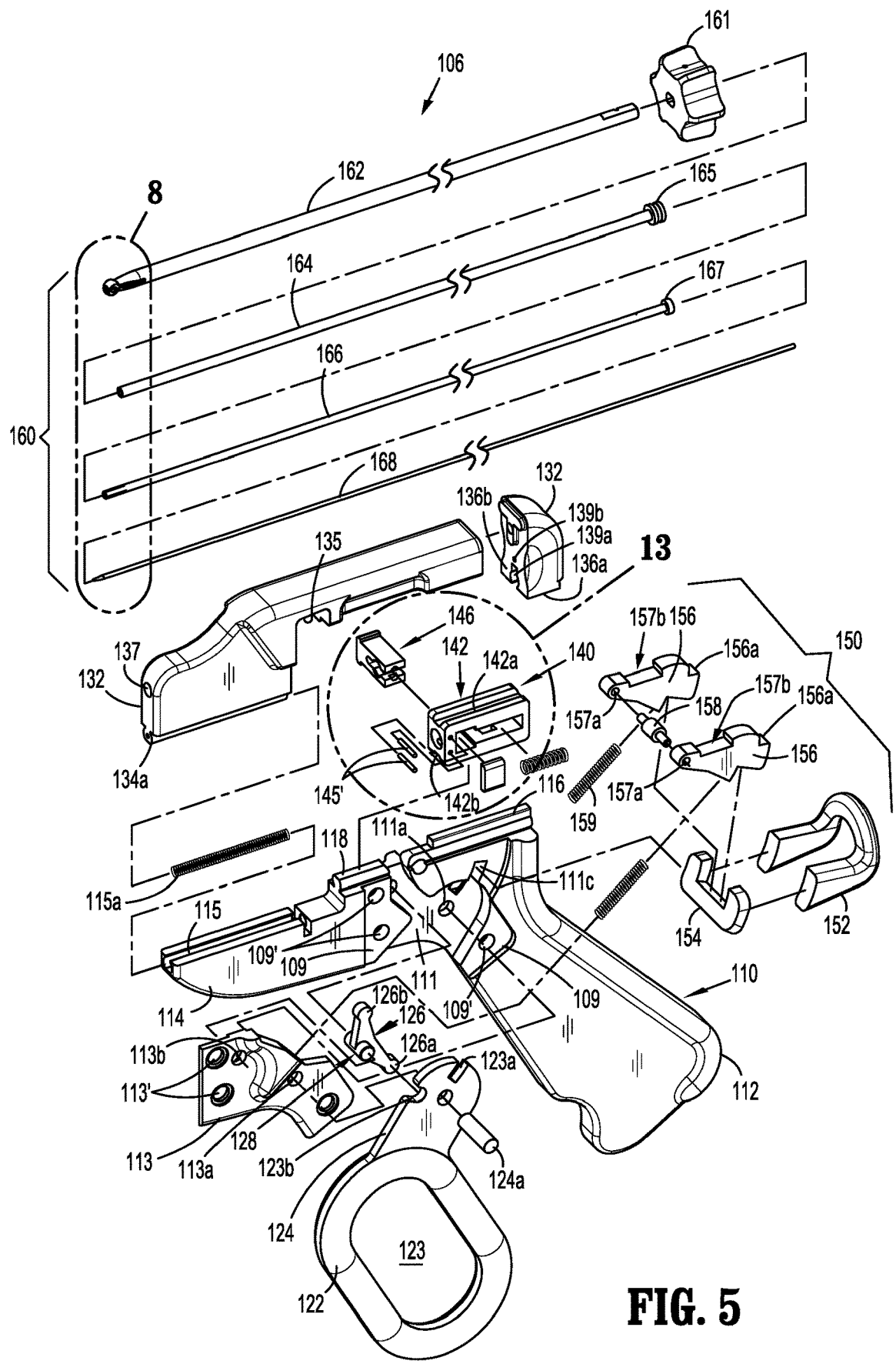
FIG. 5 is an exploded perspective view of the actuation assembly shown in FIG. 2.

With reference now to FIGS. 1-5, actuation assembly 102 includes a handle assembly 104 and a shaft assembly 106 extending from handle assembly 104. With particular reference to FIG. 5, handle assembly 104 includes a base member 110, a trigger mechanism 120, a slider mechanism 130, a drive mechanism 140, and a latch mechanism 150.

With reference still to FIGS. 1-5, base member 110 includes a handle portion 112 and a distal extension 114 and defines a cutout 111 therebetween. Cutout 111 is configured to operably receive an actuation link 126 of trigger mechanism 120. Defined within cutout 111 is a first opening 111*a* configured to receive a pivot pin 124*a* of trigger mechanism 120 for pivotally securing trigger 122 of trigger mechanism 120 to handle assembly 104, a second opening 111*b* configured to receive a first portion of a pivot member 128 of trigger link 126 of trigger mechanism 120, a third opening 111*c* configured to receive a pivot member 158 of latch mechanism 150, and a notch 111*d* configured to selectively receive a first lock member 154 of latch mechanism 150.

With particular reference to FIG. 5, base member 110 further includes a cover plate 113 for covering cutout 111. Cover plate 113 defines a plurality of opening corresponding to openings in cutout 111. In particular, cover plate 113 includes a first opening 113*a* configured to receive pivot pin 124*a* of trigger mechanism 120 and a second opening 113*a* configured to receive a second portion of pivot member 128 of trigger link 126. A recess 109 is formed about cutout 111 and is configured to accommodate cover plate 113. As shown, a plurality of openings 109' are defined within recess 109 and correspond in number and location to a plurality of openings 113' formed in cover plate 113. Openings 109' formed in recess 109 and openings 113' formed in cover plate 113 are each configured to receive a screw (not shown) for securing cover plate 113 to base member 110. Although described as being secured to base member 110 using a plurality of screws, cover plate 113 may be secured to base member 110 using any suitable technique, i.e., adhesive, welding, snap-fit.

With particular reference still to FIG. 5, handle portion 112 of base member 110 is configured for operable engagement by a user. Handle portion 112 may be ergonomically formed and may include knurling, grips, non-slip coating or other features (not shown) to facilitate engagement by a user. Distal extension 114 of base member 110 includes a first rail 116 and a second rail 118. First rail 116 extends longitudinally along a proximal portion of distal extension 114 and is configured to support a slider extension 136 of slider mechanism 130 in a sliding manner. Second rail 118 extends longitudinally along a central portion of distal extension 114 and is configured to be slidably received within a groove 142b of a drive box 142 of drive mechanism 140. Distal extension 114 defines a channel 115 extending longitudinally along a distal portion thereof. Channel 115 is configured to slidably receive slider 132 of slider mechanism 130. Channel 115 is further configured to receive a spring 115a. Spring 115a is configured to bias slide mechanism 130 distally.

Still referring to FIGS. 1-5, trigger mechanism 120 includes a trigger 122 and a trigger link 126. As shown, trigger 122 includes a substantially oval-shaped member defining an opening 123 configured to accommodate the fingers of a user. A flange 124 extends from trigger 122 and is configured to be received within cutout 113 formed between handle portion 112 and distal extension 114 of handle assembly 104. Flange 124 is pivotally secured within cutout 113 by pivot pin 124a supported within first openings 111a, 113a in respective cutout 111 and cover plate 113. Flange 124 defines a first notch 123a and a second notch 123b. First notch 123a is configured to selectively receive a first lock member 154 of latch mechanism 150. Second notch 123b is configured to operably receive a first end 126a of trigger link 126. Trigger link 126 defines a substantially triangular cross-section having first end 126a and a second end 126b. Although shown having substantially ball-shaped ends 126a, 126b, it is envisioned that first and second ends 126a, 126b may have any suitable shape. A pivot member 128 extends laterally from trigger link 126. As discussed above, pivot member 128 includes the first portion configured to be pivotally received within second opening 111b formed in cutout 111 of base member 110 and the second portion configured to be pivotally received within second opening 113b formed in cover plate 113.

Figure 2:
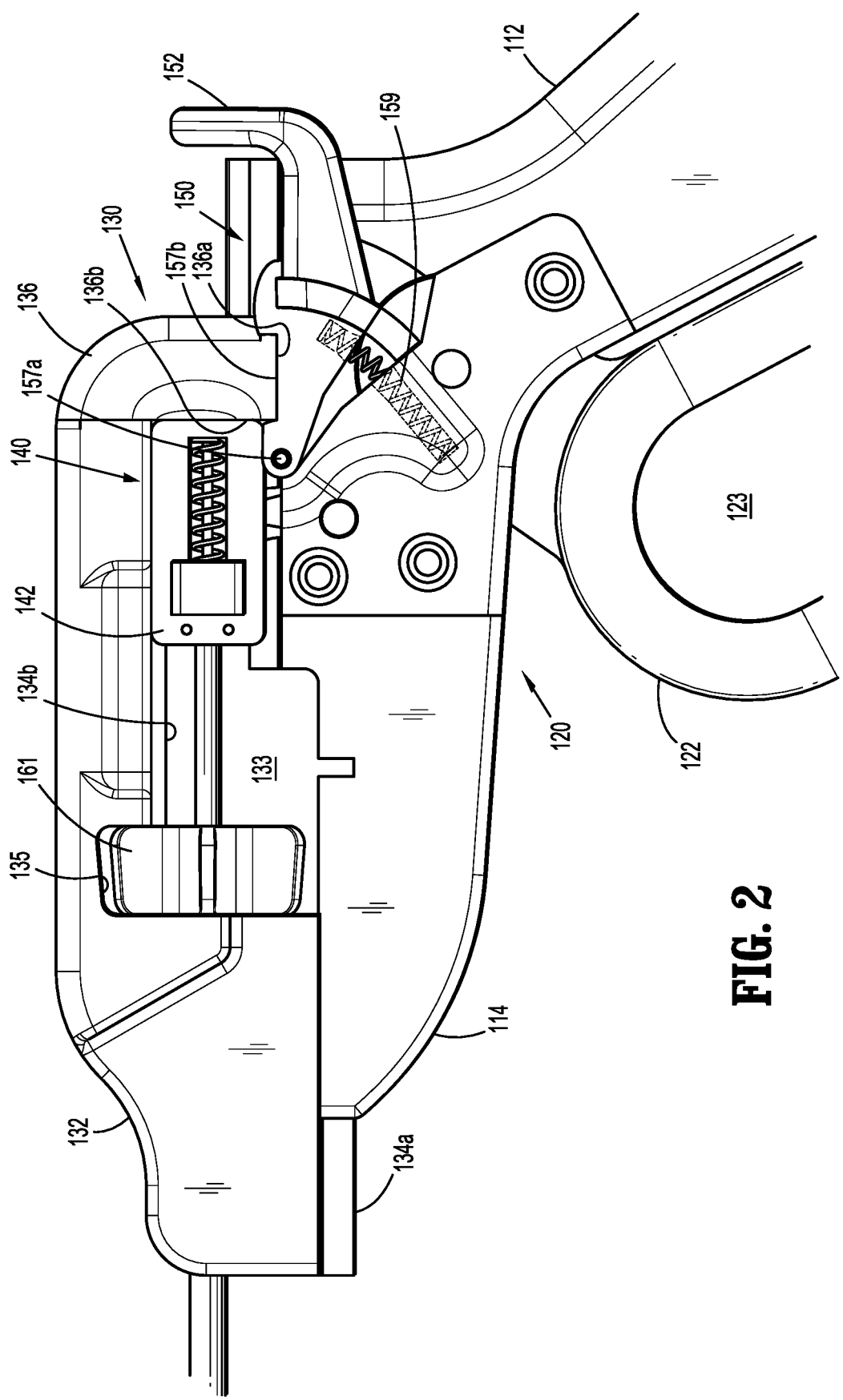
FIG. 2 is an enlarged side view of a portion of an actuation assembly of the endoscopic instrument shown in FIG. 1, in a first or percutaneous position.
Figure 3:
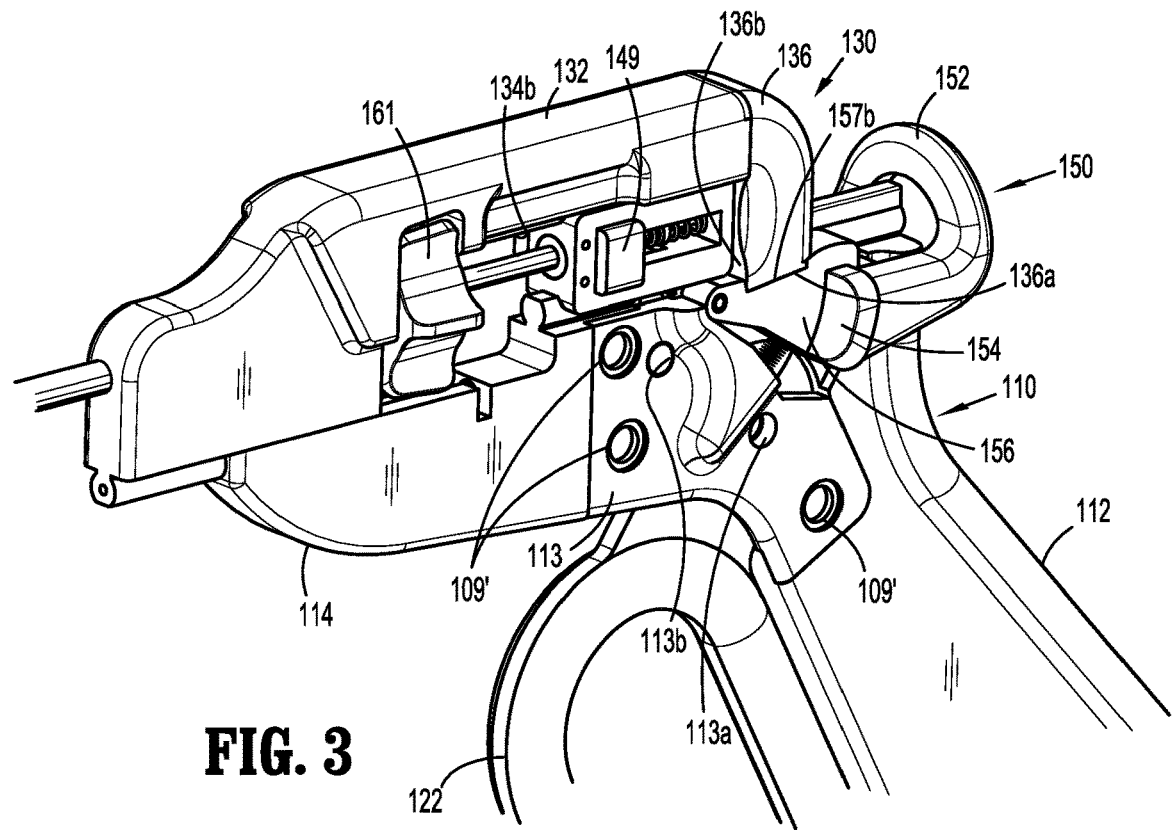
FIG. 3 is a perspective first side view of the portion of the actuation assembly shown in FIG. 2, in the first or percutaneous position.
Figure 4:
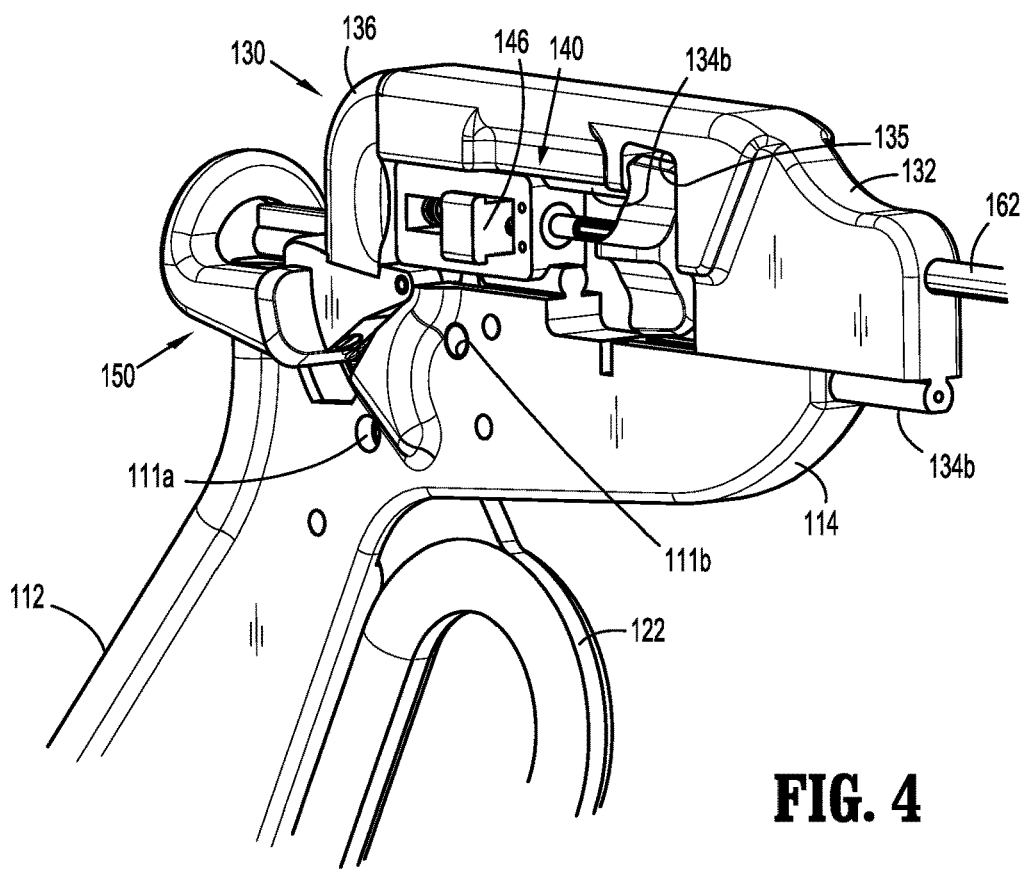
FIG. 4 is a perspective second side view of the portion of the actuation assembly shown in FIG. 2, in the first or percutaneous position.

With reference still to FIGS. 1-5, slider mechanism 130 includes slider 132 and slider extension 136. Slider extension 136 is configured to be secured to a proximal end of slider 132 to define a recess 133 (FIG. 2). Recess 133 is configured to accommodate drive mechanism 140 when slider 132 and slider extension 136 are secured to distal extension 114 of handle assembly 104. Although shown as separate members, it is envisioned that slider 132 and extension 136 may be integrally formed. A first rail 134a extends longitudinally along a distal portion of slider 132. First rail 134a is configured to be received within channel 115 defined by extension 114 of handle assembly 104. Although shown with first rail 124a being formed on slider 132 and channel 115 being defined by distal extension 114, it is envisioned that distal extension 114 may instead include a first rail and slider 132 may define a channel. A second rail 134b extends longitudinally along a proximal portion of slider 132. Second rail 134b is configured to be received within a groove 142a formed in drive box 142 of drive mechanism 140. Receipt of second rail 134 within channel 115 permits longitudinal movement of slider extension 136. Slider 132 defines a notch 135 to accommodate a rotation knob 161 of connection mechanism 160. Slider 132 further defines a bore 137 extending longitudinally through a distal portion of slider 132 configured to operably receive connection mechanism 160.

Still referring to FIGS. 1-5, slider extension 136 defines a channel 139a extending along a bottom surface 136a thereof configured to receive first rail 116 formed on distal extension 114 of handle assembly 104. Receipt of first rail 116 within channel 139a permits longitudinal movement of slider extension 136 relative to distal extension 114. Accordingly, when slider extension 136 is affixed to slider 132 and first rail 134a of slider 132 is received within channel 115 of distal extension 114 and first rail 116 of distal extension 114 is received within channel 139a of slider 132, slider mechanism 130 is longitudinally positionable relative to distal extension 114. As discussed above, channel 115 is configured to receive spring 115a. Spring 115a is configured to bias slider mechanism 130 distally. Slider extension 136 further defines a bore 139 configured to securely retain a proximal end of center rod 168 of connection mechanism 160.

With reference now to FIGS. 5, 11, and 13, drive mechanism 140 includes a drive box 142 and a button member 146. Drive box 142 defines a pair of grooves 142a, 142b formed on top and bottom surfaces, respectively, thereof extending the length drive box 142. As noted above, groove 142b is configured to receive second rail 118 formed on distal extension 114 of base portion 110 and groove 142a is configured to receive first rail 134a formed on slider 132 of slider mechanism 130. Drive box 142 further includes a longitudinal bore 141 extending longitudinally therethrough. A first or proximal section 141a of bore 141 includes a first diameter configured to slidably receive center rod 168 of connection mechanism 160 therethrough. A second or middle section 141b of bore 141 includes a second diameter configured to slidably receive an annular flange 167 formed on a proximal end of inner tube 166 of connection mechanism 160 and a spring 148. A third or distal section 141c of bore 141 includes a third diameter configured to securely receive an annular flange 165 formed on a proximal end of center tube 164 of connection mechanism 160. Drive box 142 further defines an opening 143 extending laterally therethrough along the length thereof. A first section 143a of opening 143 is configured to accommodate the receipt of spring 148 within second section 141b of bore 141. A second section 143b of opening 143 is configured to slidably receive button member 146 therethrough. Drive box 142 also includes an opening 145a in a bottom surface thereof and a pair of openings 145b extending laterally therethrough. Opening 145a in the bottom surface of drive box 142 is configured for operative reception of second end 126b of trigger link 128 of trigger mechanism 120. Each of openings 145b extends laterally through drive box 142 and is configured to receive a pin 145' for securing annular flange 165 of center tube 164 to drive box 142.

With particular reference to FIG. 13, button member 146 of drive mechanism 130 includes a substantially elongate body defining a slot 147. Slot 147 is defined by a first section 147a of button member 146 configured to securely engage inner tube 166 of connector mechanism 160 and a second section 147b of button member 147b configured to permit passage of annular flange 165 formed on the proximal end of inner tube 154 through button member 146. Button member 146 includes an enlarged first end 146a and a second end 146b configured to be received through distal section 143*b* of opening 143 in drive box 142. A cap member 149 is configured to be secured to second end 146*b* of button member 146 once distal section 146*b* has been received through distal section 143*b* of opening 143 to secure button member 146 to drive box 142. Each of enlarged first end 146*a* and cap member 149 are configured for engagement by a user to permit lateral movement of button member 146 relative to drive box 142.

Turing briefly to FIGS. 11 and 14, when drive mechanism 140 is in a first or unlocked condition, inner tube 166 is received through second section 147*b* of slot 147 formed in button member 146. In this manner, inner tube 166 is permitted to move longitudinally relative to button member 146 and drive box 142. Spring 148 engages flange 167 of inner tube 166 thereby biasing inner tube 166 distally. As shown, the bias provided by spring 148 against flange 167 of inner tube 166 positions fingers 166*a* of inner tube 166 distally of the distal end of center tube 164. With reference now to FIG. 25, in a second or locked condition, after flange 167 (FIG. 23) of inner tube 166 has overcome the bias of spring 148 (FIG. 23) to cause flange 167 to be disposed proximal of button member 146, button member 146 is moved laterally, as indicated by arrow "E", to position button member 146 such that inner tube 166 is received within first section 147*a* of slot 147 formed in button member 146, thereby securing inner tube 166 relative to button member 146 and drive box 142. Returning button member 146 to its original position (FIG. 14) unlocks drive mechanism 140, thereby allowing longitudinal movement of inner tube 166 relative to drive box 142.

With reference back to FIG. 5, latch mechanism 150 includes a latch lever 152, a first lock member 154, a pair of second lock members 156, and a pivot member 158. Latch lever 152 is configured for operable engagement by the user. A distal end of latch lever 152 is secured to first lock member 154 in any suitable manner, i.e., adhesive. First lock member 154 defines a substantially planar member configured to be selectively received within notch 111*c* formed in base member 110 and within first notch 123*a* formed in flange 124 extending from trigger 122 of trigger mechanism 120. First lock member 154 is secured to each of second lock members 156 in any suitable manner, i.e., adhesive. Second lock members 156 each include an opening 157*a* and a cutout 157*b*. Openings 157*a* are each configured to receive an end of pivot member 158. Cutout 157*b* is configured to be selectively received about bottom surface 136*a* of slider extension 136 of slider mechanisms 130. Second lock members 156 each include a proximal facing surface 156*a* configured to selectively engage slider extension 136. Latch mechanism 150 further includes a pair of springs 159 configured to bias second lock members 156 upward. Although shown as separate members, it is envisioned that latch lever 152, first lock member 154 and second lock members may be integrally formed.

Figure 17:
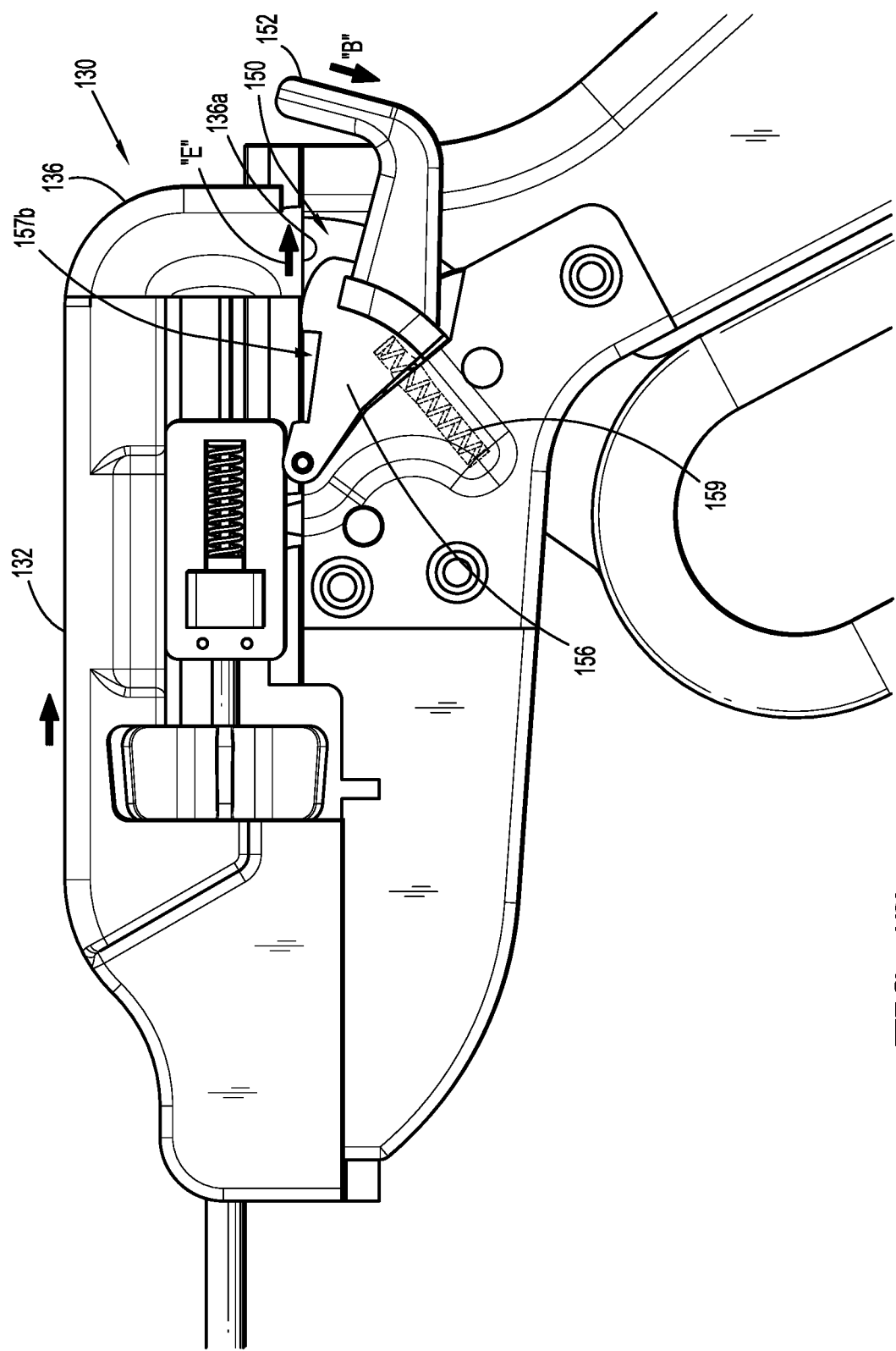
FIG. 17 is a side view of the portion of the actuation assembly shown in FIG. 2, in a second or intermediate position.
Figure 18:
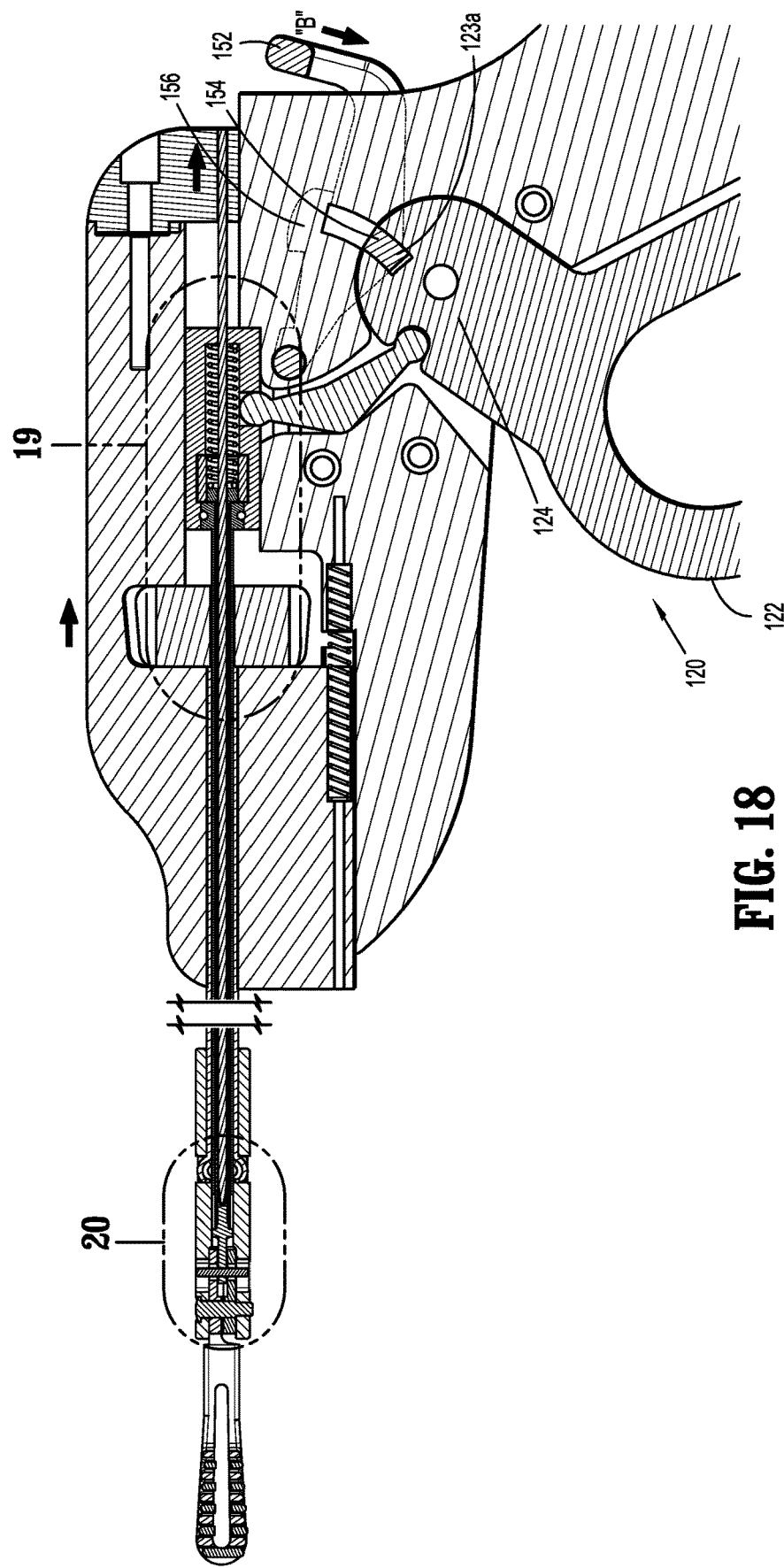
FIG. 18 is a cross-sectional side view of the portion of the actuation assembly shown in FIG. 17.
Figure 19:
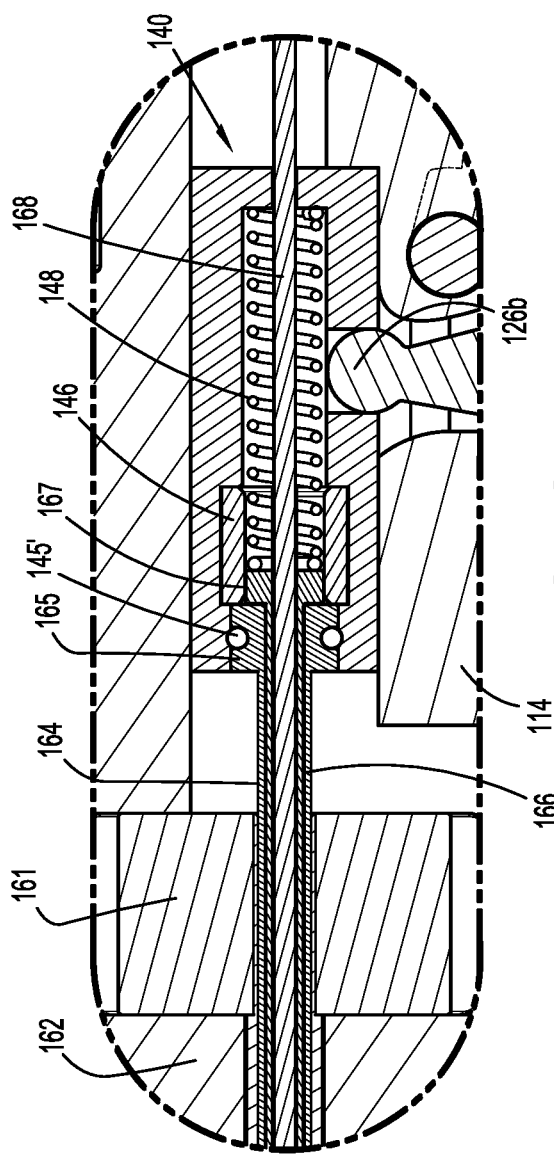
FIG. 19 is an enlarged view of portion 19 shown in FIG. 18.
Figure 20:
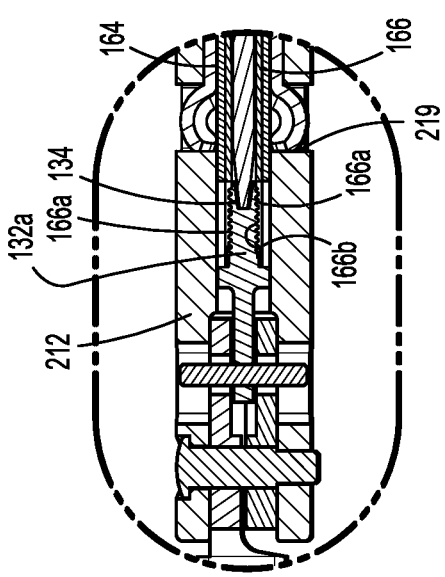
FIG. 20 is an enlarged view of portion 20 shown in FIG. 18.
Figure 21:
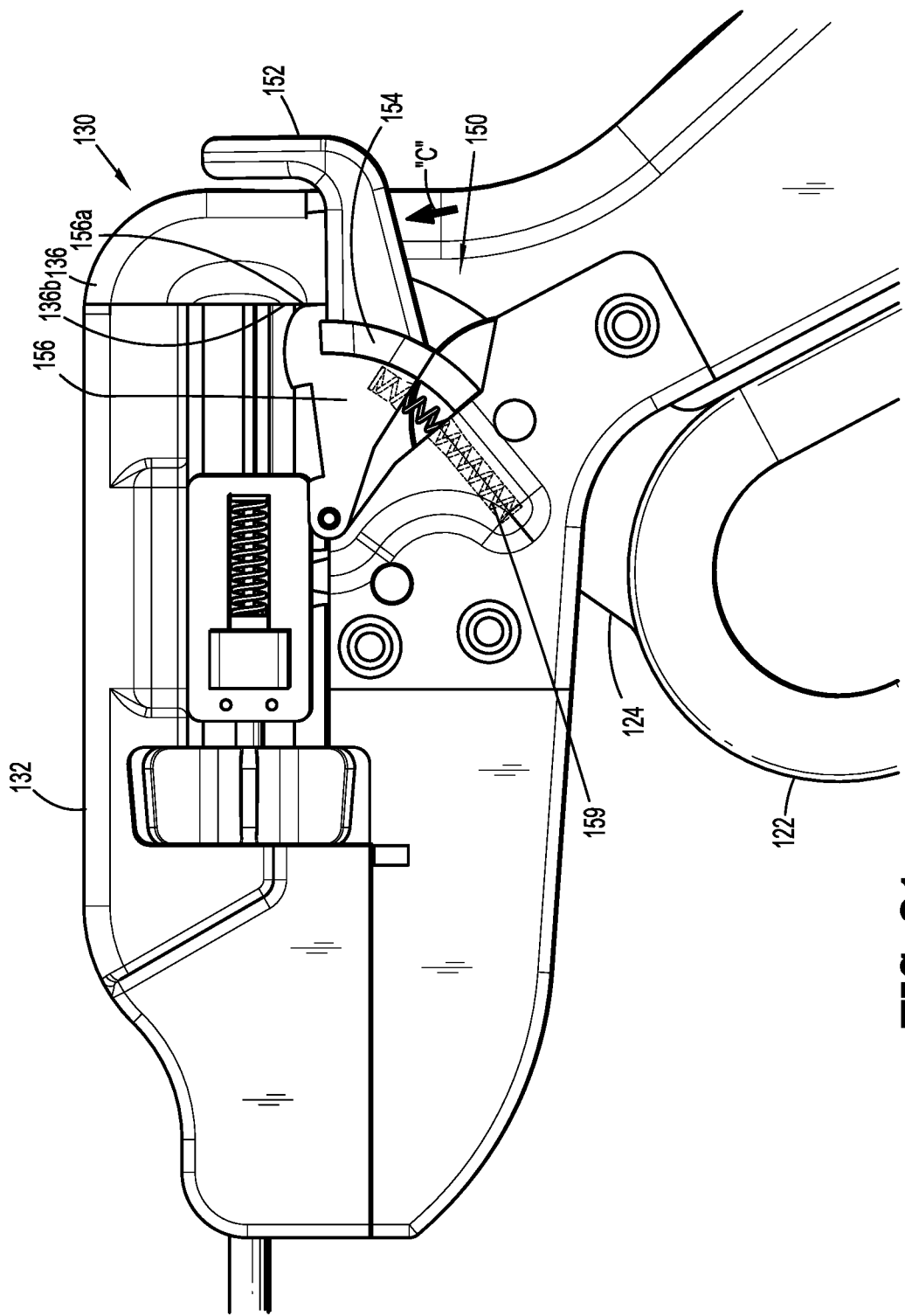
FIG. 21 is a side view of the portion of the actuation assembly shown in FIG. 2, in a third or engaged position.
Figure 22:
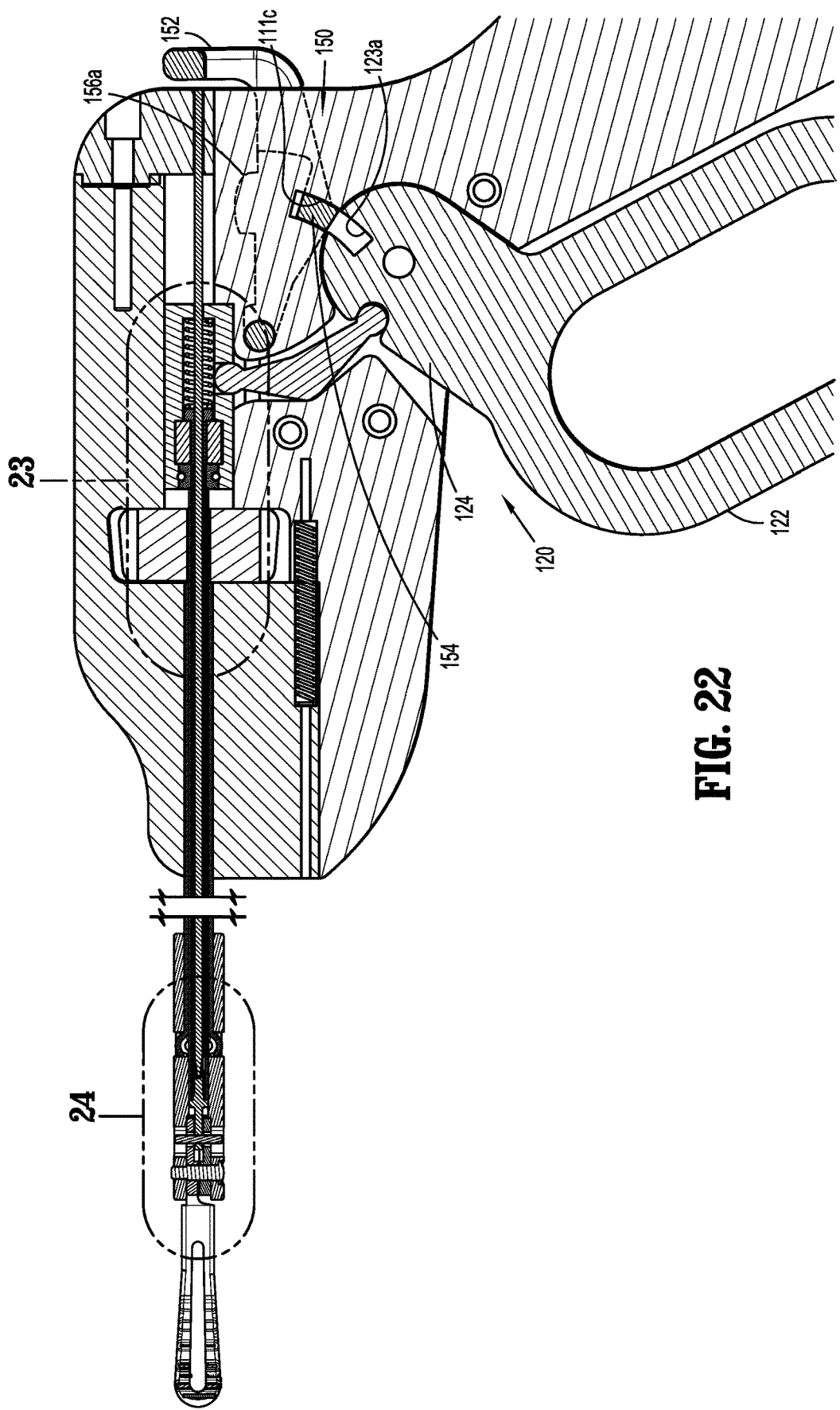
FIG. 22 is a cross-sectional view of the portion of the actuation assembly shown in FIG. 21.
Figure 26:
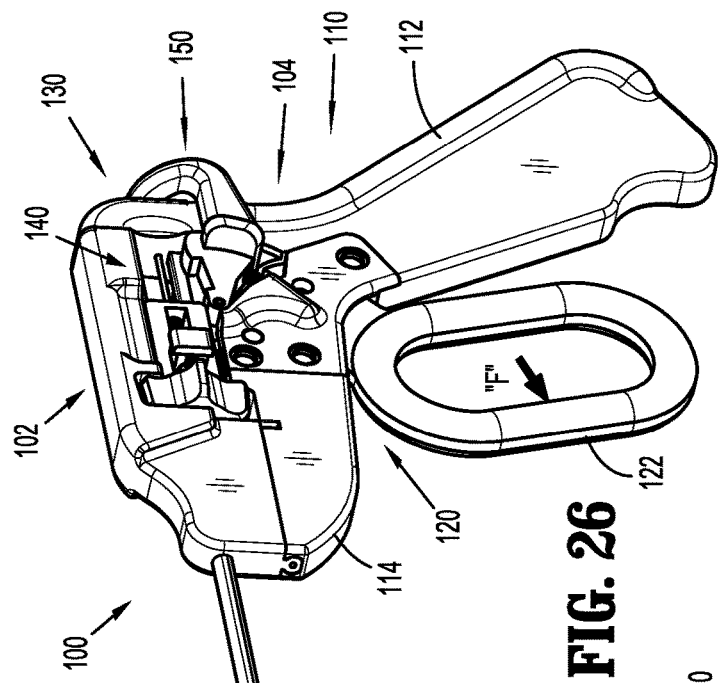
FIG. 26 is a perspective view of the endoscopic instrument shown in FIG. 1, in an engaged position and with the jaw assembly of the end effector in an open position.

Latch mechanism 150 is moveable about pivot member 158 between multiple locking positions. In a first locking position, as shown in FIG. 2, second lock members 156 are biased upward by springs 159 such that bottom surface 136*a* of slider extensions 136 of slider mechanism 130 is received within cutouts 157*b*. As discussed above, receipt of bottom surface 136*a* of slider extension 136 within cutouts 157*b* prevents retraction of slider mechanism 130. In a second locking position, as shown in FIGS. 17 and 18, latch lever 152 is pushed downward, as indicated by arrow "B", against the bias of springs 159 to move second lock members 156 from about bottom surface 136*a* of slider extension 136. Latch mechanism 150 is maintained in the second position through engagement of second lock members 156 with bottom surface 136*a* of slider extension 136. In the second locking position, first lock member 154 is received within first notch 123*a* formed in flange 124 extending from trigger 122 of trigger mechanism 120. Receipt of first lock member 154 in first notch 123*a* prevents movement of trigger 122. In a third locking position, as shown in FIGS. 21 and 22, complete retraction of slider mechanism 130 allows springs 159 to bias second lock members 156 upward, as indicated by arrow "C". As such, proximal facing surfaces 156*a* of second lock members 156 engage a distal surface 136*b* of slider extension 136 to maintain slider mechanism 130 in the completely retracted position. The upward movement of second lock members 156 also withdraws first lock member 154 from within first notch 123*a* formed in flange 124 extending from trigger 122, thereby releasing trigger 122.

Figure 6:
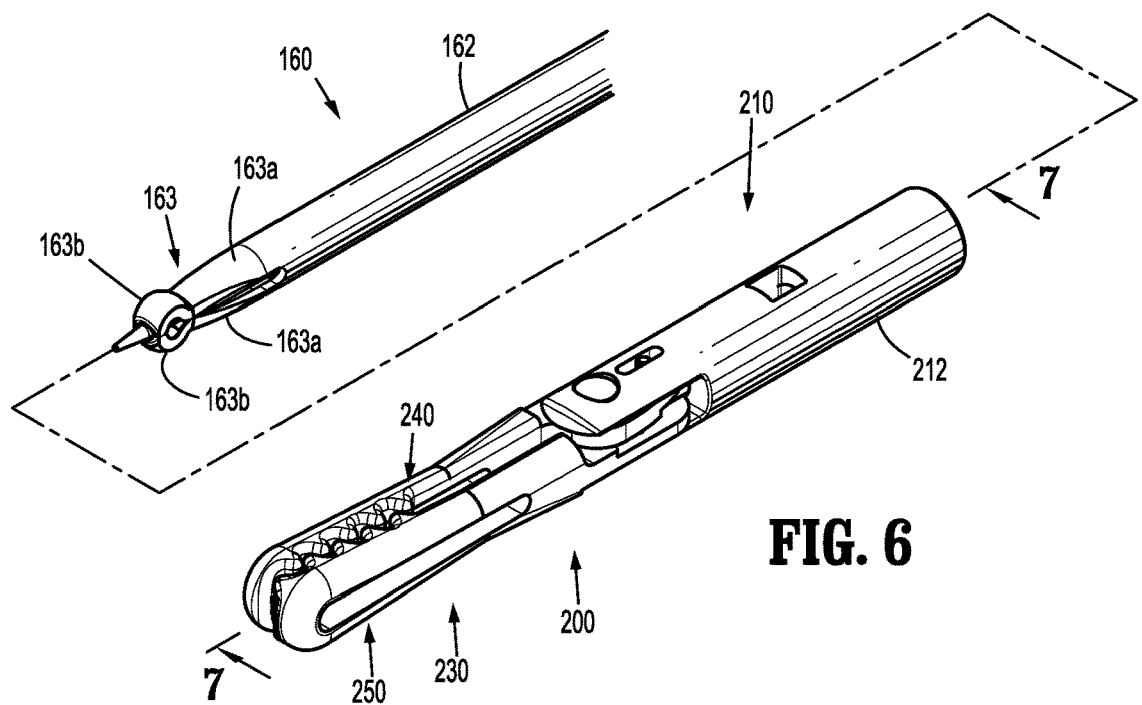
FIG. 6 is a perspective view of the distal end of a connection mechanism of the actuation assembly shown in FIG. 2 and an end effector of the endoscopic instrument shown in FIG. 1.
Figure 8:
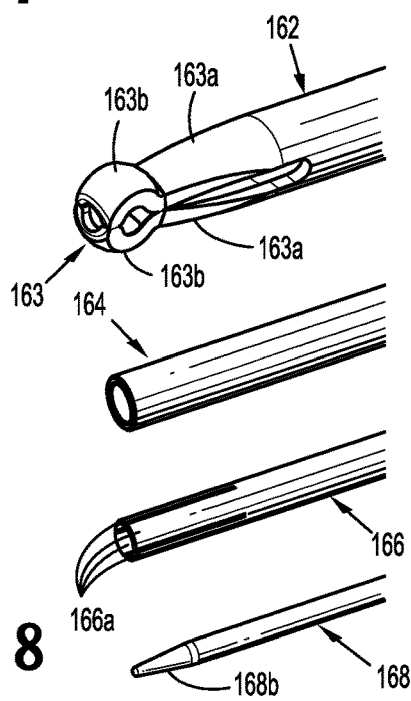
FIG. 8 is an exploded perspective view of the distal end of the connection mechanism shown in FIG. 6.

With reference now to FIGS. 5, 6 and 8, shaft assembly 106 includes a connection mechanism 160 having a first or outer tube 162, a second or center tube 164, a third or inner tube 166, and a center rod 168. Outer tube 162 is configured to fixedly support rotation knob 161 on a proximal end and includes collet 163 formed on a distal end. Rotation knob 161 operates to secure outer tube 162 to slider 132 of slider mechanism 130 and allows a user to cause the rotation of outer tube 162 along a longitudinal axis "x" (FIG. 1). As will become apparent below, because end effector 200 is rotationally secured to outer tube 162 of connection mechanism 160, rotation of outer tube 162 about longitudinal axis "x" causes rotation of end effector 200 about longitudinal axis "x". Collet 163 includes a pair of arms 163*a*. As shown, each arm 163*a* includes a rounded protrusion 163*b*. Arms 163*a* are configured to flex outwardly upon receipt of center tube 164 therethrough. Although shown including a pair of arms 163*a*, it is envisioned that collet 163 may include more than two arms 163*a*.

Center tube 164 is configured to be received within outer tube 162 and includes flange 165 on a distal end thereof. As discussed above, flange 165 operates to secure center tube 164 to drive box 142 of drive mechanism 140. Inner tube 166 is configured to be received within center tube 164. Inner tube 166 includes a plurality of fingers 166*a* on a distal end thereof configured to permit the expansion of the distal end of inner tube 166 to facilitate attachment of inner tube 166 with a link member 232 of jaw assembly 230 of end effector 200. Inner surfaces of fingers 166*a* include ridges 162*b* (FIG. 12) configured to engage corresponding ridges 234 (FIG. 9) formed on link member 232 of end effector 200. As discussed above, the proximal end of inner tube 166 includes flange 167 configured for selective engagement with button member 146 of drive mechanism 140. As seen in FIGS. 11 and 12, inner tube 166 has a length such that when flange 167 is biased to a distal-most position by spring 148, fingers 166*a* formed on the distal end of inner tube 166 are disposed distally of the distal end of center tube 164. In this manner, and as will be discussed in further detail below, fingers 166*a* of inner tube 166 engage proximal end 232*a* of link member 232 prior to engagement of link member 232 by center tube 164. Center rod 168 includes a proximal end configure to be secured within bore 139 of slider extension 136 of slider mechanism 130 and a pointed distal end 168*b*.

As noted above, since outer tube 162 of connection mechanism 160 is secured to slider 132 of slider mechanism 130 and center rod 168 of connection mechanism 160 is secured to slider extension 136 of slider mechanism 130, and each of slider 132 and slider extensions 136 are longitudinally fixed relative to each other, each of outer tube 162 and center rod 168 are also longitudinally fixed relative to each other. Accordingly, pointed distal end 168b of center rod 168 is always disposed distally of collet 163. As also noted above, center tube 164 is longitudinally fixed relative to drive box 142 and inner tube 166 is selectively longitudinally fixed relative to drive box 142 through operation of button member 146.

Figure 7:
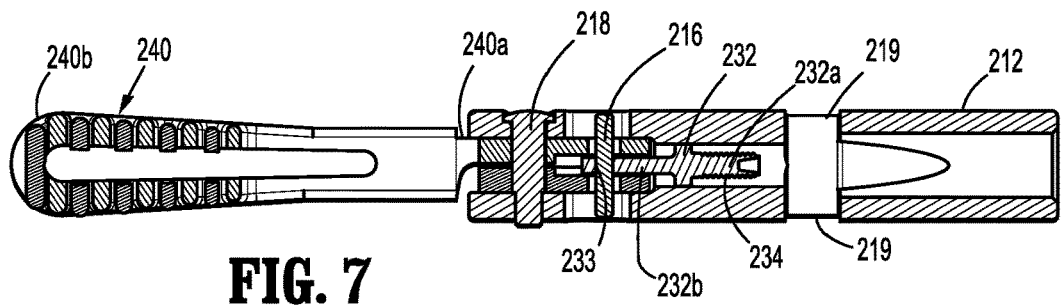
FIG. 7 is a cross-sectional view of the end effector shown in FIG. 6 taken along line 7-7.
Figure 9:
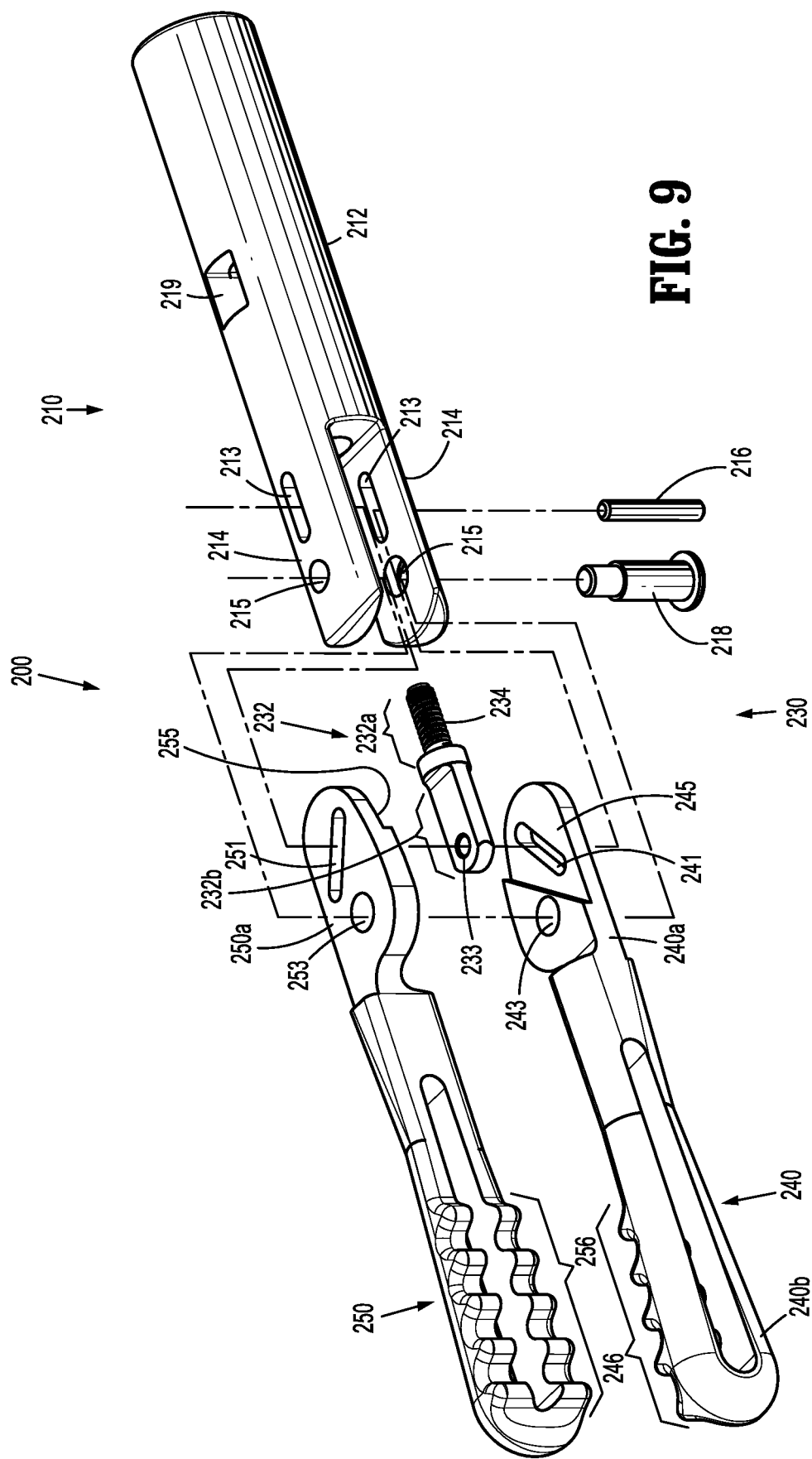
FIG. 9 is an exploded perspective view of the end effector shown in FIG. 6.
Figure 10:
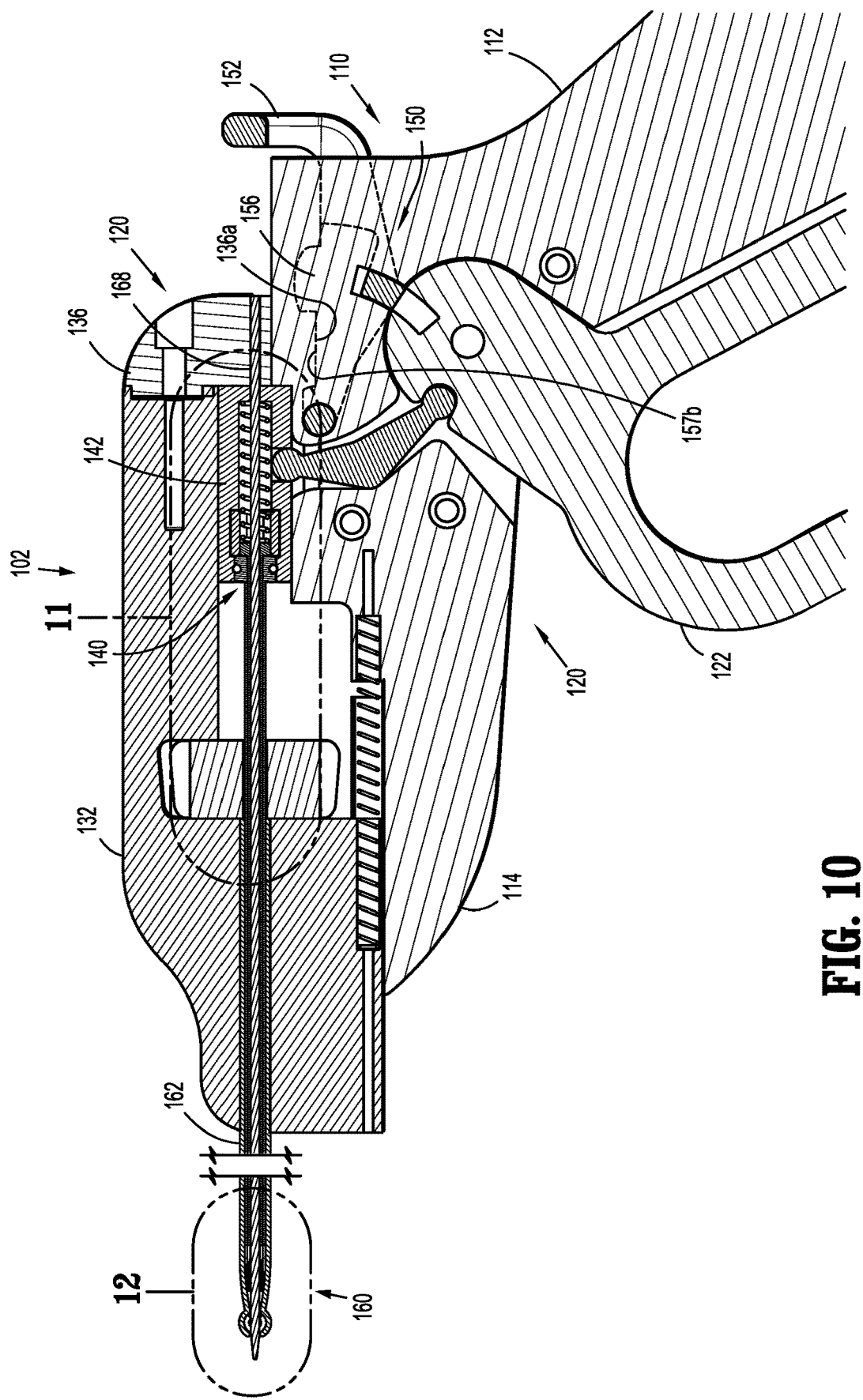
FIG. 10 is a cross-sectional view taken along line 10-10 shown in FIG. 1.

With reference now to FIGS. 6, 7 and 9, end effector 200 includes a connection assembly 210 and a jaw assembly 230. Connection assembly 210 includes a tubular body 212 having a pair of distal supports 214 extending distally therefrom for operable engagement with jaw assembly 230. Each arm 214 includes a slot 213 and an opening 215. Slot 213 is configured to receive a connecting pin 216 and opening 215 is configured to receive a pivot pin 218. Tubular body 212 defines a pair of cutouts 219 extending therethrough configured to receive protrusions 163b (FIG. 8) of arms 163a of collet 163 formed on the distal end of outer tube 162 when arms 163a are in an outwardly flexed condition. Cutouts 219 correspond in number and location to arms 163a of collet 163. As discussed above, it is envisioned that collet 163 may have more than two arms 163a, therefore tubular body 212 may include more than two cutouts 219.

Figure 15:
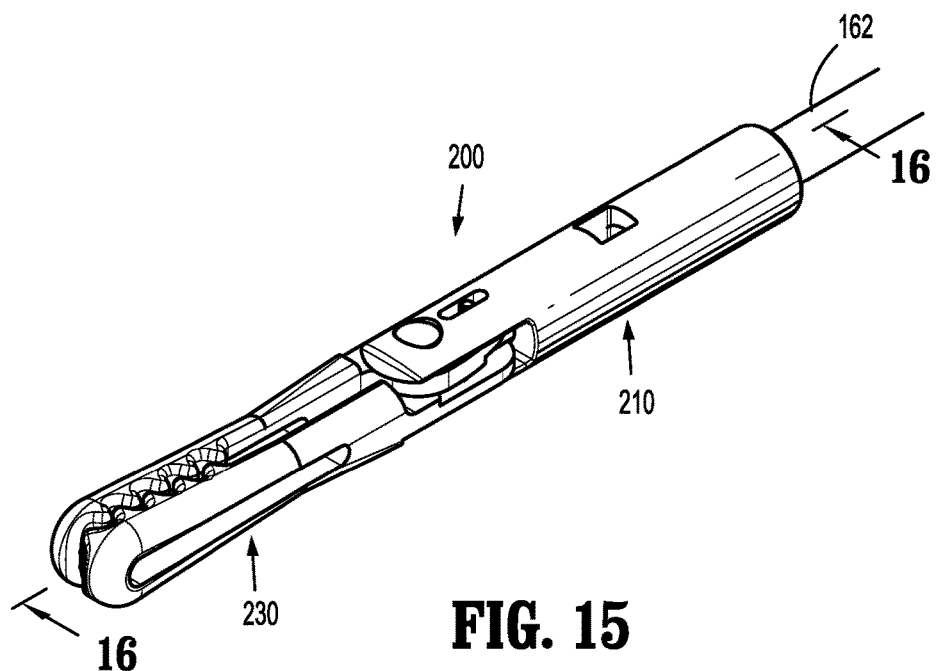
FIG. 15 is a perspective view of the end effector and the distal end of the connection mechanism shown in FIG. 6, upon receipt of the distal end of the connection mechanism within the end effector shown in FIG. 6.
Figure 27:
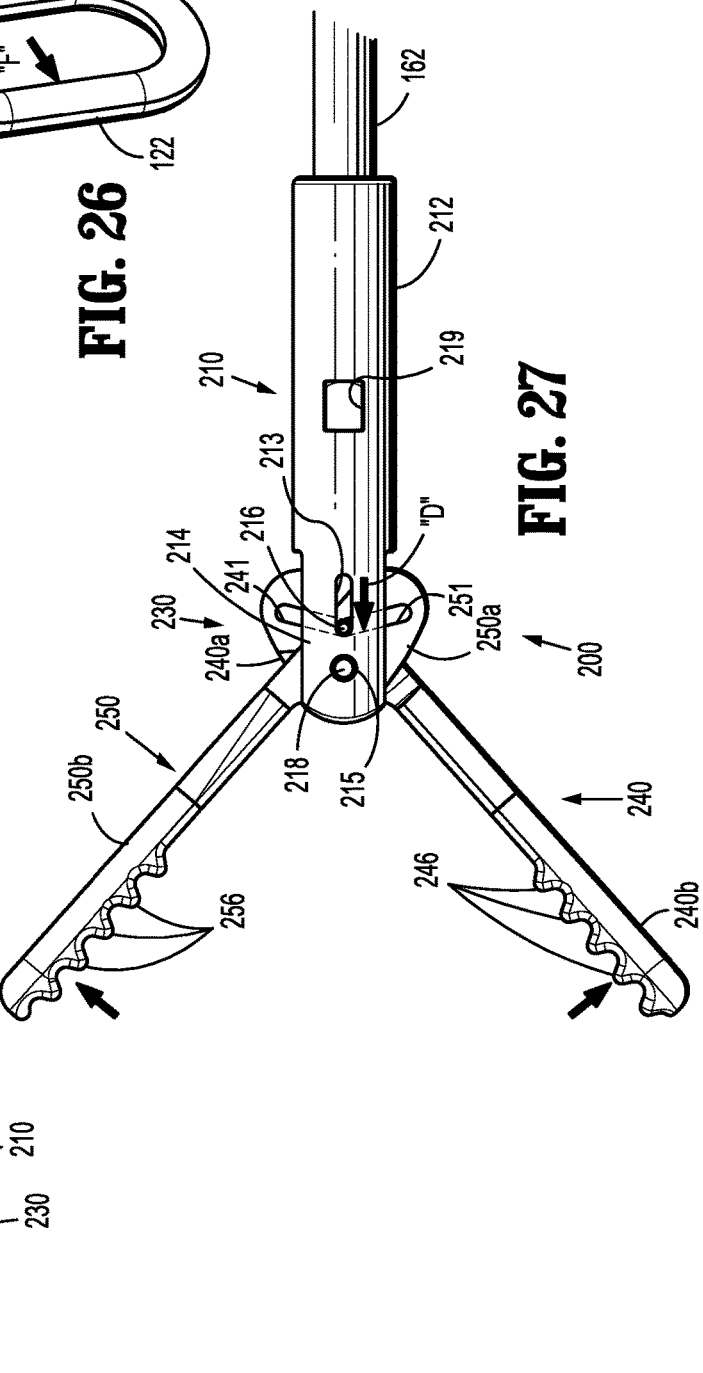
FIG. 27 is an enlarged view of the jaw assembly shown in FIG. 26, in the open position.
Figure 31:
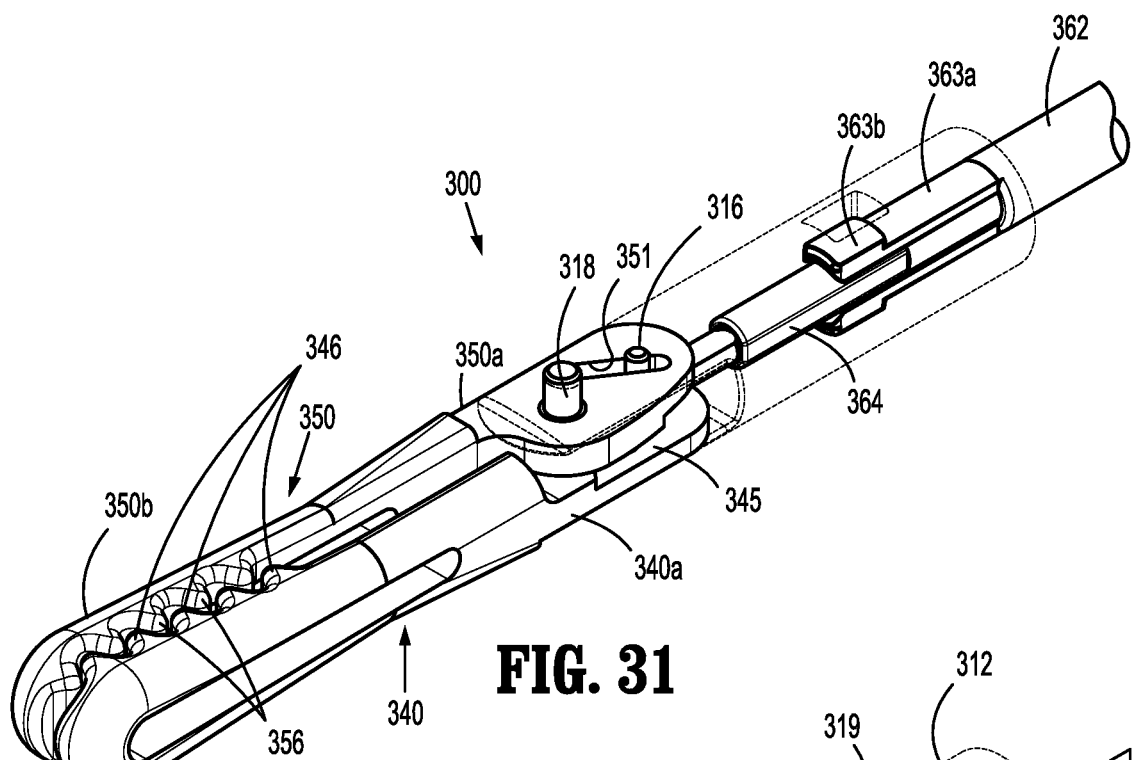
FIG. 31 is a perspective view of an end effector and a distal end of a connection mechanism according to another embodiment of the present disclosure, the end effector being received on the distal end of the connection mechanism.
Figure 32:
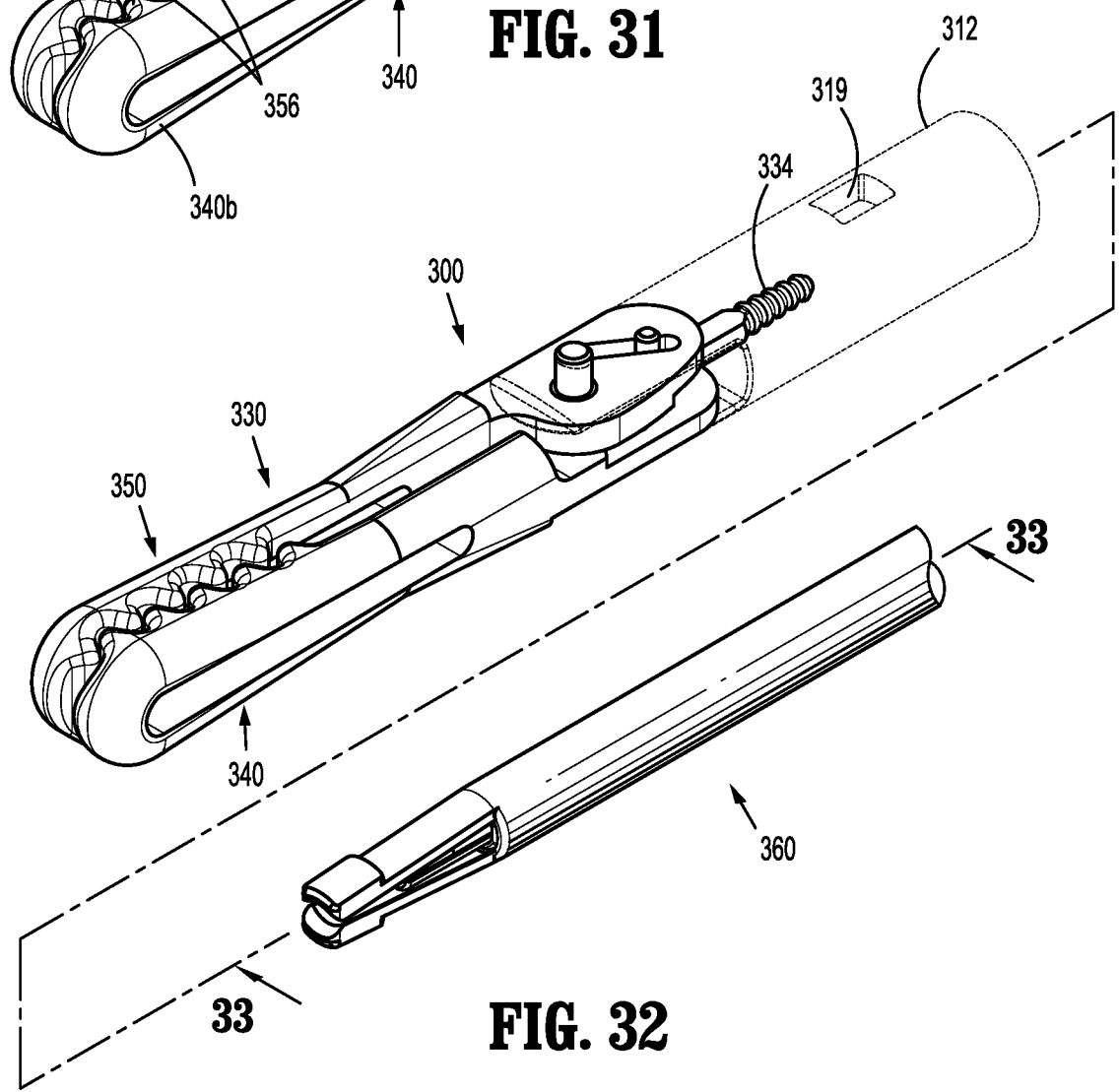
FIG. 32 is a perspective view of the end effector and the distal end of the connection mechanism of FIG. 31, the end effector being separated from the distal end of the connection mechanism.

With reference still to FIGS. 6, 7 and 9, jaw assembly 230 includes a link member 232, a first jaw member 240, and a second jaw member 250. Link member 232 includes a proximal end 232a having a plurality of ridges 234 and a substantially planar distal end 232b defining an opening 233. Each of first and second jaw members 240, 250 include a proximal end 240a, 250a having a diagonal slot 241, 251, respectively, and an opening 243, 253, respectively. A cutout 245, 255 on proximal end 240a, 250a, respectively, of each of respective first and second jaw members 240, 250 is configured to accommodate distal end 232b of link member 232. A distal end 240b of first jaw member 240 includes a plurality of teeth 246. A distal end 250b of second jaw member 250 includes a plurality of teeth 256 configured to mesh with teeth 246 of first jaw member 240 when first and second jaw members 240, 250 are in a closed position, i.e., engage one another (FIG. 15). First and second jaw members 240, 250 are pivotally secured to distal supports 214 of tubular member 210 by pivot pin 218 received through openings 243, 253 of respective first and second jaw members 240, 250 and through openings 215 in distal supports 214. Connecting pin 216 is received through diagonal slots 241, 251 of respective first and second jaw members 240, 250, through slots 213 formed in distal supports 214, and through opening 233 formed in link member 232. Turning briefly to FIG. 27, jaw assembly 230 is configured such that distal advancement of connecting pin 216 through slots 213 of distal supports 214, as indicated by arrows "D", causes first and second jaw members 240, 250 of jaw assembly 230 to move to an open position.

The operation of endoscopic instrument 100 will now be described with reference to FIGS. 1-30. As shown in FIGS. 1-4 and 10-16, actuation assembly 102 is in a first or percutaneous position. In the percutaneous position, slider 132 and slider extension 136 of slider mechanism 130 are supported on extension 114 of base member 110 in an advanced or distal-most position. While in the percutaneous position, latch mechanism 150 operates to retain slider 132 and slider extension 136 in the advance position. In particular, second lock members 156 of latch mechanism 150 are biased upward by springs 159 to capture bottom surface 136a of slider extension 136 within cutouts 157b of second lock members 156.

In the percutaneous position, trigger 122 of trigger mechanism 120 and drive box 142 of drive mechanism 140 are in a retracted position. As discussed above, since outer tube 162 of connection mechanism 160 is secured to slider 132 of slider mechanism 130 and center rod 168 is secured to slider extension 136 and slider extension 136 is fixed relative to slider 132 outer tube 162 and center rod 168 are fixed relative to each other. As seen in FIG. 12, the advanced position of slider mechanism 130 relative to the retracted position of drive mechanism 140 results in the distal ends of center tube 164 and inner tube 166, respectively, being disposed proximally of collet 163 of outer tube 162. In the percutaneous position, a distal end of connection mechanism 160 is capable of penetrating through tissue of a patient and into a body cavity. Penetration through tissue may be accomplished through an incision formed in the tissue or through a port assembly previously received through the tissue. Alternatively, pointed distal end 168b of center rod 168 may be sufficiently sharp to facilitate the unaided piercing of the tissue.

Figure 16:
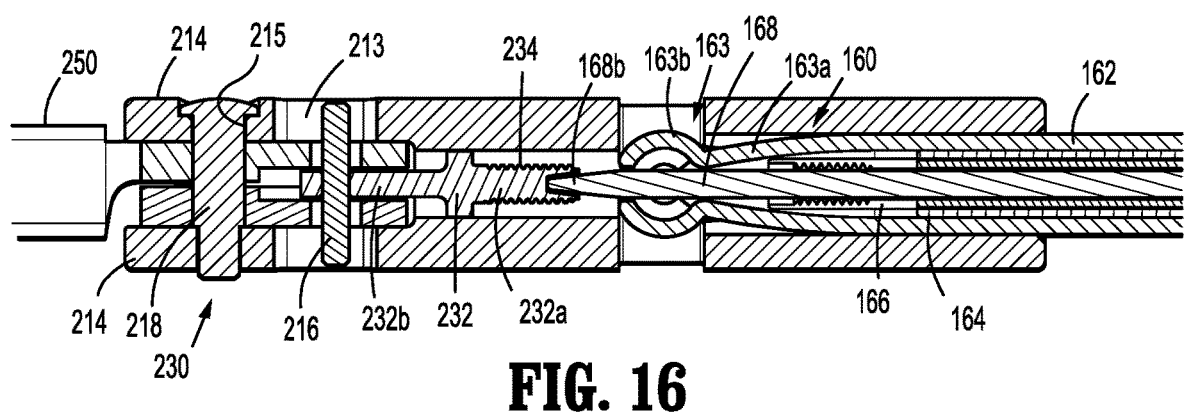
FIG. 16 is a cross-sectional view taken along 16-16 shown in FIG. 15.
Figure 71:
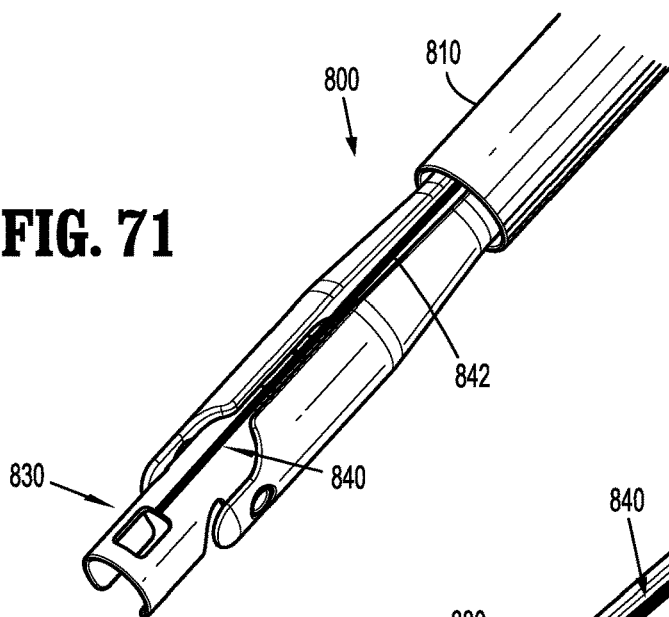
FIG. 71 is a perspective view of a holder according to an embodiment of the present disclosure, in a first or insertion position.

With particular reference now to FIGS. 15 and 16, once the distal end of connection mechanism 160 has been received within a body cavity, connection mechanism 160 may be secured to end effector 200. More specifically, the distal end connection mechanism 160 is received within tubular body 212 of connector assembly 210 such that pointed distal end 168b of center rod 168 engages link member 232 of jaw assembly 230 and collet 163 is aligned with cutouts 219. The positioning of end effector 200 within the body cavity and the manipulation of end effector 200 during attachment to connector mechanism 160 may be facilitated by a holder 800 (FIG. 71), as will be discussed in detail below, or other gripping instrument.

Turning now to FIGS. 17-20, actuation assembly 102 is shown in a second or intermediate position. In the intermediate position, latch member 152 is pushed downward against the bias of springs 159, in the direction indicated by arrow "B", to disengage second lock members 156 from bottom surface 136a of slider extension 136 of slider mechanism 130. By disengaging slider extension 136, slider 132 and slider extension 136 are permitted to be retracted proximally, in the direction indicated by arrow "E". The downward movement of latch member 152 causes first lock member 154 to be received within first notch 123a (FIG. 18) formed in flange 124 extending from trigger 122. In this manner, trigger 122 is prevented from being moved. Latch member 152 is maintained in the downward position by engagement of second lock members 156 with slider extension 136.

Still referring to FIGS. 17-20, retraction of slider 132 and slider extension 136 of slider mechanism 130 relative to drive box 142 of drive mechanism 140 causes retraction of outer tube 162 and center rod 168 relative to center tube 164. The retraction of outer tube 162 relative to center tube 164 results in the movement of the distal end of center tube 164 through collet 163 of outer tube 162. As discussed about, receipt of center tube 164 through collet 163 of outer tube 162 causes arms 163a of collet 163 to flex outwardly. As arms 163a are flexed outwardly, protrusions 163b formed on arms 163 are received within cutouts 219 of tubular body 212, thereby securing end effector 200 to shaft assembly 106.

Once protrusions 163b formed on arms 163a of collet 163 are received within cutouts 219 of tubular body 212 to secure end effector 200 to shaft assembly 106, continued retraction of outer tube 162 relative to center tube 164 causes retraction of end effector 200 relative to center tube 164. Since inner tube 166 is maintained relative to center tube 164 by spring 148, retraction of end effector 200 relative to center tube 164 causes corresponding retraction of end effector 200 relative to inner tube 166. As noted above, the distal end of inner tube 166 is maintained distally of a distal end of center tube 164 through the bias of spring 148. As such, as end effector 200 is retracted relative to center tube 164, fingers 166a of inner tube 166 engage proximal end 232a of link member 232 and are flexed outwardly to accommodate reception of fingers 166a about proximal end 232a. Once fingers 166a of inner tube 166 are completely received about proximal end 232a of link member 232, ridges 166b formed on fingers 166a engage ridges 134 formed on proximal end 232a and fingers 166a returned to a pre-flexed condition.

With reference now to FIGS. 21-25, actuation assembly 102 is shown in an engaged position. Once slider 132 and slider extension 136 have been completely retracted, second lock members 156 of latch mechanism 150 are no longer retained in the downward position by slider extension 136. As such, springs 159 bias second lock members 156 upward. As discussed above, second lock members 156 each include a proximal facing surface 156a that engages slider extension 136 when slider mechanism 130 is in a fully retracted position. In this manner, slider mechanism 130 is prevented from advancing, i.e., returning to the pre-retracted position (FIG. 1), while latch lever 152 is in the upward position. Upward movement of second lock members 156 causes first lock member 154 to be removed from within first notch 123a formed in flange 122 of trigger 120, thereby allowing movement of trigger 122.

As discussed above, during movement of slider mechanism 130 to the intermediate position, fingers 166a of inner tube 166 engage and are received about proximal end 232a of link member 232. Once fingers 166a of inner tube 166 are complete received about proximal end 232a, continued retraction of slider mechanism 130 causes continued retraction of end effector 200 relative to center tube 164; however, because inner tube 166 is secured to link member 232, retraction of end effector 200 relative to center tube 164 overcomes the bias provided by spring 148 to cause the retraction of inner tube 166 relative to center tube 164. As seen in FIG. 23, the retraction of inner tube 166 relative to center tube 164 causes flange 167 formed on the proximal end of inner tube 166 to be moved proximally of button member 146. At the same time, the distal end of center tube 164 is positioned about fingers 166a of inner tube 166. The positioning of center tube 164 about inner tube 166 prevents splaying of fingers 166a of inner tube 166, thereby ensuring fingers 166a of inner tube 166 remains attached to proximal end 232a of link member 232.

With reference now to FIGS. 23-25, once distal ends of center tube 164 and inner tube 166 are received about proximal end 232a of link member 232, i.e., upon complete retraction of slider mechanism 130, button member 146 of drive mechanism 140 is moved laterally, as indicated by arrow "E" (FIG. 25), to position button member 146 such that inner tube 166 is received within first section 147a of button member 146 forming slot 147. As discussed above, first section 147a of button member 146 forming slot 147 is configured to engage inner tube 166 such that inner tube 166 is fixed relative to drive box 142. In this manner, advancement and/or retraction of drive box 142 causes corresponding advancement and/or retraction of both center tube 164 and inner tube 166.

Turning now to FIGS. 26-30, once inner tube 166 is secured relative to drive box 142 of drive mechanism 140 endoscopic instrument 100 is ready for use. Movement of trigger 122 of trigger mechanism 120 away from handle portion 112 of base member 110, as indicated by arrow "F", causes opening of jaw assembly 230. In particular, movement of trigger 122 away from handle portion 112 causes trigger link 126 to pivot about pivot member 128 (FIG. 5) thereby causing distal advancement of drive box 142 of drive mechanism 140, as indicated by arrow "G" (FIG. 29). As discussed above, center and inner tubes 164, 166 are fixed relative to drive box 142, thus, distal advancement of drive box 142 results in distal advancement of center and inner tubes 164, 166.

With particular reference to FIGS. 27 and 30, distal advancement of center and inner tubes 164, 166 causes distal advancement of link member 232 of jaw assembly 230 relative to tubular member 212. Distal advancement of link member 232 causes advancement of connecting pin 216, as indicated by arrow "D". As discussed above, connecting pin 216 is received with diagonal slots 241, 251 of respective first and second jaw members 240, 250. As such movement of connecting pin 216 in the distal direction causes first and second jaw members to pivot away from each other. In this manner, movement of trigger 122 away from handle portion 114 of base member 110 causes opening of jaw assembly 230. Conversely, the return of trigger 122 towards handle portion 114 causes first and second jaw members 240, 250 to move towards each other, thereby closing jaw assembly 230. Trigger 122 may be moved towards and away from handle portion 114 as needed to cause the opening and closing of jaw assembly 230.

Once end effector 200 is secured to connection mechanism 160 of actuation assembly 102, endoscopic instrument 100 may be used as a traditional grasper. As noted above, movement of trigger away from and towards handle portion 114 of base member 110 causes opening and closing, respectively, of jaw assembly 230. Jaw assembly 230 may also be rotated about longitudinal axis "x" using rotation knob 161 which is secured to the distal end of outer tube 162.

At any point during a procedure, end effector 200 may be disengaged from connection mechanism 160 of actuation assembly 102 in the reverse manner of attachment. Specifically, trigger 122 is moved towards handle portion 112 to retract drive box 142 to its proximal-most position. Button member 146 is then moved laterally to align second section 147b of slot 147 with inner tube 164 to permit longitudinal movement of inner tube relative to drive box 142. Latch lever 152 is then pushed down to disengage second lock members 156 from slider extension 136 to permit distal advancement of slider mechanism 130. Distal advancement of slider mechanism 130 cause retraction center and inner tubes 164, 166 relative to link member 232 of end effector 200. Initial distal advancement of slider mechanism 130 causes inner tube 166 to disengage from proximal end 232a of link member 232. Continued distal advancement of slider mechanism 130 causes distal ends of center and inner tubes 164, 166 to be retracted distally relative to collet 163 formed on outer tube 162. Retraction of center tube 164 from within collet 163 permits arms 163a of collet 163 to return to non-flexed position, thereby disengaging rounded protrusions 163b of arms 163a from within cutouts 219. In this manner, end effector 200 is no longer secured to connection mechanism 160 of actuation assembly 102 and may be removed from connection with outer tube 162.

As noted above, actuation assembly 102 may be used with alternative end effectors. Once the endoscopic procedure is completed, connection mechanism 160 of actuation assembly 102 may be removed from with in the body cavity and the incision may be closed. End effector 200 may also be removed from within the body cavity through the same incision or port through which end effector 200 was inserted into the body cavity.

As discussed above, connection mechanism 160 of actuation assembly 102 includes a first diameter configured to be received through a first opening in tissue, i.e., through an incision or access device, having a first diameter. One or more end effectors 200 having a second larger diameter are configured to be received through a second opening in tissue, i.e., through an incision or access device, having a second larger diameter. In one embodiment, shaft assembly 106 of endoscopic instrument 100 is configured to be received through an opening measuring 3 mm in diameter, while end effector 200 is configured to be received through an opening measuring 5 mm in diameter. More then one end effector may be introduced through the second opening, thereby limiting the number of openings necessary to complete an endoscopic procedure. The ability to interchange end effectors within the body cavity means a surgeon does not have to retract shaft assembly 106 from within the body cavity to change end effectors. In this manner, the number of opportunities for introducing contaminates within the surgical site is also limited.

With reference now to FIGS. 31-38, an end effector according to another embodiment of the present disclosure is shown generally as end effector 300. End effector 300 is substantially similar in structure and function to end effector 200. Although end effector 300 will be described as relates to selective attachment to a connection mechanism 360, it is envisioned that connection mechanism 160 of actuation assembly 102 described hereinabove may be modified for use with end effector 300. It is also envisioned that end effector 300 may be modified for use with alternative connection mechanism.

With continued reference to FIGS. 31-38, end effector 300 includes a connection assembly 310 and a jaw assembly 330. Connection assembly 310 includes a tubular body 312 having a pair of distal supports 314 extending distally therefrom for operable engagement with jaw assembly 330. Each distal support 314 includes a slot 313 and an opening 315. Slot 313 is configured to receive a connecting pin 316 and opening 315 is configured to receive a pivot pin 318. Tubular body 312 defines a pair of cutouts 319 extending therethrough configured to receive protrusions 363b of arms 363a of a collet 363 formed on a distal end of an outer tube 362 of collection mechanism 360 when arms 363a are in an expanded condition. Cutouts 319 correspond in number and location to arms 363a of collet 363 on outer tube 362.

With reference still to FIGS. 31-38, jaw assembly 330 includes a link member 332, a first jaw member 340, and a second jaw member 350. Link member 332 includes a proximal end 332a having a plurality of ridges 334 and a substantially planar distal end 332b defining an opening 333. Each of first and second jaw members 340, 350 include a proximal end 340a, 350a, respectively, having a diagonal slot 341, 351, respectively, and an opening 343, 353, respectively. A cutout 345, 355 on proximal end 340a, 350a, respectively, of each of first and second jaw members 340, 350, respectively, is configured to accommodate distal end 332b of link member 332. A distal end 340b of first jaw member 340 includes a plurality of teeth 346. A distal end 350b of second jaw member 350 includes a plurality of teeth 356 configured to mesh with teeth 346 of first jaw member 340 when first and second jaw members 340, 350 are in a closed position (FIG. 31), i.e., engage one another.

Still referring to FIGS. 31-38, first and second jaw members 340, 350 are pivotally secured to distal supports 314 of tubular member 310 by pivot pin 318 received through openings 343, 353 of respective first and second jaw members 340, 350 and through openings 315 in distal supports 314. Connecting pin 316 is received through diagonal slots 341, 351 of respective first and second jaw members 340, 350, through slots 313 formed in distal supports 314, and through opening 333 formed in link member 332. Jaw assembly 330 is configured such that distal advancement of connecting pin 316 through slots 313 of distal supports 314 causes opening of jaw assembly 330.

Figure 33:
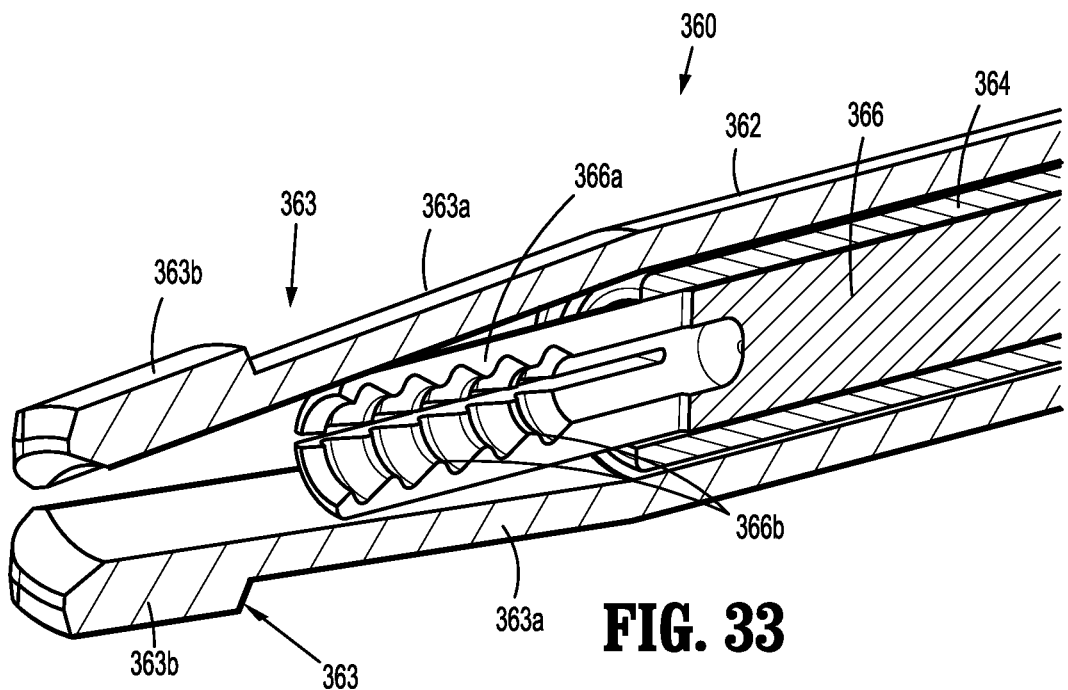
FIG. 33 is an enlarged cross-sectional view taken along line 33-33 shown in FIG. 32.
Figure 34:
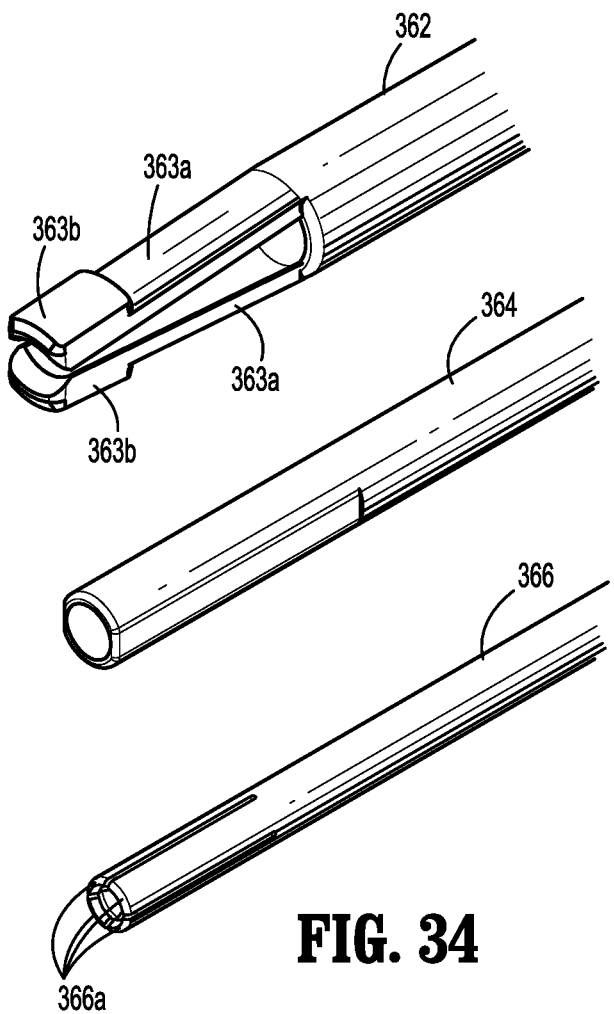
FIG. 34 is an exploded perspective view of the distal end of the connection mechanism shown in FIG. 31.
Figure 39:
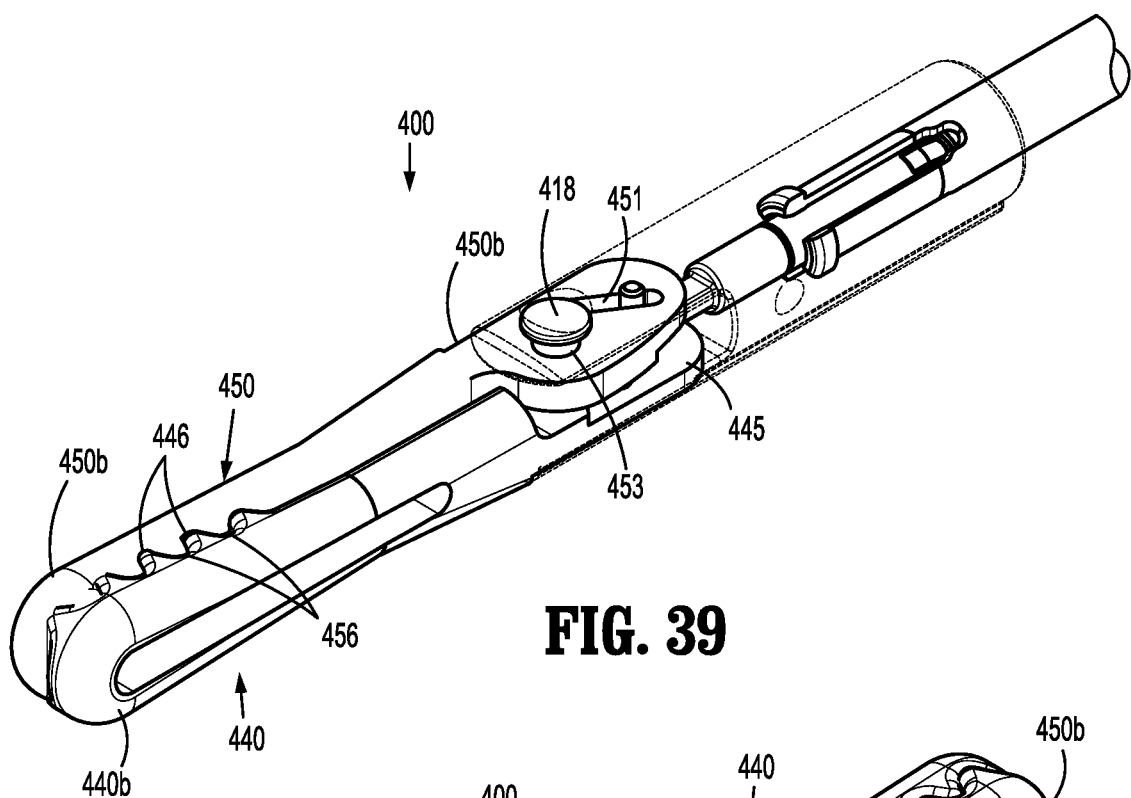
FIG. 39 is a perspective view of an end effector and a distal end of a connection mechanism according to still another embodiment of the present disclosure, the end effector being received on the distal end of the connection mechanism.
Figure 40:
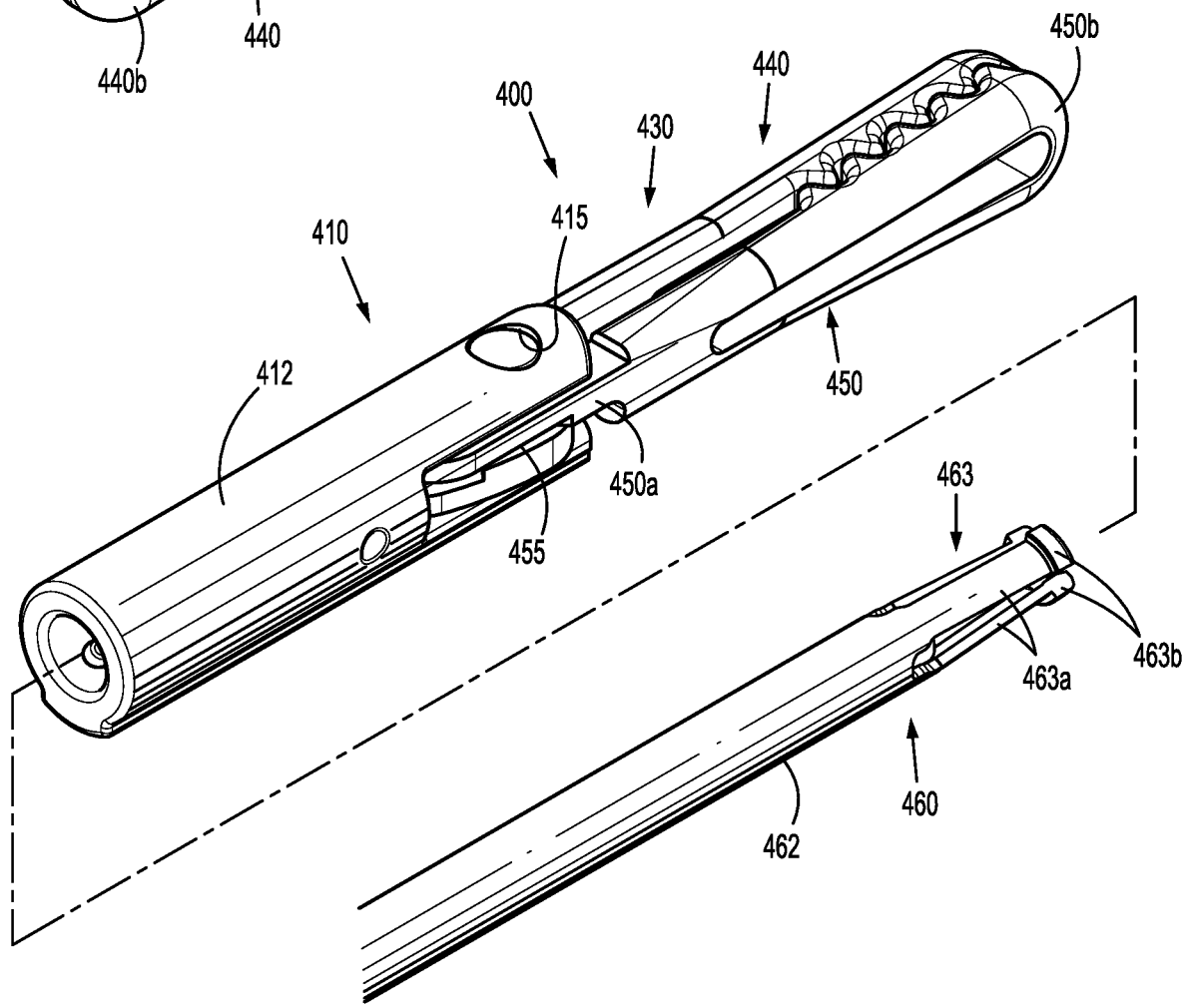
FIG. 40 is a perspective view of the end effector and the distal end of the connection mechanism of FIG. 39, the end effector being separated from the distal end of the connection mechanism.
Figure 41:
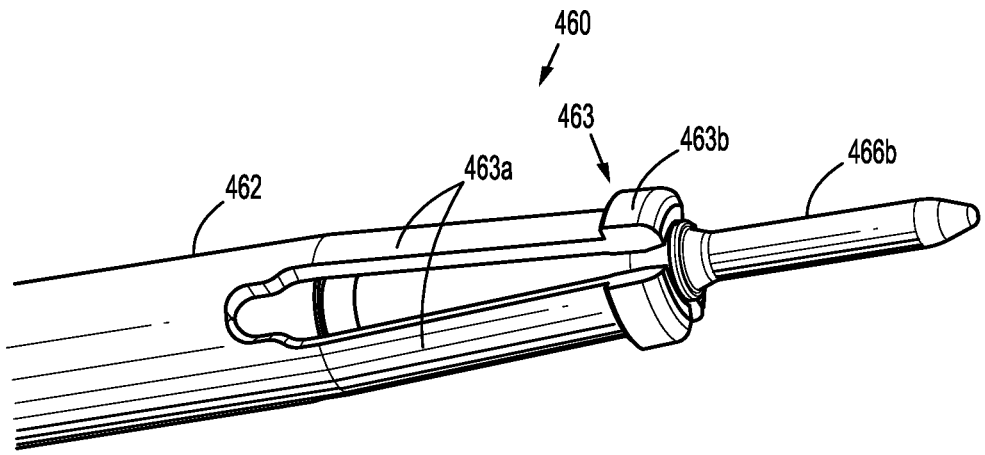
FIG. 41 is a perspective view of the distal end of the connection mechanism shown in FIG. 40, in a position ready for insertion into a body cavity of a patient.
Figure 42:
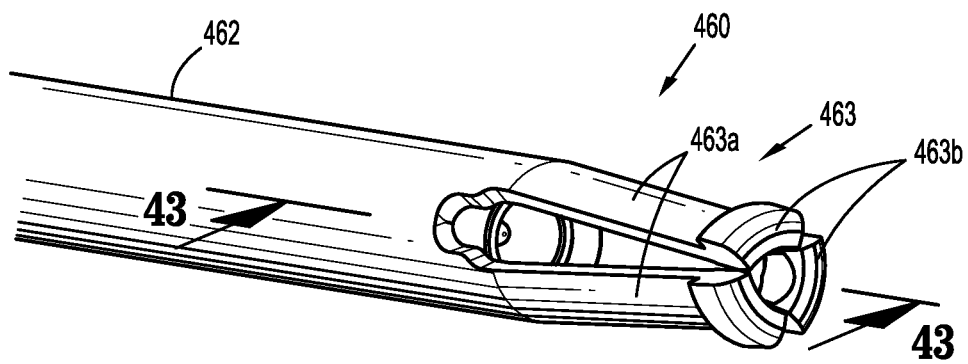
FIG. 42 is a perspective view of the connection mechanism shown in FIG. 40, in a position ready for connection with the end effector shown in FIG. 40.
Figure 43:
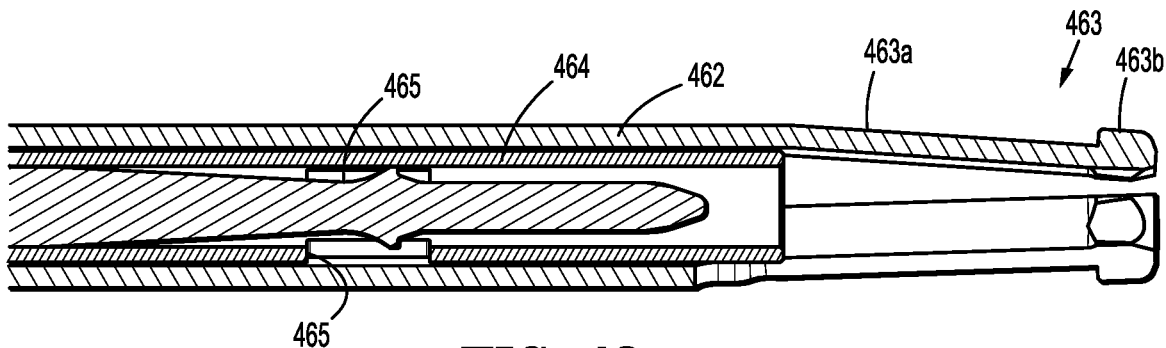
FIG. 43 is a cross-sectional view taken along line 43-43 shown in FIG. 42.
Figure 44:
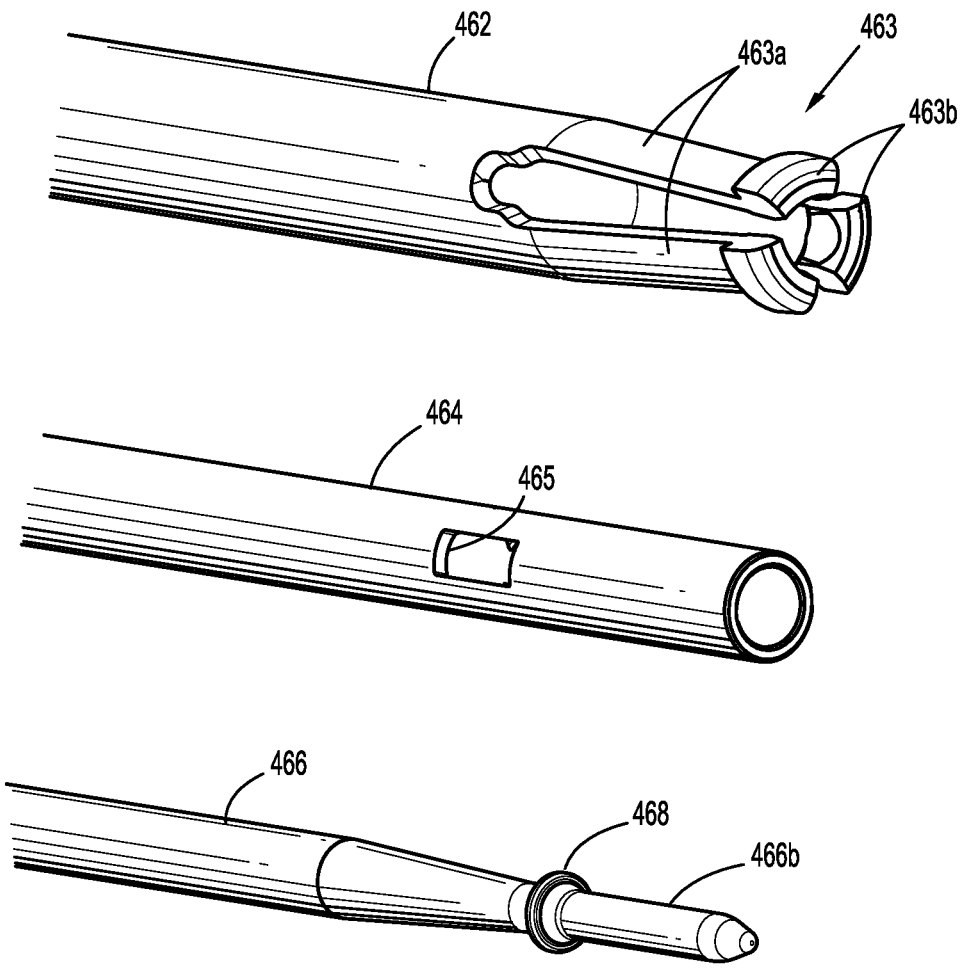
FIG. 44 is an enlarged exploded view of the distal end of the connection mechanism shown in FIG. 43.
Figure 45:
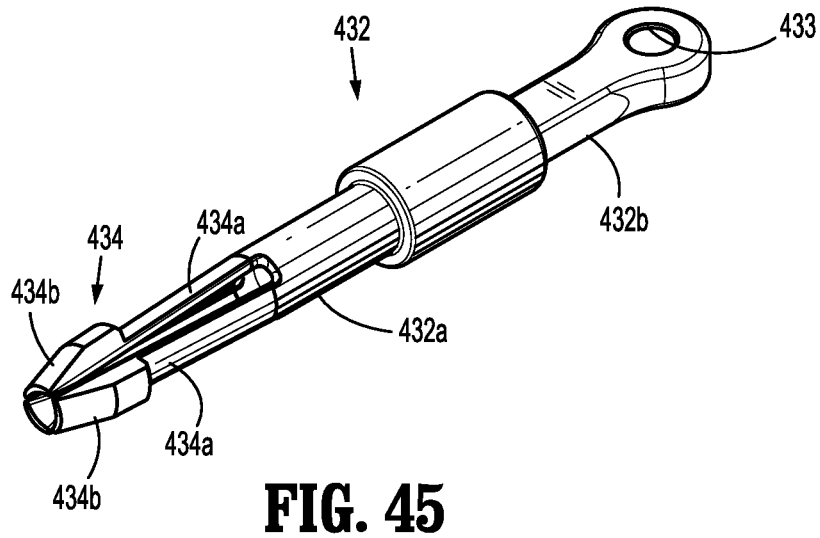
FIG. 45 is a perspective view of a link member of the end effector shown in FIG. 40.
Figure 49:
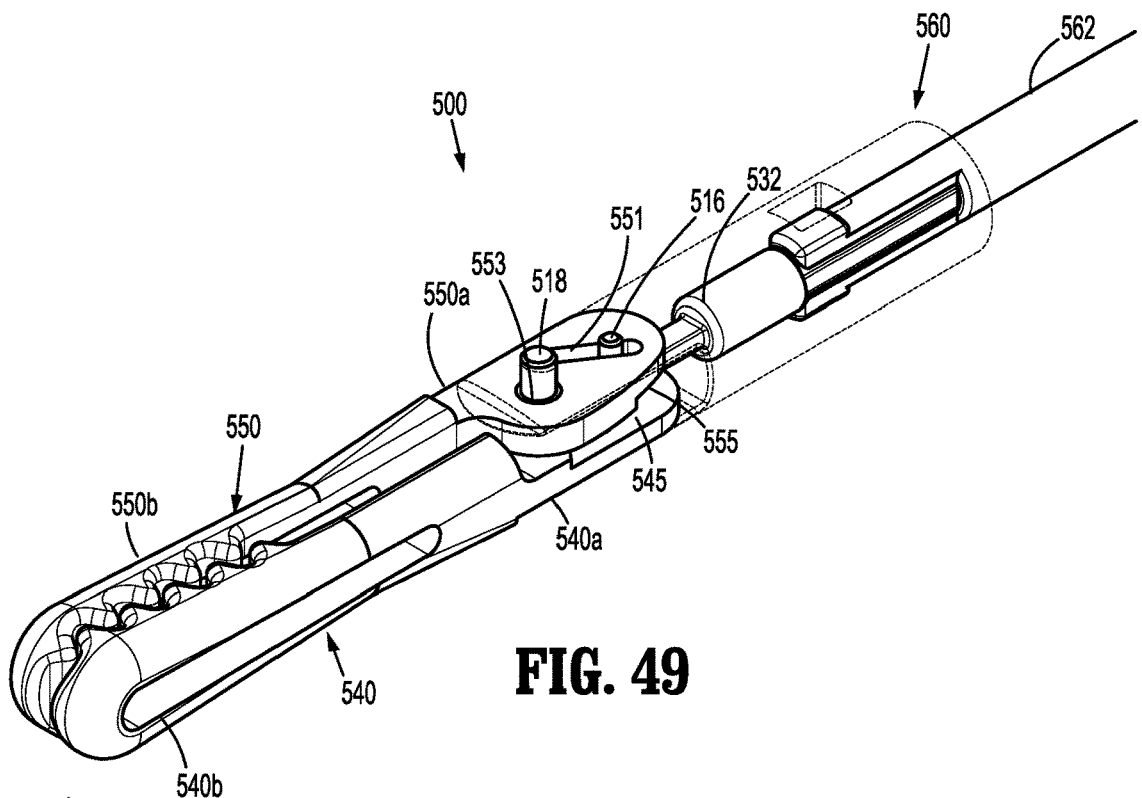
FIG. 49 is a perspective view of an end effector and a distal end of a connection mechanism according to yet another embodiment of the present disclosure, the end effector being received on the distal end of the connection mechanism.
Figure 50:
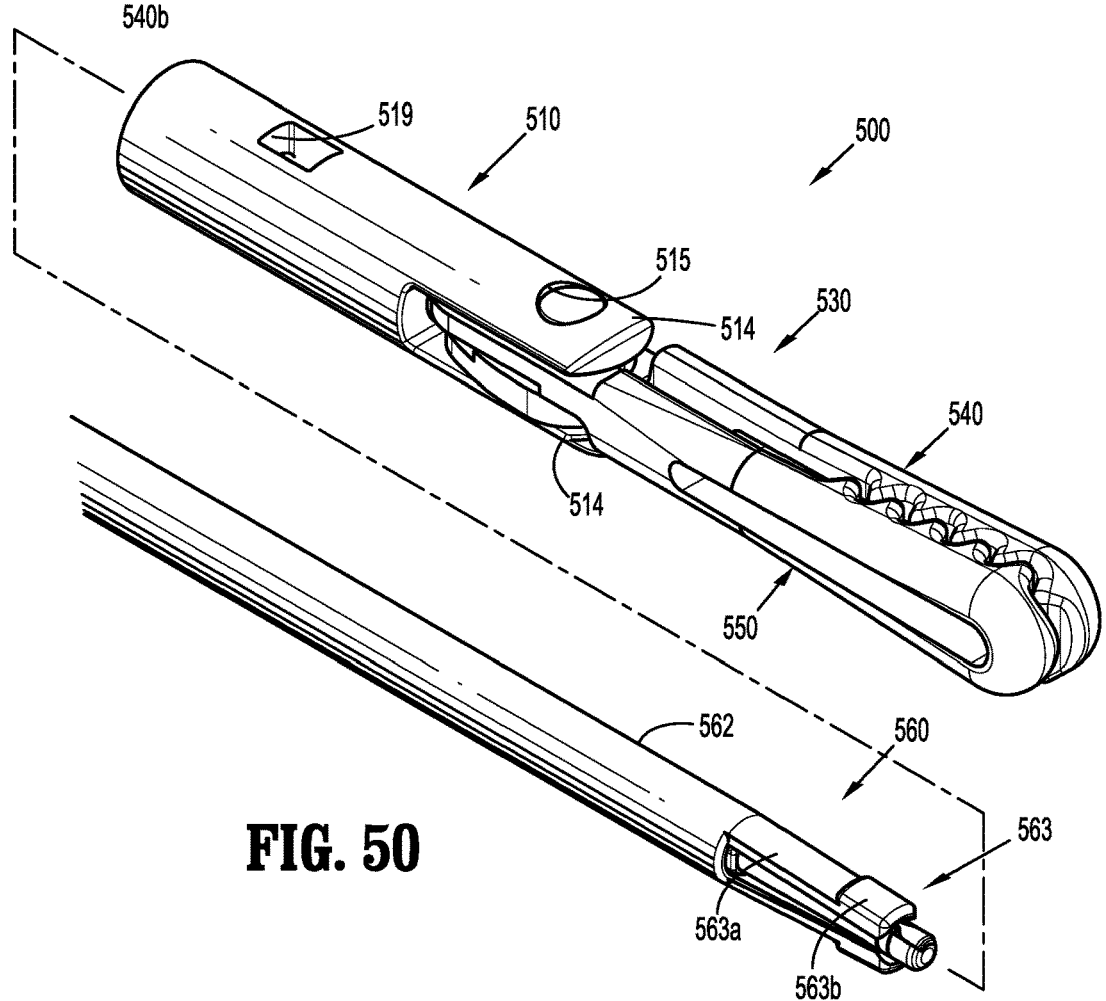
FIG. 50 is a perspective view of the end effector and the distal end of the connection mechanism of FIG. 49, the end effector being separated from the distal end of the connection mechanism.

With particular reference now to FIGS. 33 and 34, end effector 300 is configured for attachment to an actuation assembly (not shown) including connection mechanism 360. Connection mechanism 360 includes outer tube 362, a center tube 364 and an inner tube 366. Outer tube 362 includes collet 363 having a pair of arms 363a. As noted above, each of arms 363a includes a protrusion 363b configured to be received within cutouts 319 defined by tubular member 312. Arms 363a are configured to flex outwardly upon receipt of center tube 364 therethrough. Inner tube 366 includes a distal end having a plurality of fingers 366a extending distally. An inner surface of fingers 366a includes ridges 366b configured to engage ridges 334 formed on proximal end 332a of link member 332.

The attachment of end effector 300 to connection mechanism 360 will now be described with reference to FIGS. 35-38. Referring initially to FIG. 35, distal end of outer tube 362 is received within tubular member 312 of connection assembly 310 such that protrusions 363b formed on collet arms 363a are aligned with cutouts 319 defined by tubular member 312. Turning to FIG. 36, center tube 364 is then advanced distally such that a distal end of center tube 364 causes arms 363a of collet 363 to flex outwardly such that protrusions 363b extend within cutouts 319, thereby securing outer tube 362 to tubular member 312. With reference now to FIG. 37, inner tube 366 is next advanced distally to engage fingers 366a of inner tube 366 with proximal end 332a of link member 332 such that ridges 366b formed on the inner surface of fingers 366a engage ridges 334 formed on proximal end 332a of link member 332. Turning to FIG. 38, center tube 364 is next further advanced distally to cover fingers 366a of inner tube 366 to prevent fingers 366a from splaying, thereby securing the connection between inner tube 366 and link member 332.

Once secured to connection mechanism 360, end effector 300 operates in a manner similar to end effector 200. End effector 300 is removed from connection mechanism 360 in the reverse manner of attachment.

With reference now to FIGS. 39-48, an end effector according to still another embodiment of the present disclosure is shown generally as end effector 400. End effector 400 is configured for operable engagement with an actuation mechanism (not shown) including a connection mechanism 460. As discussed above, actuation assembly 102 (FIG. 1) may be modified for use with end effector 400. End effector 400 includes a connection assembly 410 and a jaw assembly 430.

Connection assembly 410 includes a tubular body 412 having a pair of distal supports 314 extending distally therefrom for operable engagement with jaw assembly 330. Each distal support 414 includes a slot 413 and an opening 415. Slot 413 is configured to receive a connecting pin 416 and opening 415 is configured to receive a pivot pin 418. Tubular body 412 defines a plurality of cutouts 419 formed on an inner surface thereof. Cutouts 419 correspond in number and location to arms 463a of a collet 463 of an outer tube 462 of connection mechanism 460. As shown, tubular member 410 includes three cutouts 419 corresponding to arms 463a of collet 463. It is envisioned that collet 463 may have only a pair of arms or may instead include more than three arms, therefore tubular body 412 may include more or less than three cutouts 419. Tubular member 410 may also include one or more tabs 414 on an inner surface therefore to assist in alignment of collet arms 463 with cutouts 419.

With reference to FIGS. 31, 32 and 35-38, jaw assembly 430 includes a link member 432, a first jaw member 440, and a second jaw member 450. Link member 432 includes a proximal end 432a having a collet 434 formed by a plurality of arms 434a. Each arm 434a includes a protrusion 434b. As shown, collet 434 includes three arms 434a, however, it is envisioned that collet 434 may have more or less then three arms. Link member 432 includes a substantially planar distal end 432b defining an opening 433. Each of first and second jaw members 440, 450 include a proximal end 440a, 450a having a diagonal slot 441, 451, respectively, and an opening 443, 453, respectively. A cutout 445, 455 on proximal end 440a, 450a, respectively, of each of first and second jaw members 440, 450, respectively, is configured to accommodate distal end 432b of link member 432. A distal end 440b of first jaw member 440 includes a plurality of teeth 446. A distal end 450b of second jaw member 450 includes a plurality of teeth 456 configured to engage teeth 446 of first jaw member 440 when first and second jaw members 440, 450 engage one another.

With continued reference to FIGS. 31, 32 and 35-38, first and second jaw members 440, 450 are pivotally secured to distal supports 414 of tubular member 410 by pivot pin 418 received through openings 443, 453 of respective first and second jaw members 440, 450 and through openings 415 in arms 414. Connecting pin 416 is received through diagonal slots 441, 451 of respective first and second jaw members 440, 450, through slots 413 formed in distal supports 414, and through opening 433 formed in link member 432. Jaw assembly 430 is configured such that distal advancement of connecting pin 416 through slots 413 of distal supports 414 causes opening of jaw assembly 430.

With particular reference to FIGS. 41-44, end effector 400 is configured for attachment to an actuation assembly (not shown) having a connection mechanism 460. Connection mechanism 460 includes outer tube 462, an inner tube 464 and a center rod 466. As noted above, outer tube 462 includes collet 463 having a plurality of arms 463a. Each of arms 463a includes a protrusion 463b configured to be received within cutouts 419 defined by tubular member 412. Arms 463a are configured to flex outwardly upon receipt of inner tube 464 therethrough. Inner tube 464 defines a plurality of cutouts 465 configured to receive protrusions 434b of arms 434a of collet 434 formed on proximal end 432a of link member 432. Cutouts 465 correspond in number and location to arms 434a. Center rod 466 includes a tapered distal end 466b configured for facilitating reception of center rod 466 within proximal end 432a of link member 432 to cause the flexing of arms 463a of collet 463. In addition, with particular reference to FIG. 41, prior to attachment of end effector 400 to connection mechanism 460, tapered distal end 466b of center rod 466 may be used to facilitate insertion of connection mechanism 460 through tissue into a body cavity. Center rod 466 includes a lip 468 spaced proximally from tapered distal end 466b and extending circumferentially thereabout. Lip 468 is configured to prevent over-insertion of center rod 466 within collet 434 of link member 432.

The attachment of end effector 400 to connection mechanism 460 will now be described with reference to FIGS. 46-48. Referring initially to FIG. 46, distal end of outer tube 462 is received with tubular member 412 of connection assembly 410 such that protrusions 463b formed on collet arms 463a are aligned with cutouts 419 defined by tubular member 412. As noted above, tubular member 412 may include one or more tabs 414 on an inner surface therefore to assist in alignment of collet arms 463 with cutouts 419. Turning to FIG. 47, inner tube 464 is then advanced distally such the distal end thereof is received over proximal end 432a of link member 432. The distal advancement of inner tube 364 through collet 463 causes arms 463a of collet 463 to flex outwardly such that protrusions 463b extend with cutouts 419, thereby securing outer tube 462 to tubular member 412. With reference now to FIG. 48, center rod 466 is then advanced distally until lip 468 on center rod 466 engages collet 463. Advancement of tapered distal end 166b of center rod 466 within collet 434 of link member 432 causes arms 434a of collet 434 to flex outwardly such that protrusions 434b extend within cutouts 419 formed in tubular member 410, thereby securing inner tube 464 to proximal end 432a of link member 432.

Once secured to connection mechanism 460, end effector 400 operates in the same manner as end effector 200. End effector 400 is removed from connection mechanism in the reverse manner of attachment.

With reference now to FIGS. 49-60, an end effector according to yet another embodiment of the present disclosure is shown generally as end effector 500. End effector 500 is configured for operable engagement with an actuation mechanism (not shown) including a connection mechanism 560. As discussed above, actuation assembly 102 (FIG. 1) may be modified for use with end effector 500. End effector 500 includes a connection assembly 510 and a jaw assembly 530.

With reference to FIGS. 49, 50 and 53-55, connection assembly 510 includes a tubular body 512 having a pair of distal supports 514 extending distally therefrom for operable engagement with jaw assembly 530. Each distal support 514 includes a slot 513 and an opening 515. Slot 513 is configured to receive a connecting pin 516 and opening 515 is configured to receive a pivot pin 518. Tubular member 512 defines a pair of cutouts 519 extending therethrough. Cutouts 519 correspond in number and location to arms 563a of a collet 563 of an outer tube 562 of connection mechanism 560. As shown, tubular member 510 includes two cutouts 519 corresponding to arms 563a of collet 563. It is envisioned that collet 563 may have more than two arms 563a, therefore tubular body 512 may include more than two cutouts 519.

With reference still to FIGS. 49, 50 and 53-55, jaw assembly 530 includes a link member 532, a first jaw member 540, and a second jaw member 550. Link member 532 includes a proximal end 532a defining a cavity 533. A groove 533a is formed on an inner surface of proximal end 532a of link member 532. Link member 532 includes a substantially planar distal end 532b defining an opening 533. Each of first and second jaw members 540, 550 include a proximal end 540a, 550a having a diagonal slot 541, 551, respectively, and an opening 543, 553, respectively. A cutout 545, 555 on proximal end 540a, 550a, respectively, of each of first and second jaw members 540, 550, respectively, is configured to accommodate distal end 532b of link member 532. A distal end 540b of first jaw member 540 includes a plurality of teeth 546. A distal end 550b of second jaw member 550 includes a plurality of teeth 556 configured to engage teeth 546 of first jaw member 540 when first and second jaw members 540, 550 engage one another.

With continued reference to 49, 50 and 53-55, first and second jaw members 540, 550 are pivotally secured to arms 514 of tubular member 510 by pivot pin 518 received through openings 543, 553 of respective first and second jaw members 540, 550 and through openings 515 in distal supports 514. Connecting pin 516 is received through diagonal slots 541, 551 of respective first and second jaw members 540, 550, through slots 513 formed in distal supports 514, and through opening 533 formed in link member 532. Jaw assembly 530 is configured such that distal advancement of connecting pin 516 through slots 513 of distal supports 514 causes opening of jaw assembly 530.

Figure 59:
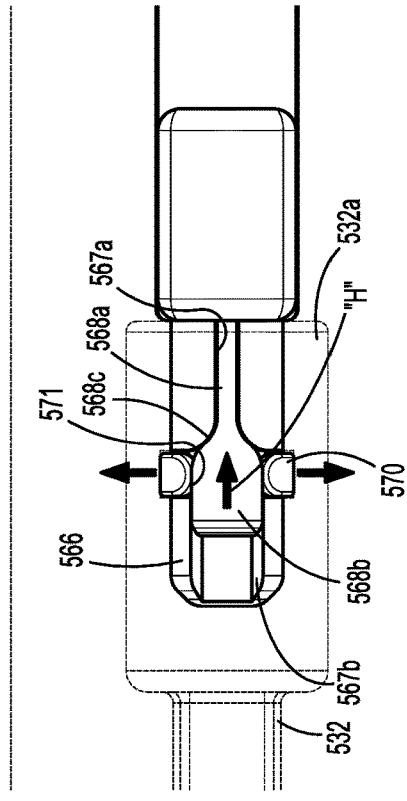
FIG. 59 is a top view of the end effector and the distal end of the connection mechanism shown in FIG. 58, with the tubular body of the end effector shown in phantom.
Figure 61:
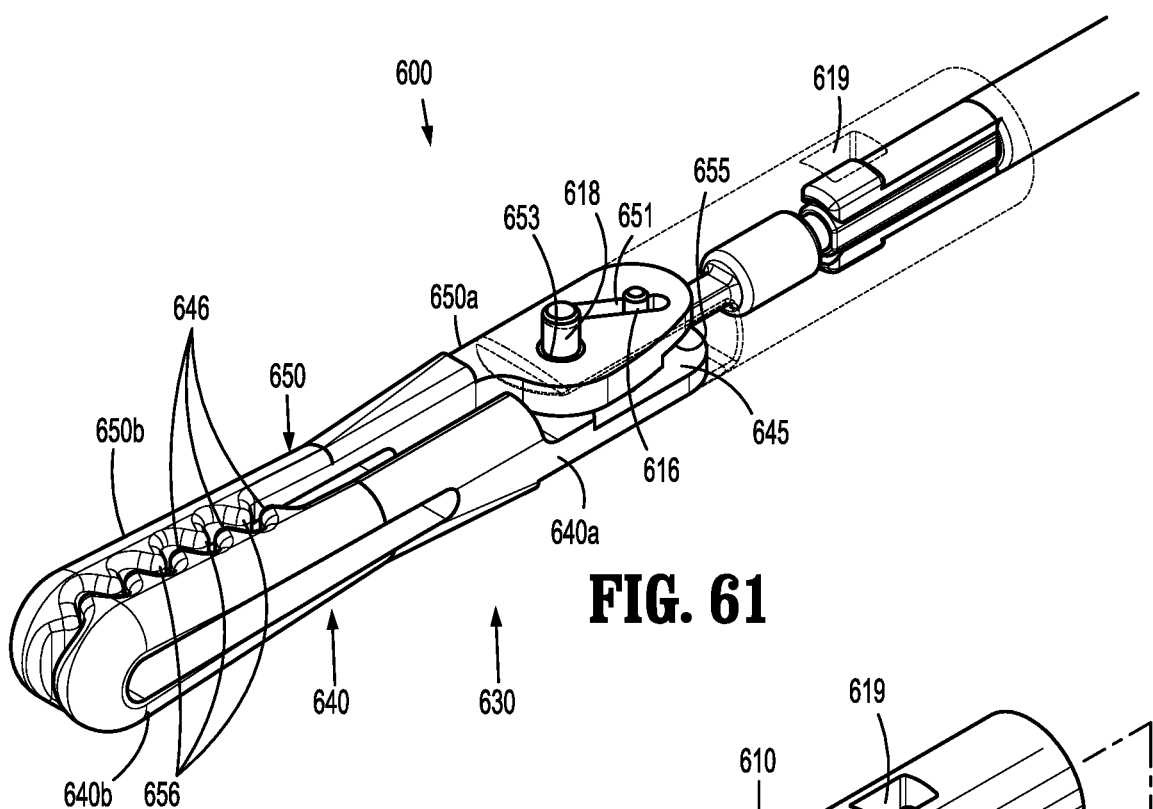
FIG. 61 is a perspective view of an end effector and a distal end of a connection mechanism according to still yet another embodiment of the present disclosure, the end effector being received on the distal end of the connection mechanism.
Figure 62:
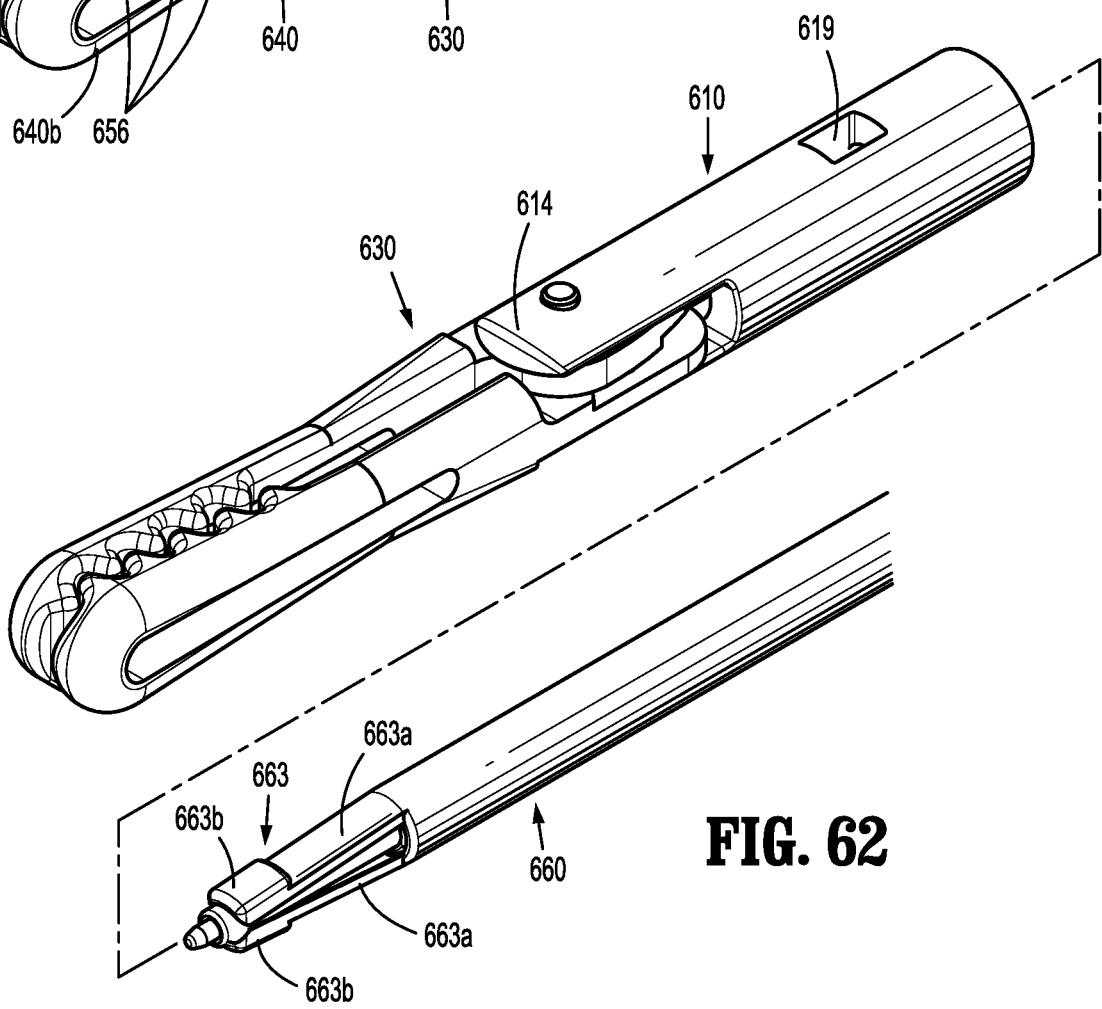
FIG. 62 is a perspective view of the end effector and the distal end of the connection mechanism of FIG. 61, the end effector being separated from the distal end of the connection mechanism.
Figure 63:
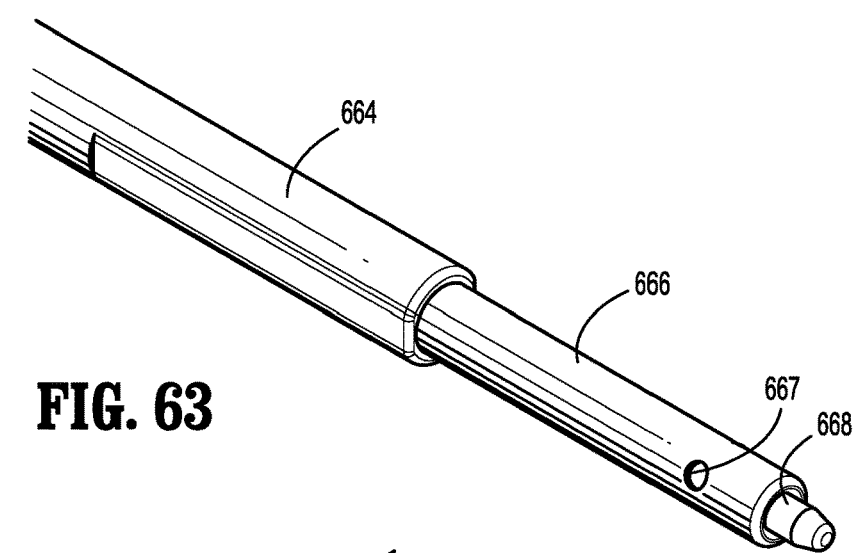
FIG. 63 is a perspective view of the distal end of the connection mechanism shown in FIG. 50, with the outer tube removed.
Figure 64:
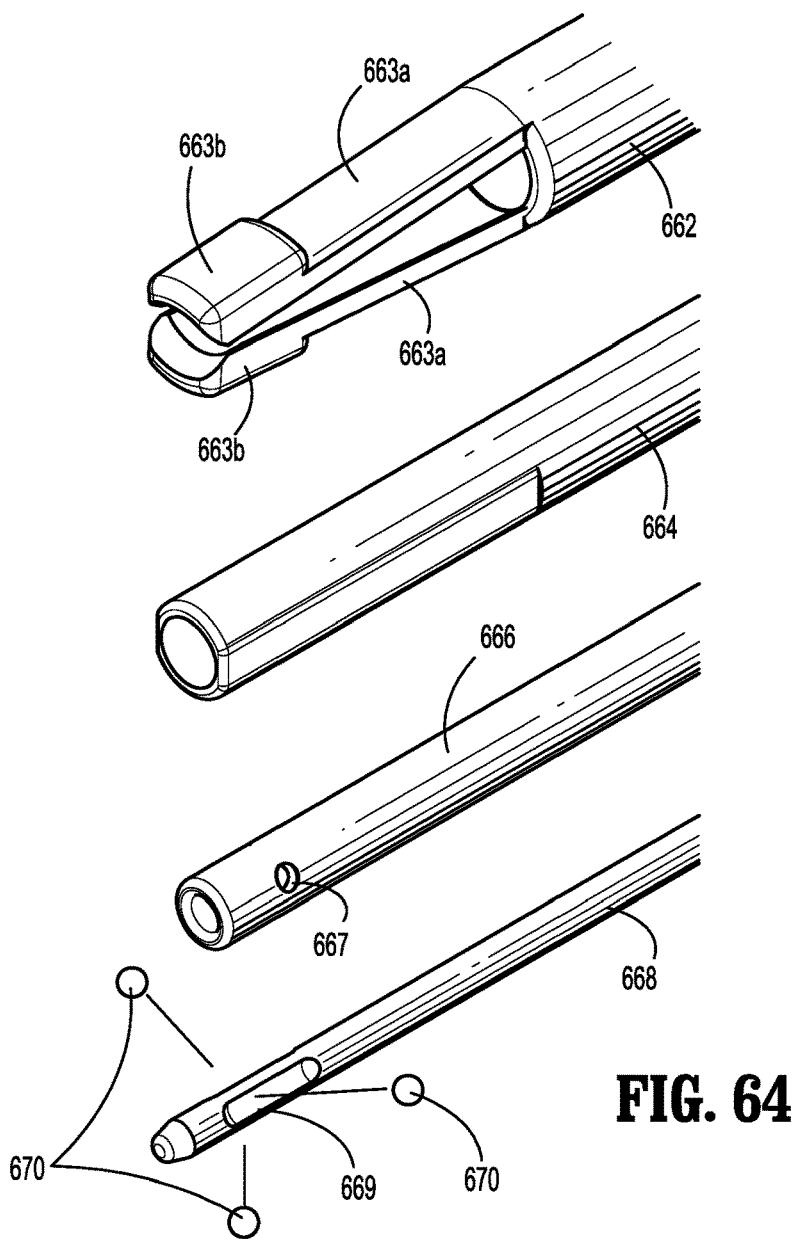
FIG. 64 is an enlarged exploded view of the distal end of the connection mechanism shown in FIG. 63.
Figure 65:
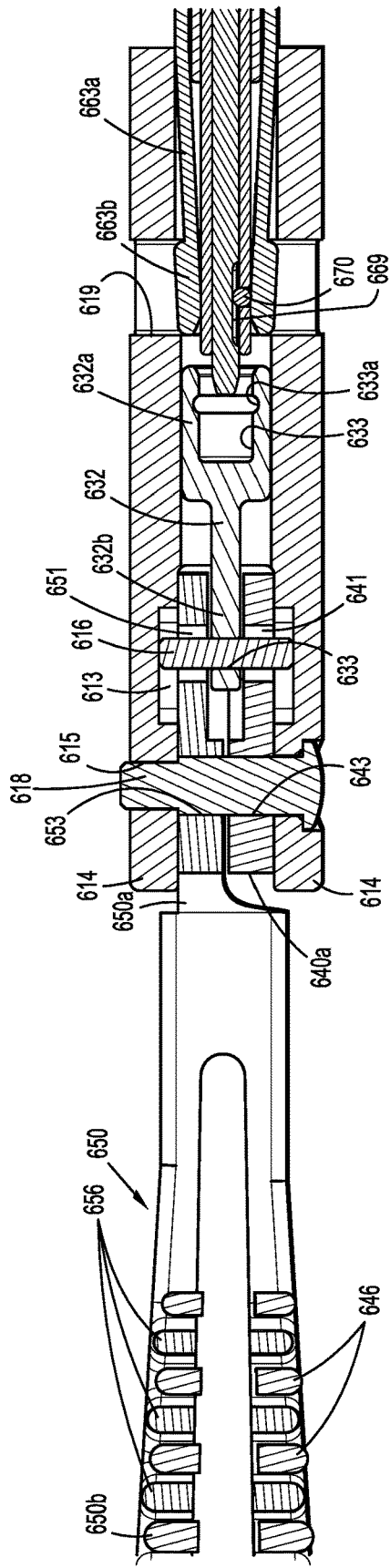
FIG. 65 is a cross-sectional side view of the end effector and the distal end of the connection mechanism shown in FIG. 61, during a first step of attaching the end effector to the connection mechanism.

With reference now to FIGS. 51, 52, 56 and 57, end effector 500 is configured for attachment to an actuation assembly (not shown) having a connection mechanism 560. Briefly, connection mechanism 560 includes outer tube 562, an inner tube 564, a center rod 566, an actuating bar 568 and a ring 570. As noted above, outer tube 562 includes collet 563 having a pair of arms 563a. Each arm 563a includes a protrusion 563b configured to be received within cutouts 519 defined by tubular member 512. Arms 563a are configured to flex outwardly upon receipt of inner tube 564 therethrough. Center rod 566 defines a longitudinal channel 567 configured to receive actuating bar 568 in a sliding manner. Channel 567 includes a proximal section 567a configured to accommodate an elongated proximal portion 568a of actuating bar 568 and a distal section 567b configured to accommodate a widened distal portion 568b of actuating bar 568. Center rod 566 further defines an annular groove 569 spaced from a distal end of center rod 568 and configured to receive ring 570. As noted above, actuating bar 568 includes elongated proximal portion 568a and widened distal portion 568b. A transition 568c between proximal portion 568a and distal portion 568b is tapered. Ring 570 defines a slit 571 sized to receive elongated proximal portion 568a of actuating bar 568. With particular reference to FIGS. 56 and 59, when ring 570 is received within annular groove 569 and actuating bar 568 is received within channel 567 of center rod 566 such that elongate proximal portion 568a is received with slit 571 in ring 570, proximal retraction of actuating bar 568 causes transition 568c between elongate proximal portion 568a and widened distal portion 568b to be received with slit 571. Continued proximal retraction of actuating bar 568 results in expansion of ring 570.

Figure 53:
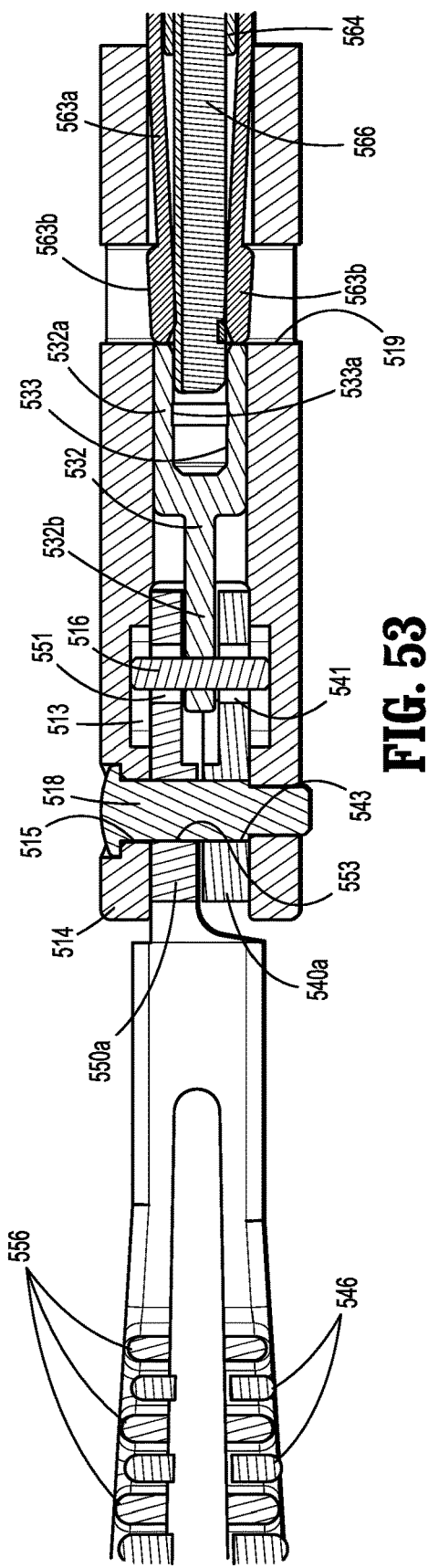
FIG. 53 is a cross-sectional side view of the end effector and the distal end of the connection mechanism shown in FIG. 50, during a first step of attaching the end effector to the connection mechanism.
Figure 54:
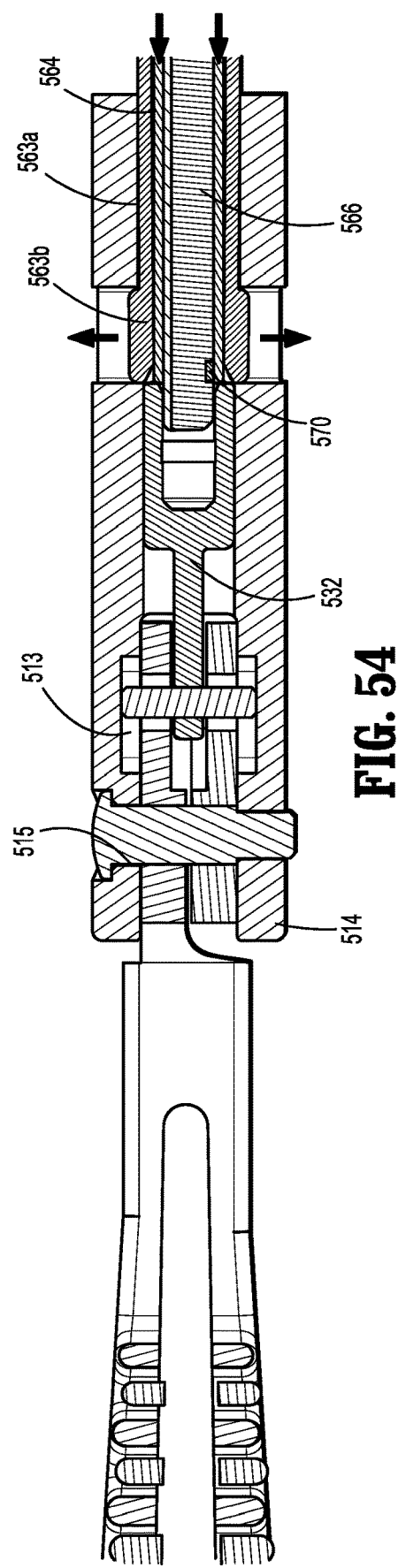
FIG. 54 is a cross-sectional side view of the end effector and the distal end of the connection mechanism shown in FIG. 50, during a subsequent attachment step.
Figure 58:
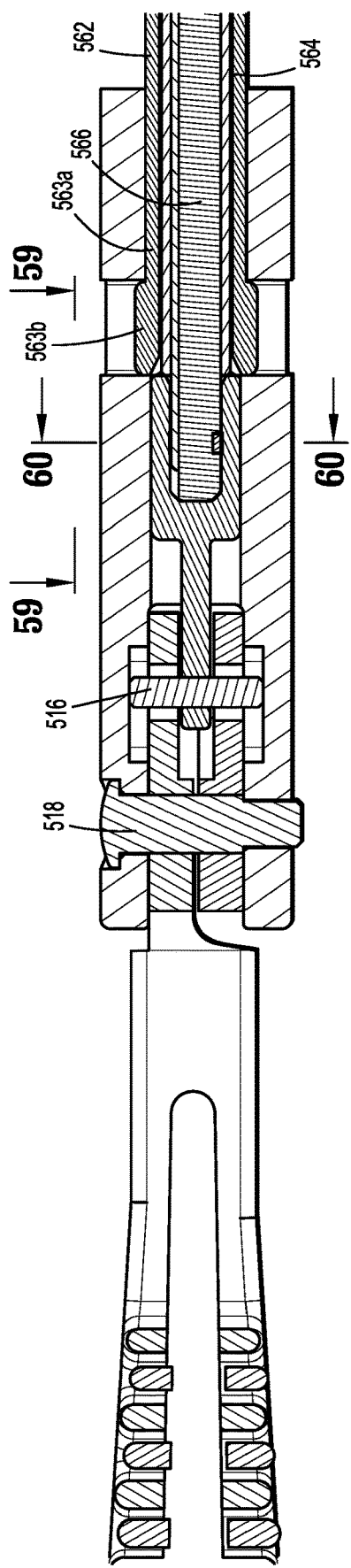
FIG. 58 is a cross-sectional side view of the end effector and the distal end of the connection mechanism shown in FIG. 50, upon complete attachment of the end effector to the distal end of the connection mechanism.
Figure 60:
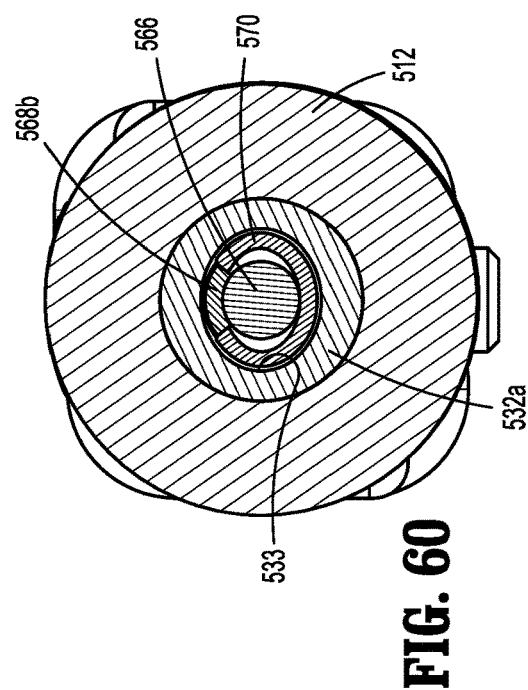
FIG. 60 is a cross-sectional view taken along line 57-57 shown in FIG. 58.

The attachment of end effector 500 to connection mechanism 560 will now be described with reference to FIGS. 53-60. Referring initially to FIG. 53, distal end of outer tube 562 is received with tubular member 512 of connection assembly 510 of end effector 500 such that protrusions 563b formed on collet arms 563a are aligned with cutouts 519 defined by tubular member 512. Turning to FIG. 54, inner tube 564 is then advanced distally such the distal end thereof is received through collet 563 of outer tube 562 causing collet arms 563a to flex outwardly such that protrusions 563b extend within cutouts 519. In this manner, outer tube 562 is secured to tubular member 512. With reference now to FIGS. 55-57, center rod 566 is then advanced distally to be received with cavity 533 formed in proximal end 532a of link member 532. Cavity 533 is configured such that upon complete reception of the distal end of center rod 566 within cavity 533, ring 570 mounted on center rod 566 is aligned with groove 533a formed on the inner surface of proximal end 532a of link member 532. Turning to FIGS. 58-60, once ring 570 is aligned with groove 533a, actuating bar 568 is retracted proximally, as indicated by arrow "H". Distal retraction of actuating bar 568 relative to ring 570 causes engagement of ring 570 with transition 568c of actuating bar 568. As discussed above, continued distal retraction of actuating bar 568 relative to ring 570 causes the expansion of ring 570 within groove 533a formed in proximal end 532a of link member 532. Receipt of ring 570 within groove 533a secures center rod 568 to link member 532.

Once secured to connection mechanism 560, end effector 500 operates in the same manner as end effector 500. End effector 500 is removed from connection mechanism 560 in the reverse manner of attachment.

With reference now to FIGS. 61-70, an end effector according to still yet another embodiment of the present disclosure is shown generally as end effector 600. End effector 600 is configured for operable engagement with an actuation mechanism (not shown) including a connection mechanism 660. As discussed above, actuation assembly 102 (FIG. 1) may be modified for use with end effector 600. End effector 600 includes a connection assembly 610 and a jaw assembly 630.

With reference to FIGS. 61, 62 and 65-70, connection assembly 610 includes a tubular body 612 having a pair of distal supports 614 extending distally therefrom for operable engagement with jaw assembly 630. Each distal support 614 includes a slot 613 and an opening 615. Slot 613 is configured to receive a connecting pin 616 and opening 615 is configured to receive a pivot pin 618. Tubular member 612 defines a pair of cutouts 619 extending therethrough. Cutouts 619 correspond in number and location to arms 663a of a collet 663 of an outer tube 662 of connection mechanism 660. As shown, tubular member 610 includes two cutouts 619 corresponding to arms 663a of collet 663. It is envisioned that collet 663 may have more than two arms 663a, therefore tubular body 612 may include more than two cutouts 619.

With reference still to FIGS. 61, 62 and 65-70, jaw assembly 630 includes a link member 632, a first jaw member 640, and a second jaw member 650. Link member 632 includes a proximal end 632a defining a cavity 633. A groove 633a is formed on an inner surface of proximal end 632a of link member 532. Link member 632 includes a substantially planar distal end 632b defining an opening 633. Each of first and second jaw members 640, 650 include a proximal end 640a, 650a having a diagonal slot 641, 651, respectively, and an opening 643, 653, respectively. A cutout 645, 655 on proximal end 640a, 650a, respectively, of each of first and second jaw members 640, 650, respectively, is configured to accommodate distal end 632b of link member 632. A distal end 640b of first jaw member 540 includes a plurality of teeth 646. A distal end 650b of second jaw member 550 includes a plurality of teeth 656 configured to mesh with teeth 646 of first jaw member 640 when first and second jaw members 640, 650 engage one another.

With continued reference to 61, 62 and 65-70, first and second jaw members 640, 650 are pivotally secured to arms 614 of tubular member 610 by pivot pin 618 received through openings 643, 653 of respective first and second jaw members 640, 650 and through openings 615 in distal supports 614. Connecting pin 616 is received through diagonal slots 641, 651 of respective first and second jaw members 640, 650, through slots 613 formed in distal supports 614, and through opening 633 formed in link member 632. Jaw assembly 630 is configured such that distal advancement of connecting pin 616 through slots 613 of distal supports 614 causes opening of jaw assembly 630.

With reference now to FIGS. 63, 64, 68 and 70, end effector 600 is configured for attachment to an actuation assembly (not shown) having a connection mechanism 660.

Connection mechanism 660 includes outer tube 662, a center tube 664, an inner tube 666, a center rod 668, and a plurality of spheres 670. As noted above, outer tube 662 includes collet 663 having a pair of arms 663a. Each arm 663a includes a protrusion 663b configured to be received within cutouts 619 defined by tubular member 612. Arms 663a are configured to flex outwardly upon receipt of center tube 664 therethrough. Inner tube 666 is configured to be slidably received through center tube 664. Inner tube 666 defines a plurality of openings 667 formed circumferentially about inner tube 666 spaced proximally of a distal end thereof. As shown, inner tube 666 defines three openings 667 for accommodating the three spheres 670. It is envisioned that connection mechanism 660 may have more or less then three spheres 670. Accordingly, inner tube 666 may define more or less then three openings 667. Center rod 568 is configured to be slidably received through inner tube 666 and defines a plurality of longitudinal grooves 669 configured to accommodate a portion of spheres 670. Grooves 669 positioned circumferentially to align with openings 667 in inner tube 666. The number of grooves 569 corresponds to the number of spheres 670.

Figure 66:
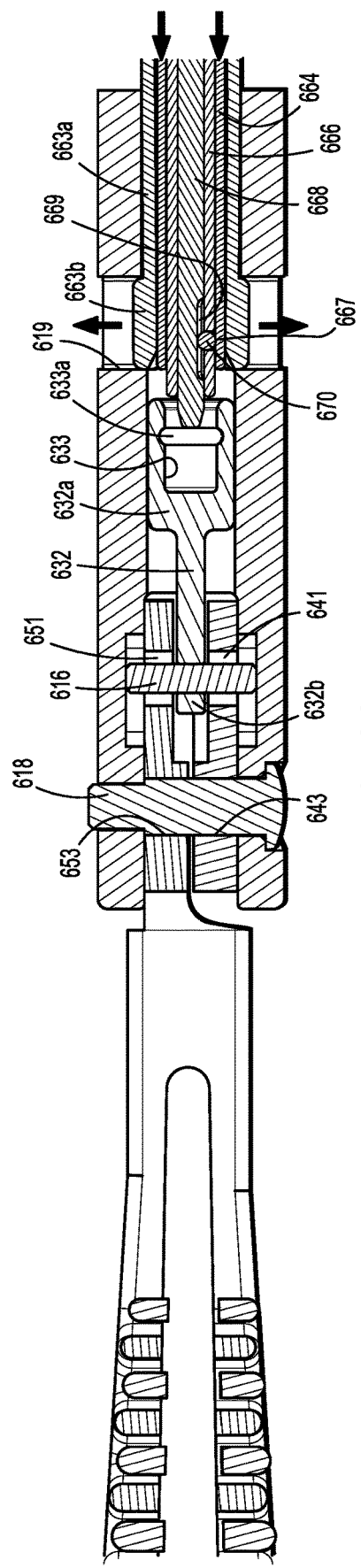
FIG. 66 is a cross-sectional side view of the end effector and the distal end of the connection mechanism shown in FIG. 61, during a subsequent attachment step.
Figure 67:
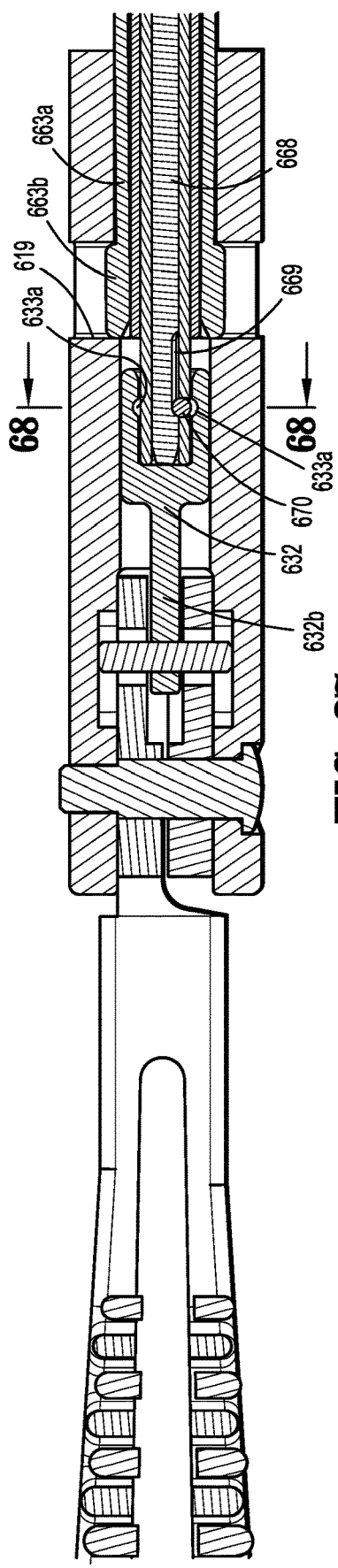
FIG. 67 is a cross-sectional side view of the end effector and the distal end of the connection mechanism shown in FIG. 61, during another attachment step.
Figure 68:
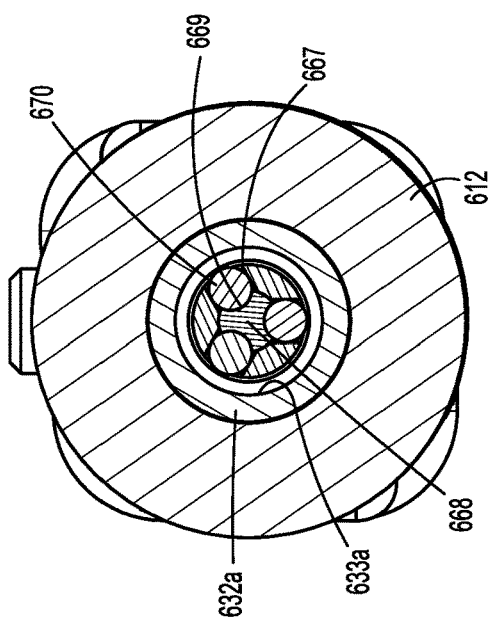
FIG. 68 is a cross-sectional view taken along line 68-68 shown in FIG. 67.
Figure 69:
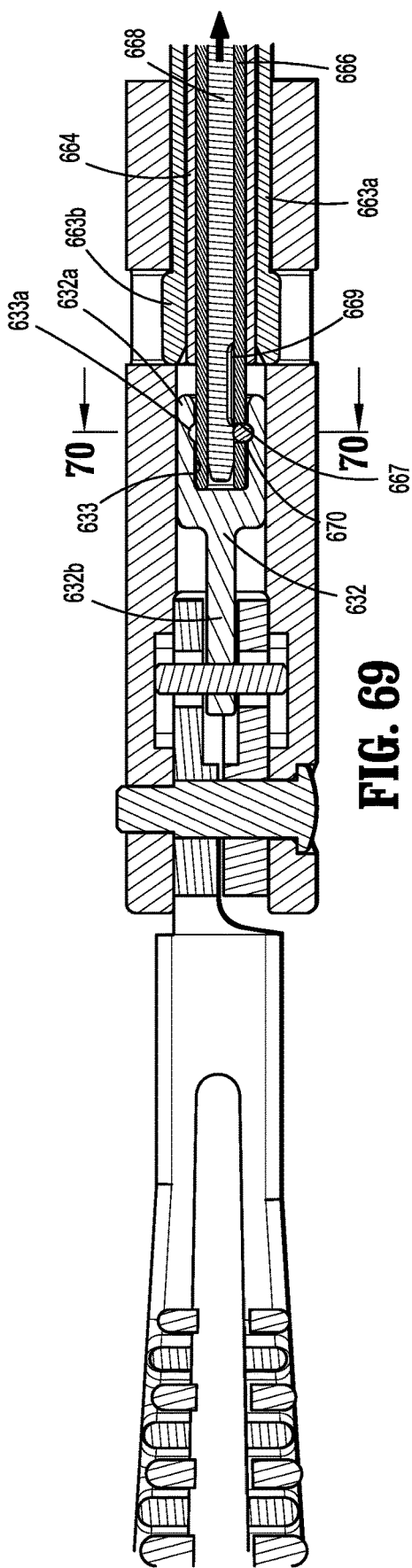
FIG. 69 is a cross-sectional side view of the end effector and the distal end of the connection mechanism shown in FIG. 61, upon complete attachment of the end effector to the distal end of the connection mechanism.
Figure 70:
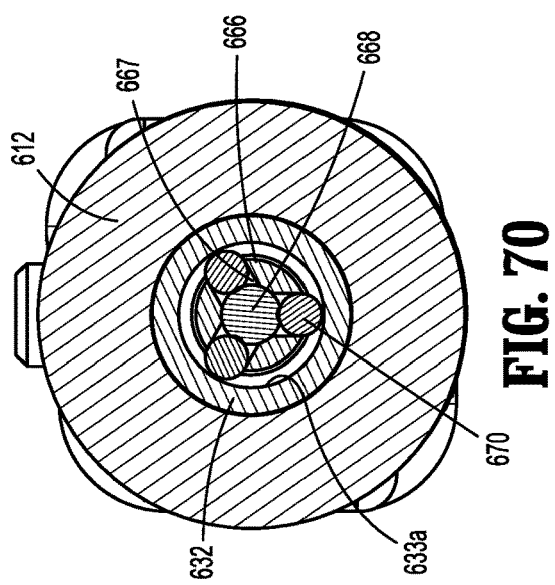
FIG. 70 is a cross-sectional view taken along line 70-70 shown in FIG. 69.

The attachment of end effector 600 to connection mechanism 660 will now be described with reference to FIGS. 65-70. Referring initially to FIG. 60, distal end of outer tube 662 is received with tubular member 612 of connection assembly 610 of end effector 600 such that protrusions 663b formed on collet arms 663a are aligned with cutouts 619 defined by tubular member 612. Turning to FIG. 66, center tube 664 is then advanced distally such the distal end thereof is received through collet 663 of outer tube 662 causing collet arms 663a to flex outwardly such that protrusions 663b extend within cutouts 619. In this manner, outer tube 662 is secured to tubular member 612. With reference now to FIGS. 67 and 68, inner tube 566 and center rod 568 are then simultaneously advanced distally to be received with cavity 633 formed in proximal end 632a of link member 632. Cavity 633 is configured such that upon complete reception of the distal end of inner tube 666 and center rod 668 within cavity 633, openings 667 in inner tube 666 and slots 669 in center rod 668 align with groove 633a formed in proximal end 632a of link member 632. As shown, in this position, spheres 670 are partially received within slots 669 formed in center rod 668 and partially received within opening 667 formed in inner tube 666. Turning to FIGS. 69 and 70, once openings 667 and slots 669 are aligned with groove 633a, center rod 668 is retracted proximally, as indicated by arrow "I". Distal retraction of center rod 668 relative to inner tube 666 results in spheres 670 being ejected from within slots 669. Ejection spheres 670 from slots 667 pushes spheres 670 radially outward into groove 633a formed in proximal end 632a of link member 632. Receipt of spheres 670 within groove 633a secures inner tube 666 to link member 632.

Once secured to connection mechanism 660, end effector 600 operates in a similar manner to the above-disclosed end effectors 600. End effector 600 is removed from connection mechanism 660 in the reverse manner of attachment.

With reference now to FIGS. 71-78, a device for positioning an end effector within a body cavity and for facilitating attachment of end effector with the connection mechanism of an actuation assembly shown generally as holder 800. Although shown and described as relates to end effector 700 and connection mechanism 760, holder 800 may be used with any of the above described end effectors and connection mechanism. It is envisioned that holder 800 may also be modified for use with other end effectors.

Figure 75:
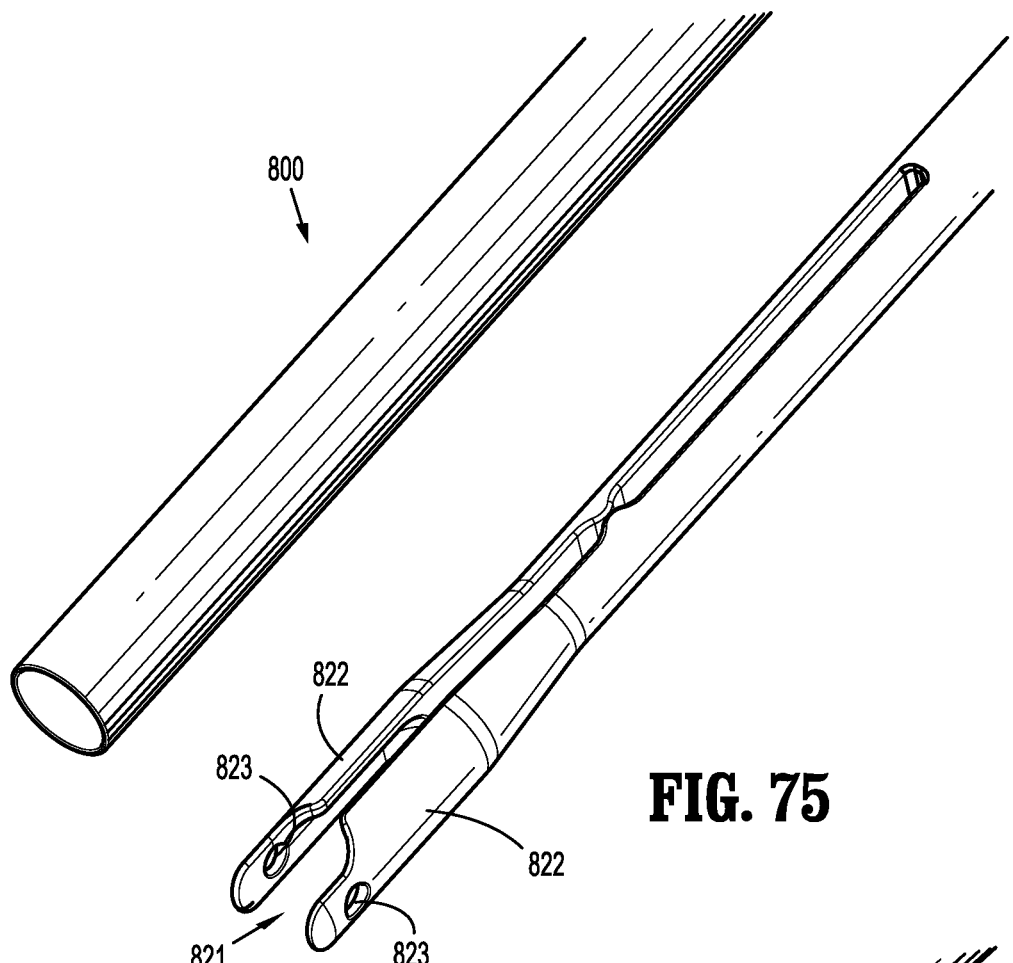
FIG. 75 is an exploded view of the holder show in FIG. 71.
Figure 76:
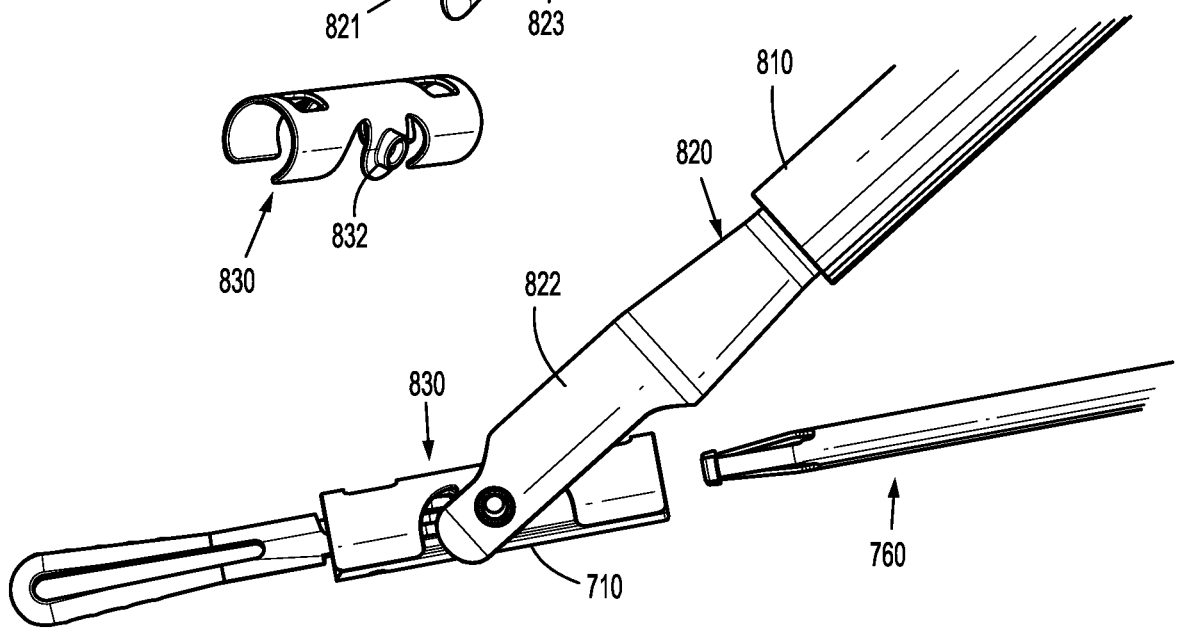
FIG. 76 is a side view of the holder and end effector of FIG. 73, prior to attachment with a distal end of a connection mechanism.

With particular reference to FIG. 75, holder 800 includes a tubular body 810, a shaft 820, a capsule 830, and an actuation mechanism 840. Shaft 820 includes a pair of extensions 822 on a distal end thereof. Extensions 822 taper outwardly and define a slot 821 therebetween. Each extension 822 includes an opening 823 configured to receive a pivot member 832 extending laterally from capsule 830. Extensions 822 are spaced apart such that capsule 830 may be pivoted relative to extensions 822 when tubular body 810 is in a first or retracted position (as shown). The configuration of extensions 822 is such that distal advancement of tubular body 810 about extensions 822 causes extensions 822 to move towards one another. In this manner, extensions 822 squeeze capsule 830, thereby fixing the orientation of capsule 830 relative to extensions 822. Retraction of tubular body 810 relative to extension 822 allows extensions 822 to return to the original spaced configured, thereby loosening the hold on capsule 830 and permitting pivoting of capsule 830 relative to extensions 822.

Figure 72:
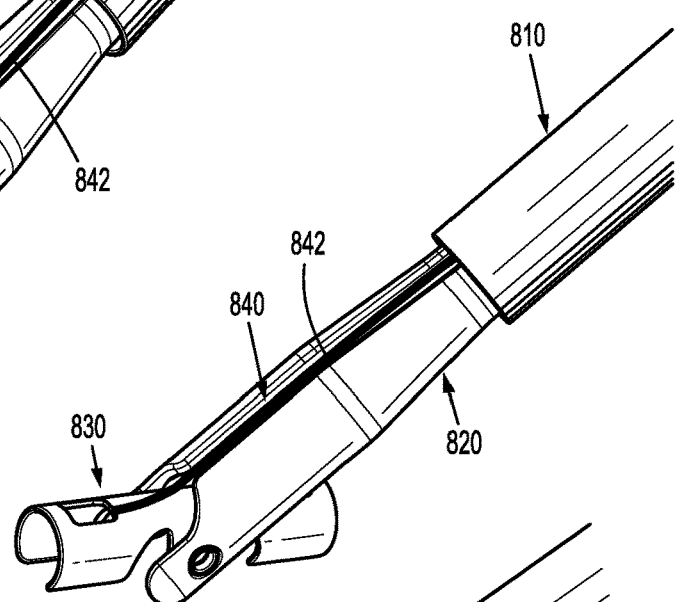
FIG. 72 is a perspective view of the holder shown in FIG. 71, in a second or operative position.

Capsule 830 includes a cylindrical body having a substantially C-shaped cross-section configured to selectively retain end effector 700, or any other similarly sized end effector. As noted above, capsule 830 includes a pair of pivot members 832 extending laterally outward therefrom configured to be received within openings 823 formed in extensions 822. Capsule 830 is configured such that squeezing of extensions 822 constricts capsule 830 about end effector 700 to more securely retain end effector 700 therewith. In a first position (FIG. 71), capsule 830 is axially aligned with tubular body 810 and shaft 820. In this position, holder 800 is configured to facilitate insertion of end effector 700 into a body cavity (not shown) through an opening in the tissue, i.e., an incision or an access port. Once received within the body cavity, capsule 830 is configured to be rotated relative to tubular body 810 and shaft 820 between one or more positions (FIG. 72).

Figure 73:
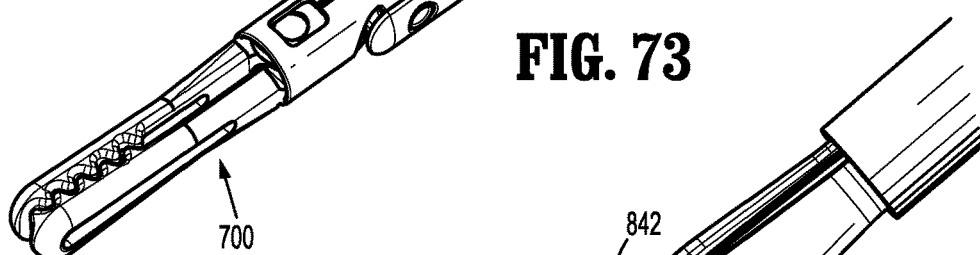
FIG. 73 is a perspective view of the holder shown in FIG. 71, operably engaged with an end effector.

The rotation of capsule 830 is achieved through the operation of actuation mechanism 840. As shown actuation mechanism 840 includes a flexible link 842 having a distal end operative fixed to capsule 800 and a proximal end (not shown) configured for operable engagement by a user to permit retraction and advancement of link 842. As shown in FIG. 73, in a first position, link 842 is in an advanced position, thereby causing capsule 830 to assume the first or axially aligned position. Retraction of link 842 causes capsule 830 to pivot about pivot members 832, thereby changing the orientation of capsule 830 relative to tubular body 810 and shaft 820. It is envisioned that actuation mechanism 840 may articulate capsule 830 through ninety degrees (90°) of articulation.

Attachment of end effector 700 to connection mechanism 760 with the assistance of holder 800 will now be described with reference to FIGS. 73, 74 and 76-78. Referring initially to FIG. 73, end effector 700 is loaded into capsule 830 of holder 800. Capsule 830 is in the first or axially aligned configuration to facilitate insertion into a body cavity through an incision or access port.

Figure 74:
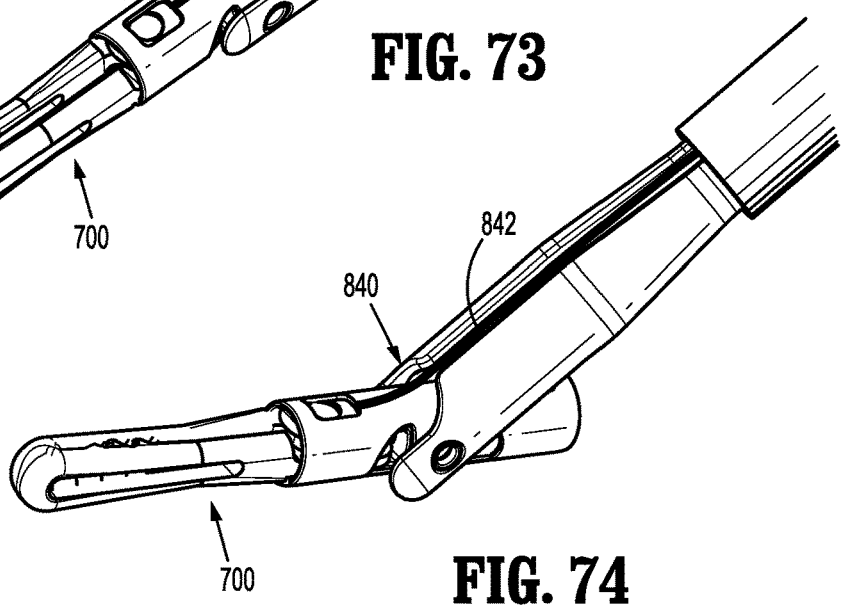
FIG. 74 is a perspective view of the holder shown in FIG. 71, operably engaged with the end effector shown in FIG. 73.

Turning to FIG. 74, once capsule 830, including end effector 700 has been received within the body cavity, link 842 of actuation mechanism 840 is retracted to cause the pivoting of capsule 830 relative to shaft 820. Capsule 830 is pivoted to an orientation best suited for receiving connection mechanism 760 (FIG. 76) within connector assembly 710 of end effector 700.

Figure 77:
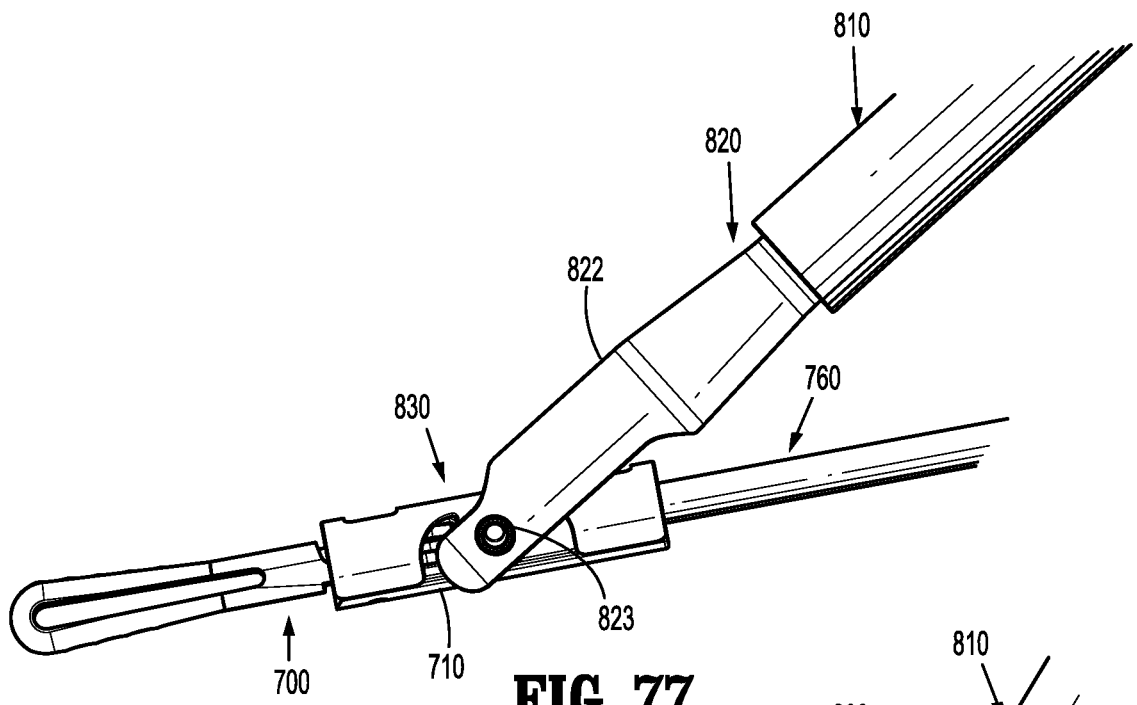
FIG. 77 is a side view of the holder, the end effector, and the distal end of the connection mechanism shown in FIG. 76, upon attachment of the end effector to the distal end of the connection mechanism.

With reference now to FIG. 77, connection mechanism 760 is then received within tubular body 712 of end effector 700. End effector 700 is then secured to connection mechanism through operation of the actuation assembly (not shown) from which connection mechanism 760 extends. At any point during the connection of end effector 700 with connection mechanism 760, tubular body 810 of holder 800 may be advanced on shaft 810 to cause the approximation of extension 822, thereby causing the squeezing of capsule 830 to more securely retain end effector 700 therein to facilitate connection of end effector 700 to connection mechanism 760.

Figure 78:
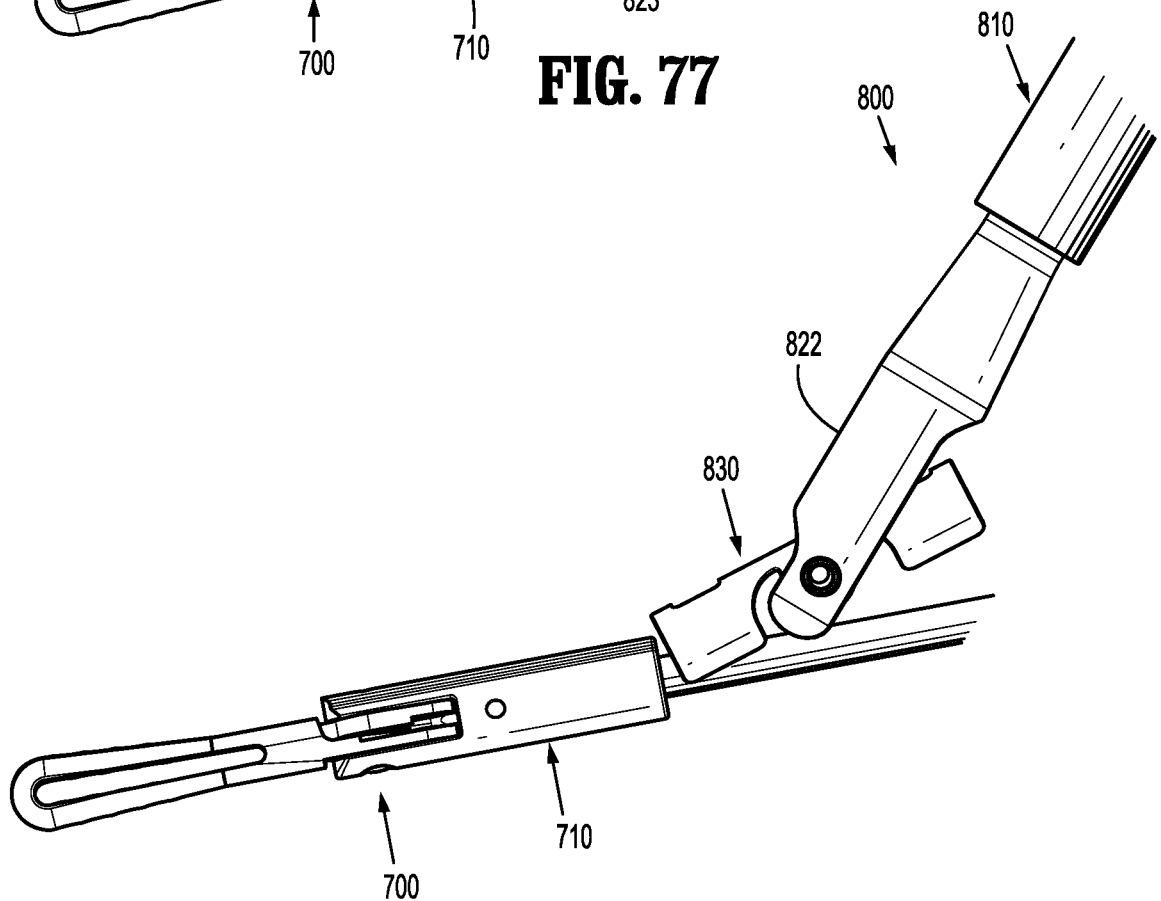
FIG. 78 is a side view of the holder, the end effector, and the distal end of the connection mechanism shown in FIG. 76, upon release of the end effector from the holder.

Turning now to FIG. 78, once end effector 700 is secured to connection mechanism 760, if tubular body 810 has been advanced relative to shaft 820 to more securely retain end effector 700 within capsule 830, tubular body 810 is retracted to release the tightened engagement of end effector 700. Distal advancement of end effector 700 relative to capsule 830 causes end effector 700 to disengage from capsule 830. Once disengaged, end effector 700 may be operated in any suitable manner. Capsule 830 may be returned to the first position (FIG. 71) and be removed from within the body cavity.

It is envisioned that holder 800 may be used in the reverse order to disengage end effector 700 from connection mechanism 760 and to remove end effector 700 from within the body cavity. Holder 800 may be configured to be reused, or may instead be disposable.

As discussed above, the presently disclosed actuation assembly may be modified for use with any of the above disclosed end effectors. It is envisioned that an actuation assembly may be provided as a kit with one or more end effectors for performing various functions. As noted above, although shown in the form of graspers for grasping tissue or other structure, it is envisioned that the end effectors of the present disclosure may instead modified for stapling, vessel sealing, and cutting. In this manner, a first end effector may be provided to perform a first function and one or more end effectors may be provided to perform one or more different functions. As discussed above, the attachment and separation of the various end effectors with the actuation assembly may be accomplished within the body cavity of the patient, i.e., without removal of the instrument from within the body cavity.

Although the illustrative embodiments of the present disclosure have been described herein with reference to the accompanying drawings, it is to be understood that the disclosure is not limited to those precise embodiments, and that various other changes and modifications may be effected therein by one skilled in the art without departing from the scope or spirit of the disclosure.

What is claimed is:

1. A system for performing an endoscopic procedure, the system comprising:
    an actuation assembly having a handle assembly and a shaft assembly, the shaft assembly having an outer tube and a rotation knob secured to a proximal portion of the outer tube;
    an end effector configured for selective and operative connection to a distal end of the shaft assembly; and
    a holder for selectively engaging the end effector and facilitating attachment of the end effector to the shaft assembly.

2. The system of claim 1, wherein the handle assembly includes a trigger mechanism, a slider mechanism, a drive mechanism, and a latch mechanism, and the shaft assembly includes a connection mechanism, the connection mechanism including the outer tube, a center tube slidably disposed relative to the outer tube, an inner tube slidably disposed relative to the outer and center tubes, and a center rod slidably disposed relative to outer, center, and inner tubes.

3. The system of claim 2, wherein each of the outer tube, the center tube, the inner tube, and the center rod extends distally from the handle assembly.

4. The system of claim 2, wherein the center rod includes a pointed distal end.

5. The system of claim 4, wherein the pointed distal end is configured to penetrate tissue.

6. The system of claim 1, wherein the shaft assembly of the actuation assembly includes a cross-section having a first diameter and the end effector includes a cross-section having a second diameter, wherein the second diameter is greater than the first diameter.

7. The system of claim 6, wherein the first diameter is dimensioned to be received through a 3 mm opening and the second diameter is dimensioned to be received through a 5 mm opening.

8. The system of claim 1, wherein the end effector includes a connection assembly and a jaw assembly, the connection assembly includes a tubular body having a pair of distal supports extending distally therefrom for operable engagement with a jaw assembly.

9. The system of claim 1, wherein the holder includes a tubular body, a shaft, a capsule, and an actuation mechanism.

10. The system of claim 9, wherein the shaft includes a distal portion and first and second extensions on the distal portion.

11. The system of claim 10, wherein the first and second extensions taper outwardly and define a slot between the first and second extensions.

12. The system of claim 11, wherein the capsule includes a cylindrical body having a substantially C-shaped cross-section configured to selectively retain the end effector.

13. The system of claim 12, wherein the capsule is pivotally secured to the first and second extensions.

14. The system of claim 13, wherein the capsule is configured to constrict about the end effector when the end effector is received within the cylindrical body.

15. The system of claim 13, wherein the capsule is movable between a first position in which the capsule is axially aligned with the tubular body and the shaft, and a second position in which the capsule is at an angle relative to the tubular body and the shaft.

16. The system of claim 15, wherein the actuation mechanism includes a link operably fixed to the capsule, wherein movement of the link causes corresponding movement of the capsule.

17. The system of claim 15, wherein the capsule is movable through ninety degrees of articulation.

18. The system of claim 1, wherein the handle assembly of the actuation assembly includes a base member, the base member including a handle portion and a distal extension.

19. The system of claim 1, wherein the shaft assembly includes a connection mechanism, the connection mechanism including the outer tube and a center tube slidably disposed relative to the outer tube.

20. The system of claim 19, wherein the connection mechanism further includes an inner tube slidably disposed relative to the outer and center tubes.

21. The system of claim 20, wherein the connection mechanism further includes a center rod slidably disposed relative to the outer, center, and inner tubes.

* * * * *